(12) United States Patent
Scharf et al.

(10) Patent No.: US 7,968,525 B1
(45) Date of Patent: Jun. 28, 2011

(54) USE OF RNA INTERFERENCE TO VALIDATE NEW TERMITICIDE TARGET SITES AND A METHOD OF TERMITE CONTROL

(75) Inventors: Michael E. Scharf, Gainesville, FL (US); Xuguo Zhou, Lexington, KY (US); Faith M. Oi, Gainesville, FL (US); Marsha M. Wheeler, Urbana, IL (US); Matthew R. Tarver, Gainesville, FL (US); Monique R. Coy, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 139 days.

(21) Appl. No.: 12/324,312

(22) Filed: Nov. 26, 2008

Related U.S. Application Data

(60) Provisional application No. 60/991,959, filed on Dec. 3, 2007.

(51) Int. Cl.
  *A61K 31/70* (2006.01)
  *C07H 21/02* (2006.01)
  *C07H 21/04* (2006.01)
  *C12Q 1/68* (2006.01)

(52) U.S. Cl. ............... 514/44 A; 435/375; 536/23.1; 536/24.1; 536/24.5

(58) Field of Classification Search .................. None
  See application file for complete search history.

(56) References Cited

U.S. PATENT DOCUMENTS

| | | | |
|---|---|---|---|
| 6,093,389 A * | 7/2000 | Galinis et al. ............... 424/84 |
| 6,370,812 B1 * | 4/2002 | Burns et al. ............... 43/124 |
| 6,416,752 B1 * | 7/2002 | Richardson et al. ............ 424/84 |
| 6,506,559 B1 | 1/2003 | Fire et al. |
| 6,716,421 B2 * | 4/2004 | Brode et al. .................. 424/84 |
| 6,773,727 B1 * | 8/2004 | Rojas et al. .................. 424/725 |
| 6,964,124 B2 * | 11/2005 | Brode et al. ............... 43/132.1 |
| 7,181,884 B2 * | 2/2007 | Stevens et al. ............ 43/132.1 |
| 2003/0106092 A1 | 6/2003 | Davis et al. |
| 2003/0135888 A1 | 7/2003 | Zhu et al. |
| 2003/0150017 A1 | 8/2003 | Mesa et al. |
| 2003/0154508 A1 | 8/2003 | Stevens et al. |
| 2004/0018999 A1 | 1/2004 | Beach et al. |
| 2004/0098761 A1 | 5/2004 | Trick et al. |
| 2004/0133943 A1 | 7/2004 | Plaetinck et al. |
| 2006/0272049 A1 | 11/2006 | Waterhouse et al. |
| 2006/0288448 A1 | 12/2006 | Abad et al. |
| 2007/0011775 A1 | 1/2007 | Allen et al. |
| 2007/0130653 A1 | 6/2007 | Boulcome et al. |
| 2007/0192903 A1 | 8/2007 | Heck et al. |
| 2007/0199100 A1 | 8/2007 | Michaeli et al. |
| 2009/0010888 A1 * | 1/2009 | Paine et al. .................. 424/93.2 |

FOREIGN PATENT DOCUMENTS

WO  WO 03/004644 A1 *  1/2003

OTHER PUBLICATIONS

Zhou et al PNAS vol. 103(12):4499-4504, 2006.*
Zhou et al Development vol. 134:601-610, 2007.*
Zhou et al Insect Biochemistry and Molecular Biology vol. 38:805-815, 2008.*

* cited by examiner

*Primary Examiner* — Sean R McGarry
(74) *Attorney, Agent, or Firm* — Brian S. Steinberger; Joyce P. Morlin; Law Offices of Brian S. Steinberger, P.A.

(57) ABSTRACT

Methods, matrix compositions and kits for increasing the mortality of termites (*R. flavipes*) and interfering with termite development using RNA interference techniques to target cellulase, lignocellulase, hexamerin, broad, farnesoic acid methyl transferase, cytochrome P450 and vitellogenin activity are provided.

9 Claims, 35 Drawing Sheets

Figure 8A
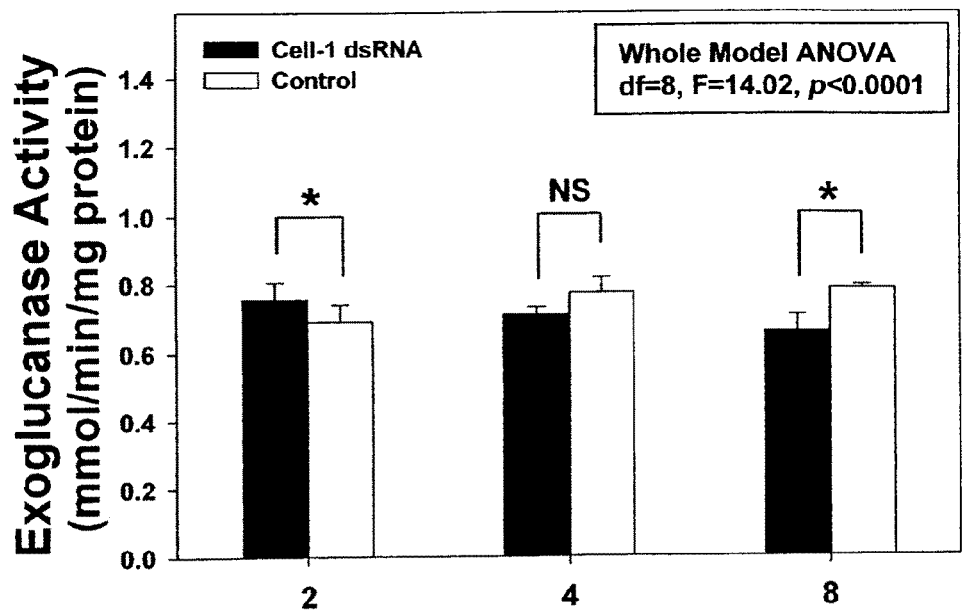
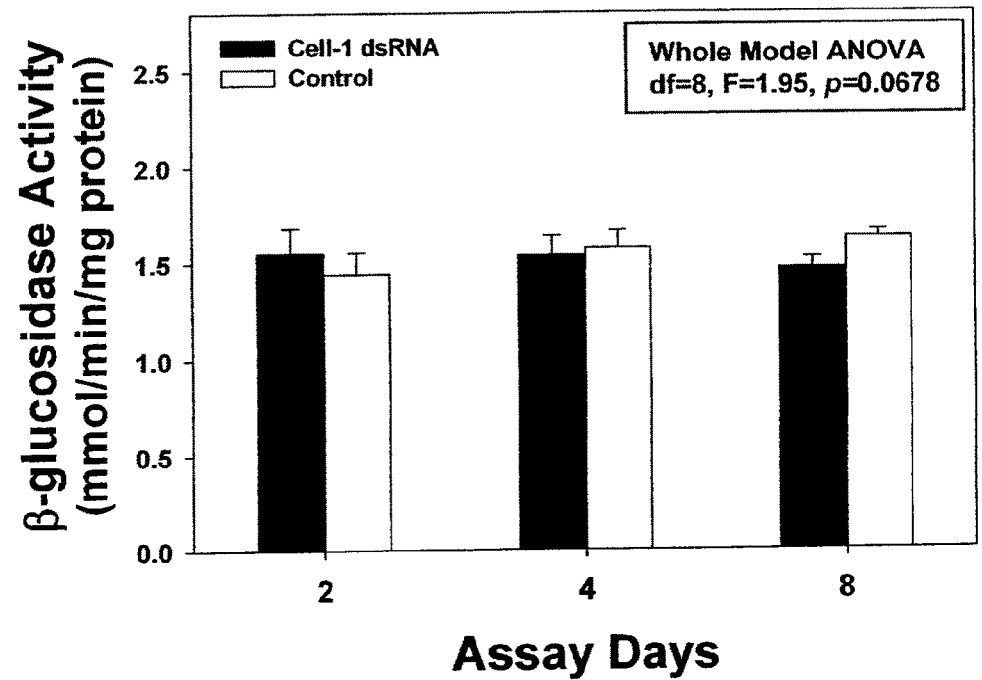
Figure 8B

Cell-1 Priming site sequences

| | |
|---|---|
| dsRNAi-F | 5'-agacatgacgatgtccagacc-3' |
| dsRNAi-R | 5'-gacccttgggtgtcttct-3' |
| qRT-PCR-F | 5'-tcacaagcaagcaggcatac-3' |
| qRT-PCR-R | 5'-atgagagcagaattggcaga-3' |

Hex-2 Priming site sequences

| | |
|---|---|
| dsRNAi-F | 5'-atacgccaatggacaggaag-3' |
| dsRNAi-R | 5'-gcgcttgaggatttggtagt-3' |
| qRT-PCR-F | 5'-acggaagacgttggactcag-3' |
| qRT-PCR-R | 5'-gaggacctgctggatcttgt-3' |

**Supplementary Table 1. Statistical comparisons of CT values between reference and target genes from *Cell-1* dsRNA feeding bioassay** [a]

| Parameter [b] | β-actin | HSP-70 | NADH-dh | Cell-1 |
|---|---|---|---|---|
| N | 72 | 72 | 72 | 72 |
| GM [$C_T$] | 20.60 | 20.76 | 25.90 | 15.11 |
| AM [$C_T$] | 20.63 | 20.78 | 25.91 | 15.13 |
| Min [$C_T$] | 18.88 | 18.84 | 24.53 | 13.66 |
| Max [$C_T$] | 22.68 | 22.66 | 27.65 | 16.94 |
| SD [± $C_T$] | 0.84 | 0.65 | 0.64 | 0.79 |
| CV [% $C_T$] | 4.07 | 3.11 | 2.48 | 5.23 |
| Min [x-fold] | -3.30 | -3.79 | -2.59 | -2.72 |
| Max [x-fold] | 4.23 | 3.72 | 3.36 | 3.57 |
| SD [± x-fold] | 1.79 | 1.57 | 1.56 | 1.73 |
| *Pair-wise correlation with BestKeeper Index* [c] | | | | |
| Coeff. of corr. [$r$] | 0.96 | 0.95 | 0.88 | 0.75 |
| Coeff. of det. [$r^2$] | 0.93 | 0.91 | 0.77 | 0.56 |
| *p*-value | 0.001 | 0.001 | 0.001 | 0.001 |

[a] Stability of three reference genes (*β-actin*, *HSP-70* and *NADH-dh*) across all treatments from *Cell-1* dsRNA feeding bioassays were examined by an Excel-based qRT-PCR normalization software, *Best Keeper*. The differentially expressed target gene (*Cell-1*) was included in the analysis to serve as a positive control and to demonstrate the transcriptional impacts by dsRNA-mediated RNA interference.

[b] Abbreviations for listed parameters: N: sample size; GM [CT]: geometric means of the threshold cycle (CT); AM [CT]: the arithmetic mean of CT; Min [CT] and Max [CT]: the extreme values of CT; SD [± CT] : the standard deviation of the CT; CV [% CT]: the coefficient of variance expressed as a percentage at the CT level; Min [x-fold] and Max [x-fold]: the extreme values of expression levels expressed as an absolute x-fold over/under-regulation coefficient; SD [± x-fold]: standard deviation of the absolute regulation coefficients.

[c] *BestKeeper Index* is estimated based on the weighted expression of all three reference genes. The relation between the index and reference or target gene is analyzed by the Pearson correlation coefficient (*r*), coefficient of determination (*r2*), and the *p*-value.

Figure 16

Supplementary Table 2. Statistical comparisons of CT values between reference and target genes from *Hex-2* dsRNA feeding bioassay [a]

| Parameter[b] | β-actin | HSP-70 | NADH-dh | Hex-2 |
|---|---|---|---|---|
| N | 72 | 72 | 72 | 72 |
| GM [$C_T$] | 20.50 | 20.81 | 26.26 | 18.32 |
| AM [$C_T$] | 20.52 | 20.83 | 26.27 | 18.34 |
| Min [$C_T$] | 18.88 | 18.63 | 24.77 | 16.58 |
| Max [$C_T$] | 23.11 | 23.08 | 28.15 | 19.86 |
| SD [± $C_T$] | 0.72 | 0.74 | 0.56 | 0.78 |
| CV [% $C_T$] | 3.51 | 3.55 | 2.15 | 4.23 |
| Min [x-fold] | -3.09 | -4.53 | -2.81 | -3.34 |
| PMax [x-fold] | 6.07 | 4.83 | 3.70 | 2.90 |
| SD [± x-fold] | 1.65 | 1.67 | 1.48 | 1.71 |
| *Pair-wise correlation with BestKeeper Index*[c] | | | | |
| Coeff. of corr. [$r$] | 0.912 | 0.932 | 0.907 | 0.653 |
| Coeff. of det. [$r^2$] | 0.832 | 0.869 | 0.823 | 0.426 |
| *p*-value | 0.001 | 0.001 | 0.001 | 0.001 |

[a] Stability of three reference genes (*β-actin, HSP-70* and *NADH-dh*) across all treatments from *Cell-1* dsRNA feeding bioassays were examined by an Excel-based qRT-PCR normalization software, *Best Keeper*. Differentially expressed target gene (*Hex-2*) was included in the analysis to serve as positive controls and to demonstrate the transcriptional impacts by dsRNA-mediated RNA interference.

[b] Abbreviations for listed parameters: N: sample size; GM [CT]: geometric means of the threshold cycle (CT); AM [CT]: the arithmetic mean of CT; Min [CT] and Max [CT]: the extreme values of CT; SD [± CT]: the standard deviation of the CT; CV [% CT]: the coefficient of variance expressed as a percentage at the CT level; Min [x-fold] and Max [x-fold]: the extreme values of expression levels expressed as an absolute x-fold over/under-regulation coefficient; SD [± x-fold]: standard deviation of the absolute regulation coefficients.

[c] *BestKeeper Index* is estimated based on the weighted expression of all three reference genes. The relation between the index and reference or target gene is analyzed by the Pearson correlation coefficient (*r*), coefficient of determination (*r2*), and the *p*-value.

Figure 17

Supplementary Table 3. Termite gene identities, abbreviations, accession numbers and qRT-PCR primer sequences.

| Gene Identity (abbreviation) | Accession No. | Forward Primer (5'-3') | Reverse Primer (5'-3') |
| --- | --- | --- | --- |
| *Hexamerin Ligand-binding Proteins* | | | |
| Hexamerin-2 (Hex-2) | AY572859 | ACGGAAGAAGACGTTGGACTCAG | GAGGACCTGCTGATCTTGT |
| Hexamerin-1 (Hex-1) | AY572858 | GATCCATTCCACAAGCACG | ACATTCTCCACCGTCACTCC |
| *Cellulases* | | | |
| Cellulase-1 (Cell-1) | AY572862 | TCACAAGCAAGCAGGCATAC | ATGAGAGCAGAATTGGCAGC |
| Cellulase-2 (Cell-4) | DQ014513 | GCTGGGGGTGTTATTCATTCCTA | CTTCGAGCAAGCATGAACTG |
| *Cuticle and Muscle Proteins* | | | |
| Larval Cuticle Protein A3A-like (LCP) | DN792534 | CGTCGACACCGACTACGAC | GGTCAGCGGGTGTACTCGAC |
| Rfl Troponin-1 [*wup-like*] (Troponin) | CB518302 | CGACCTAGAATACGAAGTGG | TTCTTCTTCCTTGTCCTCCTCC |
| *Transcription and Translation Factors* | | | |
| BTB-POZ [broad-like] | AY258590 | CTGGACCAGCATCTACATCTTC | GGTTGAAGCCTGATTCACAAG |
| Legs Incomplete and Malformed (LIM) | CB518301 | GTGCTTCAAGTGTGGCATGT | GTCCATGCTGAGACAACCAG |
| *Reference / Control Genes* | | | |
| β-actin | DQ206832 | AGAGGGAAATCGTGCCTGAC | CAATAGTGATGACCTGCCGT |
| NADH-dh | BQ788175 | GCTGGGGTGTTATTCATTCCTA | GGCATACCACAAAGAGCAAAA |
| HSP-70 | BQ788164 | AGAACCAAGTGGCCATGAAC | CCAATGCTTCATGTCTGCC |

Figure 18

***RETICULITERMES FLAVIPES* CELL-1 ENDOGENOUS CELLULASE mRNA, COMPLETE CDS.**
GENBANK ACCESSION: AY572862

```
   1 CCACTACCAG CCGCCATGAA GGTCTTCGTT TGTCTTCTGT CTGCACTGGC GCTTTGCCAA
  61 GCTGCTTACG ACTATAAGAC AGTACTAAGC AATTCGCTAC TTTTCTACGA GGCTCAGCGA
 121 TCGGGAAAAT TGCCGTCTGA TCAGAAGGTC ACGTGGAGGA AGGATTCCGC CCTTAACGAC
 181 AAGGGCCAGA AGGGCGAGGA CCTGACAGGA GGATACTCTG ACGCTGGTGA TTTTGTGAAG
 241 TTCGGCTTCC CTATGGCTGA CACAGTCACC GTCCTCGCTT GGGGTGTTAT AGACTACGAA
 301 TCAGCGTATT CTGCAGCAGG AGCTCTGGAT AGTGGTCGCA AGGCTCTTAA ATATGGCACG
 361 GACTACTTCC TCAAGGCGCA CACGGCCGCG AACGAATTCT ACGGACAAGT GGGCCAGGGA
 421 GATGTCGACC ACGCCTACTG GGGACGTCCA GAAGACATGA CGATGTCCAG ACCTGCCTAC
 481 AAGATCGACA CGTCGAAACC AGGGTCTGAC CTGGCAGCCG AGACAGCCGC CGCCCTCGCT
 541 GCAACTGCCA TCGCCTACAA GAGTGCTGAC GCAACTTATT CCAACAACTT GATCACCCAC
 601 GCCAAGCAGC TTTTCGACTT CGCCAACAAT TATCGCGGCA AATACAGTGA TTCAATCACC
 661 GACGCGAAGA ATTTCTACGC GTCCGGAGAC TACAAGGACG AGTTAGTATG GGCAGCCGCA
 721 TGGCTCTACA GGGCGACCAA CGACAACACC TATCTGACTA AAGCTGAATC GCTATACAAC
 781 GAATTCGGCC TCGGAAACTG AACGGTGCC TTCAACTGGG ATAACAAGAT CTCCGGTGTA
 841 CAGGTTCTAC TGGCCAAGCT CACAAGCAAG CAGGCATACA AGGACAAGGT ACAAGGCTAC
 901 GTCGATTACT TGATTTCGTC TCAGAAGAAG ACACCCAAGG GTCTCGTATA CATCGACCAG
 961 TGGGGTACCC TGCGACATGC TGCCAATTCT GCTCTCATTG CTCTGCAGGC AGCCGACCTG
1021 GGTATCAATG CTGCTACTTA TCGCGCGTAT GCCAAGAAGC AGATCGATTA CGCATTGGGT
1081 GATGGAGGTC GCAGCTACGT CGTAGGATTT GGTACTAACC CACCCGTACG CCCTCACCAC
1141 AGATCCAGCT CGTGCCCTGA CGCACCAGCC GTATGTGACT GGAACACGTA CAACAGCGCC
1201 GGCCCCAATG CCCACGTACT CACCGGAGCC TTGGTGGGTG GTCCAGATAG CAACGATAGC
1261 TACACGGACG CTCGCAGCGA TTACATCTCC AACGAAGTGG CCACAGATTA CAACGCTGGC
1321 TTCCAATCAG CTGTCGCTGG TCTCCTCAAG GCTGGCGTGT AACCGCACAC AGCACTCAAT
1381 GTCTCCCTGT CCACTGGACA TGTGTACAAT TTGACAACGA AAATGTAATA TTCTTCAGAA
1441 AAGTGCAATA AAAGTTCACA ATTCAACACA AAAAAAAAA AAAAAAAAA
```

FIGURE 19

RETICULITERMES FLAVIPES HEXAMERIN I (HEX-1) mRNA, COMPLETE CDS.
GENBANK ACCESSION: AY572858

```
   1 CTAGTCTGTT TTTTTTTTTT TTTTTTCAGT TCCTCATTCA CTCTTTCCGC CTCCAATTTC
  61 CTCGCTTCCA ACACTTTCTT TGCTGCCTTG TTAGCCTCTT CCTTCTCCTT CATTGCCTGT
 121 GCAATCCCTT CTTCCTTTTC CTTCTTTGCC TGTGCAATCT TCTCTTCTTC CTCCTTCTTT
 181 GCCTTTGCAA TCCCTTCTTT TCTTTCCTTC TTTGCCTGTG CAATCTGTTC TTCCARTTTC
 241 TTCCTTAATT CCACATTCTC ATTTTCCGCC TTTAATTTCG TCACTTCCAA CACTTTCTTT
 301 GCTGCCTTGT CAGCCTCTTC TTTCTCCTTC ATTACCTGTG CAATCCCTTC TTCCTTTTCC
 361 TTCTTTGCCT GTGCAATCTT CTCTTCTTCC TCCTTCTTTG CCTGTGCAAT CCCTTCTTCT
 421 TTTTCTTTCT TTGCCTGTGC AATCTCATCT TCTTTTTCTT TCTTTGCCTG TGCAATCTGT
 481 TCTTCCATTT TCTTTTTCAG TTCCTCATTC ACTCTTTCCG CCTCCAATTT CCTCGCTTCC
 541 AACACTTTCT TGCTGCCTT GTCAGCCTCT TCCTTCTCCT TCATTGCCTG TGCAATCCCT
 601 TCTTCCTTTT CCTTCTTTGC CTGTGCAATC TTCTCTTCTT CTATGAACAC TGCTCTCCTG
 661 TTCGCGACAG TCGTGGCCGT CTTGGTCTGC GGCGCCTTCT CTGACCACCA TGTAGGGAAG
 721 AAAGTAGCAG ACAAACCGTT CCTCATGAAG CAGAAAAACA TCCTAGGGCT GGTCCACAGG
 781 ATTCATCAAG ATAATCTATT CAAAGAGCAG GTTGATGTGG GTAATACCTA TGACATTGAA
 841 GCACATATCA GCAACTACAA GAATACAAAA GTAGTGAAAG AGTTTATATC CTACTACAAG
 901 AAGGGCATGC TGCAACGCTG GGAGCCGTTC TCAGTGTATT ACAAGACTCA CCTTGAACAG
 961 GCTATCTCCT TGTTCGAGCT CTTCTATTTC GCTAACGACT TCGATACTTT CTACAAGACC
1021 GCCTGCTGGG CCCGCGACCG TGTGAACCCG CTCATGTTCT GGTATTCTTT CACTGCTGCC
1081 GTCCTCCACC GCGACGACAC GACAGATGTC ATGATGCCGC CGCCCTACGA AGTGTACCCA
1141 TACTTCTTCG TAGACAGTGA TATCATCCAA AAGGCCTACA AGTACTGGAT GATGCACGTT
1201 GGCACCACTG AACATCACAC CTACATCATC CCAATGAATC ACACCATGAA GAGCAAGGAG
1261 AATTTGCTCT ACTACTTTAC AGAAGACGTG GGCTTGAACG CTTTCAACAT GTACTACCGC
1321 ATGTACTACC CCAGCTGGTT CAACGTTACG GAGTACGGCC ACAAGTTCGA CCGTCGCGGC
1381 GAGATGTTCC TCTACGTGCA GCACCAGCTG TACGCTGCT ACAGCTTGGA GAGAATGTCC
1441 AACGGCATGC CCGAAGTTGA GCCCTTCGTC TACAACAAGA CCCTCAAGAC CGCATACAAC
1501 CCCAACCTGA TGTACCACAC CGGCCAAGAA ATGCCTCCAC GCCCCAGCGA CATGCTCGTG
1561 ACTAACTTCG ACACGTACAC CATCGAAGAC ATCAAGAACT ACGAACGGAG GGTGGCGGAC
1621 GTAATCGACT TCGGCTACTT CAAGGACGAA CACCTCAAAG TTCACTCCAT GTACGAGGAT
1681 AATAATGGCA TCAACTACCT AGGCCAGATG ATAGAAGGCT CCTACAACTC CCCCCACTAC
1741 TATTACTACG GTTCCCTGTT TCACTTCTAC CGCATGATGT TAGGGCACAT GATGGATCCA
1801 TTCCACAAGC ACGGGCTCGC ACCCAGCGCC CTGAACAAC CAGAGACAGC CCTGAGGGAT
1861 CCCGCCTACT ACCAGCTGTA CAAGCGAATG TACCACTTAG TCAATAAGTA CAAGGACAGG
1921 CTGCCTCGCT ACACGCACGA ACAGCTTTGG TTCGAAGGAG TGACGGTGGA GAATGTGGAT
1981 GTTGGTAAGA TGTACACGTA CATGGAGAAC TTTGAGTTTA GCCTGGGCGG CACCATATAT
2041 GTGGCCAAGG AGGAGGATAT GTTAGGTGTG AACTTGCATG TTCGGCAGCC ACGTCTGAAT
2101 CACAAGCCAT TCACCTATAA GATAGAGGTC AGCAGCGAAA AGGCAGTCGA TGCATACGTG
2161 CGTGTGTTCT TGGGCCCCAA GCATAATTAC CTGGACGAGG AATGGGACTT GAATGAGCGC
2221 AGGCACTTCT TCGTCGAGAT GGACCGCTTC CGGCATCATG TCCCAGCTGG CAAGAGTGTA
2281 ATCGAACGCA ACTCCCACGA CTCCTCAATA ATTGCACCTA CACCCGACAG CTACAGGACA
2341 TTCGTCAAGA AAGTGCAGGA CGCTTATGAT GGCAAAACCC AATACTTCAT CGACAAGAGC
2401 CACAACTACT GCGGATTCCC CGAGAATCTG CTGCTGCCCA AGGGCAGAA GGGAGGTGAG
2461 ACCTTCACTT TCTACGTCAT AATCACGCCA TACGTCAAAC AGGATGAGCA CGACTTCGAG
2521 CCTTACGACT ACAAAGCCTT TAGCTAATGC GGCGTGGGAC AAGACCGCAA GTATCCTGAC
2581 GACATGCCAC TGGGATTCCC CTTCGACCGC CAGATCCATA GCAAGGACTT CTACACCCAC
2641 CAACATGTAC TTCAAGGATG TACAATCTTT CCACAAGAAA CTCGAAGAAG TCAGTACTCC
2701 CACCCACTAG GACAACAATG TGAGATTTCA ACGTCACATC TGTTGAGCGG AAATGGGTTC
2761 AGTATTTCGA AACCTAAGGC AACTGACATA TTGCAATCTG ATGTCCTCAC ATTGGTGAAT
2821 ATAATACTGC GGTTTTCTGG AATGTGTTGT CGTATATTAT GGTAGAGTAT GTGCTAAAGT
2881 TTCGGGGGAG AATACTACCA CCATTCTACC CAGAAGAAGT AAGCACCATG TTTCTCCAAG
2941 AAGTCGGTAT CTATCTACCA AATAAAGCGG CGCCAAATCC CAGAAGGCAG TAGTCCTAAC
3001 CTGAAATACT GATGTACAGT TTCAAACTTA ACGACCAGTT TCTGTTGCAA TACTGAATTC
3061 ATGATCTATG TATCGTATTT TTTGGCTTCG ACCGATCGT AAGTCACGAT GAATGACTAC
3121 TCGCTTGTAC TGGAGAATTT GAACTGAATC ACTTTATACA TTATCTGTGA GATGTGTATG
3181 TCCAATCTTT AATAGATAAA ATAGTGCAAT AAAAACAGAA ATATAAAAAA AAAAAAAAA
3241 AA
```

FIGURE 20A

*RETICULITERMES FLAVIPES* HEXAMERIN I I (HEX-2) mRNA, COMPLETE CDS.
GENBANK ACCESSION: AY572859

```
   1 GCGACCACCA TGAGGACAGC AGTGCTGCTC GTGTTTCTGG CCACAGCGGC CCTAGCAGCT
  61 GCAAACCCGA GCCCAAGCTA AGAGTCCAGA ATCATCGCTG ACAAGCAGTT CCTGCAGCGG
 121 CAGAATGACT TCCTGCGCCT CCTGGTCCGC ATCGAACAAC CAAATTACTA CGAAGACCAG
 181 GTGACACTCG GCAATTCATA CGACATCGAA GTGAACATCA AAAACTACAA GCACCCTCAA
 241 GTGGTAAAGC AGTTCTTGTC AGCCTACAAG AAGGGTTTCC TGCCTCGTGG TGTGCCATAT
 301 TCTCCCTACT ACACCACCCA GAGCTACGAG ACCAAGCTTC TGTTCGATCT GTTCTACTAC
 361 GCCAATGACT ATGACACTTT CTACAAGACT GCAGTCTGGG CTCGTGACAG AATCAACGCA
 421 GGCCAGTTCC TGTACGCCTT CAGTGTGGCC ACCTTCCTAC GAGAGGACCT GAACGACATC
 481 GTGTTGCCAC CCCCTACGA GGTCTACCCG TACCTCTTTG TAGATTCTGA CGTCATTCAG
 541 AAGGCTTACG AGACAAAAAT GTGGGATCAC AGTCTGACGT CCCCTAAGAC GCACGTGTTC
 601 CCAGCTAACT ACACTGTGCA CACCCCGGAA CAAGTCCTCA GCTACTTCAC GGAAGACGTT
 661 GGACTCAGCA CGTACTACCT CTACTACTAC TACAACTACC CCACGTTCTT CAACAGCACC
 721 GAGTACGGCG TTCATTTCGA CCGTCGCGGT GAGCAGTTCT ACTACAAGAT CCAGCAGGTC
 781 CTCGCCCGTT ACATCCTCGA GAGGCTGTCC ACGACCTTC CAGAAGTCCA GCCCTTCCAT
 841 TATGACAAGC CCTTCCAGAC TGCGTACTAC CCTAAGCTGC GATACGCCAA TGGACAGGAA
 901 GTTCCGTTCC GCCCATATGA ATACAGCAAA CGCAACCTCT ACAACTATAA CGGCCAAGGC
 961 CAATACTACG GCAATTACTA TGGCGGTAAT AACGAATACT ACAGTGGCAA CTACTTCACC
1021 GGTAACTACA AGCCAACCTA CTACTACGGC TATGCCAATA ACTACGATTA CTACTATCCA
1081 GAGGATATCA AGTCCTACGA GGGTCGCATT AGAGATGGCA TCGACTTCGG ATATTTCTTC
1141 TCTGAGGGAG GACAACCAAA GTATCCTCTG TATGACGAGT ACTCAAAGGG CATCAATTAC
1201 CTTGGTGACA TCATTGAGGG CAACGGCGAC ACAGTCAACA AGAGGGTCTA CGGAGCCATC
1261 TACCAAGCCT ACCGCCAACT AGCCGGACAG AGCGCCGATC CCTACAACAA CTATGGGCTC
1321 GCCCCAAGCG CACTTCAGAA CATCTTCACG GCTCTGAGGG ACCCCGCCAA CTACCAAATC
1381 CTCAAGCGCA TCACTTACCT GTTCCAGAGG TACAAGAACT ATCTCCCACA GTACACGTAC
1441 CAAGAGCTCG CTTATCCAGG GGTTACAATT GAAAATGTGG AAGTAGGAAA GCTGATTACT
1501 TACAACGATT ACTTTGACAT CGACCTCGAC AACGTAGTGA ACGTGAAAGT GCCCGAGGAC
1561 GGTCAGTACG TCGACTACCG CGCACGCCAG ACACGTCTGA ACCACAAGCC CTTCACCTAC
1621 AGCATAGACG TAACCAGCGA CAAGGCGACC GAAGTGTATG TCCGAGTCTT CCTGGGCCCC
1681 AAATACGACT ACCTGGGCCG CGAGTACAAT ATCAACGACC GCAGACATTA CTTCGTCGAG
1741 ATCGACCGCT TCCCACACAA GATACAAGAG GGCAAGACGA CGATCAAGCG AAACTCCCGC
1801 GACTCCAGTG TTGTCACTCC AGACTATCCA AGTTACAGAA CTCTGCTCCG GAAGGTGAGC
1861 GATGCGCTCG AGGGCAAGGA GCAGTTCTAC ATCGACAGGA GTGAACGCTA CTGTGGCTAC
1921 CCCGAGCGCC TGCTGCTTCC TAGAGGCAAG AAGGGAGGCC AGTCCTTCAC CTTCTACGTC
1981 ATCCTGACAC CCTACGTCCA GCAGGGCGAA CATGAATTCG AGCCCTACAA TTACAAGZCA
2041 TTCAGCTACT GTGGAGTTGG CTTCAACAAC AAGTACCCTG ACTATAAGCC CCTCGGGTAT
2101 CCATTCGACC GCCCCATCTA CGGTAGCGAC TTCTACACCA CCAACTCGTA CTTCAAGGAC
2161 GTGGTCATCT TCCACAAGAA GGAGGAAGAA GTGAATACAG CCATCACACA GTGACACGCC
2221 ATGTAACTGG AGAAATATAG TTACGATAGC AATACGAGGT GGTCCAAAAG TCTCTGTGCA
2281 GTTGCAGACA TTAAATTATT AAGATGAGTG GAAGTAATCG TTGCTGCGGC AACAATTTGT
2341 TTCATTCATA TGAGGTCCAA GTAGCTAAAC AAGTCCDATC ATGAACGAGA CCCGTCTGCA
2401 CAGGGCCTTT CTGACTATTA TGTATGACAA GTCCGTCCTT CGTATTTGTT GACGAATCGC
2461 ACCGACCAGG ACATTCTGTG GAAAGCTGAA TGTAAATGTG TTACCGTTTA GAGACTTTCG
2521 TTTCTGTCCT TCAGAATAAA TACCCTTTTT TACTAGCCTG CAATAAACAA AAAAAAAAA
2581 AAAAAAA
```

FIGURE 20B

*RETICULITERMES FLAVIPES* FAMILY 15 CYTOCHROME P450 NUMBER1 [RF_CYP15-1] GENBANK ACCESSION NUMBERS FL638893, FL636088, FL636256, FL636262, FL640637, FL640773, FL635527

TATCATTGTGCAGAGAAGAAGGCGAAAGTGTTGAGCAGTGAAATATACGTACTTGGATACACAGTGGGTAC
CATGTTCTTCTCATTGTTTATGGATCATCTTCTTTCCTGTGTTTCTATGTGGTATATTACTGGCTAACAATGAAGCCGA
AGAACTTTCCGCCAGTCCACCACATGTTCCTGGTGTTTGGATCTACCTTTACCTGCTACGGAAACATCTT
CACATTCCGATGGCAGGGGAATGGCTTCAGAAATACGGTCCTGTTGTGGGATTTGTGGCGGCCTCTCGGAA
GATCATAGCGATATGTGGACCCCGTGAAGTCCTTGAAGTGCTACACAGAGATGAATTCCAAGCAAGGCCTG
TCTTTAGTTTTTTTCATGATAGGTCTTTCGGCAAAAAACTCGGGTGTTTTTCTCTGATGGCCCGTACTGG
GTAGAACAGCCCAGATTTACTTCTCAGACATTTGAGAGATTTCGGTTCGGAAAACGTTCAATGGAGGAGTT
CATCATGGAAGAATAGAAGACACTATCAAAGACAGAAATTACAAAGACAGAAATTATGCAGGCCACTGGATTGT
TCACTATTGCCACACTGAACGTTCTATGGAGACTTCTGTTCCGGTCTGAAGTGCCGGTGGAGGTATTGGTGGTGC
ATGCTGATGCTTCTAGAGAAACTGAGAACTTGCACCCCGTATTTCTGGTTACGCCTTAATGATGTCCACCACTTCAGATT
ATTCCCCATCTTAACGAAAATTGCACCCATAAGGGAACACGAGAAAACTATGGATGAGAATAACGCAAGAGATTTA
TGCAGGAATTTTTCAGAAAATCCATAAGGGAAAATAAAATTACAAGGCAATAATCCGGCCTCAACATTCACAGAAGAAGGCT
ATTGATGTGTACTTAAGGGAACTTGTTCACTGCCGGAGGAGAAACCATGGCCATGTCTCTAGGCTTCTCCCTTC
CATAACGATCGCCTGGACTTGTTCACTGCCGAATGTCCAAAAGGCGGTGCAGAAAGAGTTGGATGCAGTTGTGTGGAAGGAC
TGTACACATGCTGGTCGTGGTGCACCCGAATGTCCAAAAGGCGGTGCAGAAAGAGTTGGATGCAGTTGTGTGGAAGGAC
AGGAGACCCACTCTTCAAGACAGAGCAAGCTTACACTACACAGAAGCTGTACTGTGTCAGAGCTGATT

FIGURE 22A

RETICULITERMES FLAVIPES FAMILY 15 CYTOCHROME P450 NUMBER2 [RF_CYP15-2]
GENBANK ACCESSION NUMBERS FL638893, FL640637, FL640773

GCATATCAAGAACTTTATTTTCGAAAATAAAATCACGTAGCAATTGATGTG
CGTGCCCATTTGCTTAAAGACTGAATAACTGAAGCCTATGGAGCAGTTCTTGAAAAGGCCAACATGGATG
CCAGTGGTAGGAAAACTACTTCTGGTTCCGACAGCAGAAGCTGAGTCTCGGTTACTACCACCTCGTATGGGC
TAGCCTGTGTCAACAAAATATGGGCCTGTGGTCCGGGCTCCGACTGGGCAGGGACTCTGTTGTCACGGTGTCGG
GCTATGATGCTATCAGGGATGTTTTGCTGCGAGATGAGTTTGATGGCAGACCTGATGGATTCTTCTTCCGT
TTGCGTACTTTTGGGAAGCGACTTGGAGTTGTGTTTACTGACGGCGAAGCATGGACGAACAGATAGAAGCGGAGGCAC
CTGCCTCCAACATCTGCGCAAGCTGGGACTTGGGAGGCGAAGCATGGACGAACAGATAGAAGCGGAGGCAC
AAGACCTGGTGGTGAACAGCCTGTGGGCCATGCTGGCTGGATATCGTTTTGCACTGAATGACAAACGCCT
AATGTCTGTGTTCTGAACAGCCTGTGGGCCATGCTGGCTGGATATCGTTTTGCACTGAATGACAAACGCCT
GATGGAGCTCCCTTGACATAGTTCATTGCACCAGAGTTCAACGAGTTACTTGCAATCCTTAATCGAATG
TGCCCTTCCTACGCTTCATTGCACCAGAGTTCAACGATCGCAAAACATTCAGCCCTGATTGTACCAGAGACCTGAT
TGGAACTTTCTGAGGAAACGATCAGTGGAACTCAGAAAGAAACAGATTCAGTTTATGACTGCAGTTGTAGC
TGATTCATTTCTTGAGGAAATGCNGCTCAAGACACAGCAACNGCTCGTTCNCATGCTGTNTATGCTGCTNCCCT
ACTGTGCCTGACTGTCATGCNGCTCAAGACACAGCAACNGCTCGTTCNCATGCTGTNTATGCTGCTNCCCT
GATGTCCNNNNCCNNNACAAGGATGANNTGGNNATTGGGNTGGCCGANNNNNCNNNTCGCNGNACNNNAGTA
GNNAAGNTG

FIGURE 22B

*RETICULITERMES FLAVIPES* FARNESOIC ACID METHYL TRANSFERASE NUMBER2 [RF_FAMET-2] GENBANK ACCESSION NUMBERS FL639748, FL638947

TAGTGGTGTTGGCAGCGGAAGGGAACGGTTTGCAGTGAACATGGCTAAAGAATTTACGACAGAAGACAAAC
TTGAATACCAATTCCATCCTGTAACATCAGGGAAGCTGCATTTTAAGGTGCGGGCACCAAACGATGCGCAT
GTGGCACTGACATCTGGGCCCACTGAAGGGGACCCTATGTACGAGATTTCATTGGTGGCTGGGGAAACGC
GAAGACTGCCATCAGACGAGACCGCGTGAAACCTGACAAGGCTCTAGTCGACACGCCGGACATCCTCAGTG
ATGCAGAATATCGTGGCTTCTGGATCCGCTGGGAGGATGGTTTACTGGCAAGGAAGGTGAAGTG
ACCCCTTTTGTAAGCTGGAAGGACACCCTGAACCGTTTGGTATCGGCTATTACGGTATCTGCACTGGATGGGG
AGCATCTGGCTCATGGATTATAGATGGTGCCGACGTCGCAGACAGTTTGCAGTACATTACCGCC
CCGTGCCAGCGGCGCACTGAGGTTCGTGCCCCCTCCAATGCACACACATTGCTCTAACATCAGCC
AGTAATGAGACAGAACCTATGTACGAGATTCTGCTTGGAGCTGGGAGAACACAGCATCTGTCATTCGCTA
CAACCGCCAGAAACCAGCAAGGTTCGGCCATGTCAGAGTGAAGAAGATGGTTCTGTGCTCAGGACACTGGAGGGTCCACC
TCTTGATAGAGTGGCATAATGGCCACTTTGGTGTGCGGACAGAATTGCCATCTGAGAGCTGCTCTGGGTGCCTGCTCAAGT
CTAGTGCATCACCAGCACCGCCACCTGATGGAAATTGCCATCTGAGAGCTGCTCTGGGTGCCTGCTCAAGT
TGAGACGTCCTCAAATGCTGTGAGGTGTCACGATAGTGAGATTCTGTACATAGACGAGCAGCATGAAGGCG
CCCTGATCNGCAGNTGTNCTCCATGGANNGNTATTNCATGNGAGAACCTTGGACAATGGAGNCACNGAAAT
TGNNGAGGTN

FIGURE 22C

RETICULITERMES FLAVIPES "BROAD" HOMOLOG, BTB/POZ DOMAIN-CONTAINING PROTEIN, COMPLETE CDS [RF_BROAD]
GENBANK ACCESSION NUMBERS AY258590.2

GGCACGAGGTGCTGATCCGGCGTTCATGGACGTCTATACACAGCGCGGCGTCACCAGCCGGCGAACTGGG
CAGGTCCAACACAGGCCCCGCCCGGAACAAAGCGGCTGTGGCCCATCGCCACCCGTCAAAAAGACTCTA
CCTCTAGTTTCACAGGCATCTCCTAAGTCAGTCATCGCTAAGCCAGTTCCTCCACGACCTGTGTCTCCACC
ACAACCCCCTCCACCTCCACCGAAGTTTGTCACCGTTGGATGTCACAGCTACCATTCTAACATGCAAGCTACAT
TCCCAAGTCTGCTGAACAATGAACAGTTTGTGATGTCACATTGGCTTGTGAGGGGCGCAGTATTAAATGT
CGTAAAGTAATGCTATCAGCATGCAGCTCATACTTTGAGGAGTTGCTAAGCCAGAATCCTGCCAACATCC
CATAGTTCTCATGAAGGACCTCAAGTTCTGGGAGGTGCAGGCCCTTGTGGACTTCATGTACAGGGGGAAG
TGAATGTGGGACAAGACAAACTTCCCTCTCTGCTAGCTAGCAGACTCTCTTCCCCCTACTCTTCCGCTCGCAACGATGA
GGACCAGCATCTACATCTTCATCACATGACGAAGAACTCTCTTCCCCTACTCTTCCGCTCGCAACGATGA
CTACATGGATGAATCCGCTTCCTCAGCTGCAGTGCAAGAAGGGCCAGAAGAGGAGAACCACGTTGATCAGGCCA
TGCCAACTCCAACAGAACACCATCTCCTCCACACCGCAACCCAGTGGGCCGACCACGTTTGATCAGGCCA
TCACCTCAACCATCTACATCAACTTACCATCATCATCAGTGGGAGATTAAGAGCCAGTGGATATTGACATTAGCAATG
GAGATCTGAGCCAACTAGTCTTCTGATGATGGATTTGACCTCAACAAGACTTATGACGGCAGTGGTGGAGGACGCAGCAAT
ATTCTATAGACCCTGTGTGATGATGGATTTGACCTCAACAAGACTTATGACGGCAGTGGTGGAGGACGCAAT
GCAAATGACTCCAGTAGGCAAGCGGATGACAATACGGGGTAGACATAGGGGTAGACACTGGAGGAGAGGAGTAAGCAAGAACTCAC
TGGCGATCTCTCAGATGACAACAAGGCAATTGAACTGTGGCTGCGCAGGTGGCGAAGCAAGGCAGAAGGT
GCAGTGGTAACAATGGTATGAACATGCTGAAACGAAATACTGATGACCAGGATGTCTTCTTCAGACATGAATCCAACATA
CAGGGATACTCATATGCTGAAACGAAATACTGATGACCAGGATGTCTTCTTCAGACATGAATCCAACATA
CCCAGAAGTGGTGCTGAAAACCAGGCCTGACAATGCTTCGTCAGATAGCATTCTTGACACTTGTGAATCA
GGCTTCAACCACTATTATGTTTGACTGATTTTATGTATACATTCATCCAAATCGAGGTTCCCCACTGGT
AATGCGATGCTTATCTGATATGGAGTGGAACGAGCACATTGCAGTTCCTCTTCTTAAGTTCTACAGATTCAGTATTTCTTT
AGTTTGCCGGCCATAGTATATAATTTGTAAGCCAAATTTATAAGTCATGGATTATATACTTACTACAGGGGCGTACAGAAT
AGTTAGAAGTGACATATAATTTGTAAGCCAAATTTAAAGTCATGGATTATATACTTACTACAGGGGCGTACAGAAT
GTAGCTTGGGAGCTTGACCTGGAATCTGTAGCCTAACTTAAAGTGTGAAGCTGCTGTAACCATAAATGAGCAG
TTTATAAATGTCTTGGAATCTGTAGCCTAACTTAAAACCAAAAGTGGCTAGAGTCAACAAAAACCTAGTGTGTAGTAT
ACTTTTTGGCATGTAGGTAGTTATTAAAACCAAAAGTGGCTAGAGTCAACAAAAACCTAGTGTGTAGTAT
TGTGGTTACAGCATCATAGCAACATTAGAGTATTGAGAAGGTGTTCTGTATTCATATTCCTGAAGAAATAA
ATGACACTTTGTGAGTTGTTAAGAAAAAAAAAA

FIGURE 22D

RETICULITERMES FLAVIPES VITELLOGENIN-1 [RF_VIT-1]
GENBANK ACCESSION NUMBERS BQ788169

CACTTCTCAAGGTAGAATGGAACAATCTTTTGCTTTCAAACAGTTCGTTGCTGAAAGCCCTATGGCCAAG
TTATGCGAGTCGCAAATGCGCGAAAAACAATCTCCTTAGTGCTTGCCGTAATGTCACTGAGCAAGCCAACG
TACTCGACCTGCACAACTTCGCGCTGAAGTACAACAATATACCCGACTCATGGATAATTACACATACAAG
GCATACAGCGTACTTCGTCACTTGGCTTTCCCTTATGTCACTGAGAATATTTCCACCAAATCCAAAACC
GAACCAATTGCAAGTTAACGTACGCCTGAATAACAACATTACTGCCGTCAACGTATCCATTGAAACGCCAA
TTATGAACATAAATGTCACCAATATCCGCCTGAACCCACTGGCAGCAGCTTTACTTCAGCACAATGCAGAA
GACTCTGCTGCTGACAGAATTGGAAATGCCATGTCACCACTGTACTACCAGCCTACATGCGTTGTTGATGG
CAATGCTGTCGACACGTTCGACACAATACCTATCCAATTAAACTTGGCAGCTGCTGGCATGTCATGTGATGA
TGGAAGTACCAAAGAACCCTGCTGGAGTGCATAGTCGTCATCAGTCGCGATCTTCCCTGGCCAGTGATCCT
CAGACTAGCAATGTAGCGGTGCTCGTACGTGGCAGCAACTCCCGAGTCAACCAGTTCAAATAAATTAGTGGAGGTCGCTGTGAATG
GGGAGAGAATGTCATCACACTGAGTCCCAACAAAACCAGGGAATTTTATTACGAAGGAGTGCTGGTTGTCCAAGTG
ATCGTCAAATCCGATTCTCACCCAACAGACTTCAACTTCCCGAACCACAGCTTGGCGATCGCCTACGATGGAGA
TATGAGTTGCCAAGTGGGAGCTGGAGCTAGTAATGACTATCGCGATGAAGTCCGGGGCTTGTGCGAACTTTCAATGGAG
ATGCTCTCTGACTTCAAATTCCAAAGGGCTGCATTGTTAAGAACCCATACATCTTCGCTGCCACTTAT
GCAATCATTGAAGAGTCTTGCAATGCACAGACCAAGAAGCTGAAGAACGTGTCCATCAAGAACCGTGTGT
GTATGACGAGGTAGAGTACGTCGACGTGATCGCAGAAGAACAGGCCAAAGAACGCTAGTGCAAGAGGATTCG
AACTGCTTAGTTCTGCCAGTGATTCATCCTCGATTCATCATCATCATCAGATCCAATTCCAGTTCTGATTCTGC
TCTTCATCGTCATCATCATCATCATCTTCATCATCATCAGTTCCAGTTCCAGTTCTAGCTCGGAATCCGATGAAG
CTCCAATTCGACTTCAAGCTCCAGTTCCAGTTCCAGTTCATCTAGCTCGGAATCCGATGAAG
TTACCAAAGTCGGAAAAACACCAGAAAGCTGGATCAAAAGCTAATGCCATATCACATCGTACCAAGGTGGTG
ATTGAAGGAAACGAGATTTGCTTCAGCATGAAAACCCCTTCCCGAATGCTCTTCACAATGCCGTCCCGCAGA
AAAACAGAAGAAACTATCAAATTCCACTGCTCTTGTCAAGGGACAGACAGCCCAGCATTGGCAGAATATGG
TGAACAGAGGGGCTAAATCCTGAATGACATAATATTTCAGGATTAATGGAAATAGATTTTACGGACTTTCCTTAT
AAGTGTGCCAGCCTTGAATGACATAATATTCAGAAGTCTGTGTTTAATTTACGACCAATGCAATTGAGCAATGAGATA
ATGTAATATTTATCTAGAATGTGTTGTTGAAACGTTTTAATTTACGACCAATGCAATTGAGCAAAGAAAAATACATAA
AAATATGTGTATTACAACTTATTTATGAAGAATATATCAATTGCAAAAAAAAAAAA

FIGURE 22E

RETICULITERMES FLAVIPES VITELLOGENIN-2 [RF_VIT-2]
GENBANK ACCESSION NUMBERS CB518311

TAGGAGCCGTAAACCACGAGGTTTGCCCAGAAGCATGGGCATAGCAGTGAAGAAAATGATTTCAAGG
CTTCGAACCCAGCAATTCCAGAATCAAGTACATCTCCTGACAGTAATGCTCGCCGGCAGGAATTCCTC
TCCAAGGCTGTTTCAATCATCAAAAATGCATCAGCAGCGGTTATCGACCTCTCTGTGAAATTCGAGGG
ACGCACCAAAGCAGAGTTTGTAATGACTGCTGCTTGGGCTTGGGCACCCACTGCTCCCCCGACAACAACAGTTGCAAAGCG
TTCTGCTCTTCCTGAAATCAATTCCCGCCCAGCACCCACTGCTCCCCCGACAACAACAGTTGCAGGTA
TGTCTAGTTGGGAAGGTCTCCATGCCTCCAGTACCAGTCACCAACTTCCATGAAGCACTTAAATACGA
CCCAATTCTTCTGTGAGGGCCCAGCTAAGTTTCGGCGAGACATGTCAACATGGCGCCACCGTGTCCC
TGAAGGGTGAAATGGAACAAAGCCACANGAGAAAAGAATCAATTGCCAATAGCCCAATGGCTAAGCTG
TGCAAGTCTCAGATGAATATGAAGAATCACCTTCTGCCAGCCTGCGTAACGTTACTCAAGCAGCTAA
CAATCTTGACCATTATCAAGATTATGTTTAACAACATTCCGGATGTTCTGAAGAACGGCACAT
ACAAGGTGTACAGTTTGGCACGTCGTTGGCTATATCCTTACGTGACGGAGAATATCTATCCTCAAAAC
CCAGTAAAAGATGCAGTACATATCATTGTCGATATCAACGAAGAAAGCACTGCTCTCAATGTGACAAT
GGAAACACCAGCCATGAACATCACCGACGNTTGAACATTCACCGACGTTCGCCTGAAACCTTGTGCACAGGCACTTTTA
ACATGAACCCGGCCCACAGTTGTAGAGCGCCAATACGTTTGATAATATAACTTACCCTATGGACCTTGGCAA
ACTTGCGTCGTTGACAGTACAATGCCAATACGTTTGATAATATAACTTACCCTATGGACCTTGGCAA
ATGCTGGCACGTTATGATGATGGTTGTTCCGAAACGTCCAGCAGACCTCTCTCAGCAACACTCATCGC
AACGTGCACAAGAAAGCCTGAGCACACTTGAAGAAGTGTCGTTTTGGTGAAGGAAGTTGGTAACAAC
AAGGNAAGTTATGGTGATGACGAATTCAGCCACATCAGCAAGCCTGTTCAGAAGCCTGCTCCATTCTAACTCTG
ACCAAACGGTTTGGTCCACCATAAAAACGACAAGCCTGTTCAGAAGCCTGTCACTATACCCTCAC
CCNCTACAACAACGAAGGCAACCTGCTGGCCCAAGTTCACGAACTGCCAGAAGGTGCACTATACCTCAC
GTTTCCAAACAAAAGCTTGGTGATCATCTACGACGGAGTGAGGGTTATGCTGCAGGCTAGCAACGAAT
ACCGCCAACAAATTAGAGGTCTCTGTGGAAATATGGATGGAGAACCCTTCAATGATTTCATGACGCCA
AGTAACTGCCTCATTAGGAACCACCATCCATTTTTACTGCCACTTATGCAATGCATGAAGAATCATGCCA
ACGACCAGCAAAGATTAGGAACAAATCAGGAAAGAAGCATGTGTTCAGGAAAAGATTAGTTCGCAG
ATGTTATTCCTAATGCTAAGCCAAAAAGTGCTCGCCTAAGAGATTCCNAACTCATTCCTCATTCCGAAATC
TAACCCAGACATCATCTCTTCTTCCTCCTCCTCCCTCCTCCTCCTCTTTCCTCTTCCATCCTCATCATCATC
ATCATCCTCATCATCATCATCACATCGTCCTCCTCCTCCTCCTCCTCGANCCCAACTTCCAANTTCAAG
CTTCANGTTTCCAGTTTCTNGAAATCAAATGAAATNTTCGGAAA

FIGURE 22F

USE OF RNA INTERFERENCE TO VALIDATE NEW TERMITICIDE TARGET SITES AND A METHOD OF TERMITE CONTROL

This invention claims the benefit of priority to U.S. Provisional Patent Application Ser. No. 60/991,959 filed Dec. 3, 2007.

This invention was made with government support under Soldier Derived Semiochemicals in Termites Temple for Prototype Termiticides That Act Via Caste-Disruptor, contract number 2007-35607-1777, awarded by the USDA-CSREES-NRL. The government has certain rights in the invention.

FIELD OF THE INVENTION

The present invention relates to termite control, and in particular to methods, bait matrix compositions and kits for increasing the mortality of termites (*R. flavipes*) and decreasing the viability of termite colonies utilizing RNA interference techniques to target new termiticide sites, such as the genes controlling cellulase activity, genes controlling hexamerin activity, and other specific genes that participate in hormone signaling during termite caste differentiation.

BACKGROUND OF THE INVENTION

Termites are considered to be one of the most important bioreactors on the planet. Termites have developed cellulose digestion capabilities that allow them to obtain energy and nutrition from nutritionally poor food sources, such as cellulose. Because of their roles in nutrient and carbon cycling in natural ecosystems, termites are insects with tremendous positive global value. However, because of their cellulose feeding/digestion capabilities termites are also globally important as economic pests. As a result of their damage to human structures and commodities, it has recently been estimated that annual termite damage, control and repair costs exceed $20 billion worldwide.

Subterranean termites from the genera *Reticulitermes* and *Coptotermes* are among the most destructive species worldwide. In particular, the U.S. Eastern subterranean termite *R. flavipes* and its European synonym *R. santonensis* are among the most important pest termites on their respective continents. Millions of gallons of soil termiticides are applied every year in the US and Europe to protect from subterranean termite damage. A more environmentally-friendly method of termite control is through baiting, which involves recruiting termites to feed on cellulosic substrates impregnated with low concentrations of slow-acting chemical insecticides. A major drawback to baiting, however, is its lack of speed in termite colony elimination. In order to reduce reliance on non-specific soil termiticides and increase speed of colony elimination through baiting, there is a need for effective, faster-acting termite bait active ingredients. The instant invention provides a significant new method of termite control utilizing RNA interference techniques.

The cellulases are a family of enzymes that hydrolyze the beta 1,4, linkages of cellulose and permit this conversion of cellulose into energy sources. They appear to have endogenous cellulases, as well as celluloses that arise from symbionts that live in the termites' guts. The biologically mediated degradation of cellulose requires several functional types of cellulases, mainly endoglucanases that act on longer cellulose chains, and exoglucanases and beta glucosidases.

Prior research has identified various genes in the termite *R. flavipes* called Cell-1,2,3, and 4 that code for cellulases. Cell 1 and Cell 2 are endoglucanases, while Cell 3 and Cell 4 are exoglucanases.

Good to excellent inhibition of exoglucanases and beta glucosidase activity has been observed in in vitro enzyme assays, however, the inhibitors cellobioimidazole (CBI) and fluromethyl cellobiose (FMCB) caused only moderate termite mortality in bioassays. This lack of toxicity suggests that other upstream enzymes that act on longer cellulose chains may be more susceptible target sites for novel cellulase inhibitors, and thus in the instant invention, using RNA interference to create endoglucanase inhibition is addressed as a means for termite population control.

Termites are the only social insect group that undergoes incomplete metamorphosis. Worker termites may differentiate into reproductive or soldier termites, with resultant different behaviors. Worker termites engage in foraging, tunneling and brood tending, the reproductives produce offspring, and the soldiers engage in colony defense. Hexamerin proteins are part of a mechanism that maintains high worker proportions in termite colonies. This mechanism allows termite colonies to retain high proportions of altruistic worker members, such proportion apparently enhancing colony fitness. The morphogenesis of workers to pre-solider and soldier termites (see FIG. 1 and FIG. 5*a*) is induced by a 2-5 fold increase of the insect juvenile hormone (JH). Hexamerin proteins have well defined roles as JH binding proteins.

Using RNA interference techniques the instant invention demonstrates that silencing the Hex-1 and Hex-2 hexamerin genes increases pre-soldier formation and can be utilized as a means of decreasing the proportion of worker termites in the colony and consequently negatively impacting termite colony fitness. Additionally, targeting other genes that are part of juvenile hormone (JH) signaling is another aspect of the instant invention. Here, genes include the BTP/POZ transcriptional regulator "broad", the "farnesoic acid methyl transferase-2" gene which encodes an enzyme that is part of the JH biosynthetic pathway, two genes encoding cytochrome P450 enzymes named "Cyp15-1" and "Cyp15-2" that participate in JH biosynthesis and degradation, and two genes encoding vitellogenin proteins that dramatically increase in expression during JH-dependent caste differentiation.

With the ever-pressing demand for termite control compositions that are environmentally safe and effective in preventing termite infestation, researchers are pursuing a number of strategies to overcome problems of prior compositions.

Among the various methods and uses of RNA interference reported in the patent literature are the following.

U.S. Patent Publication 2007/0199100 to Michaeli; Shulamit, et al., shows feeding on plant cytoplasm, including insects, nematodes and fungi, plants engineered to produce small interfering RNAs (siRNAs) capable of silencing parasite specific gene; parasite gene is stage-specific gene, gene involved in essential, early developmental stages of parasite, the plant; uses T7 polymerase recognition sites [0232]; [primers used at the 5'end of gene [0247]; per amplification [0249].

U.S. Patent Publication 2007/0192903 to Heck; Gregory, et al., shows transgenic plant cells, plants and seeds containing modified suppression elements, and useful derivatives of transgenic plant cells, plants/seeds, such as food/feed products; suppression elements any suppression element that when transcribed in eukaryotic cell, results in silencing the target gene; suppression element can be transcribable DNA of any length & 19 to 27 nucleotides (for example 19, 20, 21, 22, 23, or 24 nucleotides) for every target gene suppressed, [0025] and may include siRNA [0034]; plant cells, [0045]; silenced during transcription [0062]; suppression measured by resistance to pest [0064]; 100 base pair fragment amplified by PCR with appropriate primers to produce an antisense template and sense template; sense and antisense reactions mixed, heated to 75 degrees Celsius, cool to room temperature; resulting in annealed 100 base pair double-stranded RNA product; purified with e MEGAscript™ RNAi Kit (Ambion, CAT #1626); produce a 100 base pair dsRNA product; tested with same WCR larval bioassay; fed to WCR larvae at 0.2 ppm, 100 bp dsRNA suppression element induced 100% mortality (FIG. 1); control (double-stranded RNA derived from 108 base pairs of vector sequence) caused no mortality at same feeding concentration [0108].

U.S. Patent Publication No. 2007/0130653 to Baulcombe; David, et al., shows siRNA, coexpressed in cells at appropriate developmental stage provide silencing of final target; final target may be a gene in a second organism, such as a plant pest, that feeds upon the organism containing the chimeric gene or genes.

U.S. Patent Publication 2007/0011775 to Allen; Edwards, et al., shows dsRNA for silencing genes [0008]; aptamer binds to tissue/cell/cell component such as gut of a pest of plant in which RNA is transcribed [0110].

U.S. Patent Publication 2006/0288448 to Abad; Andre R., et al., shows compositions of novel nucleic acid molecules; nucleotide sequences encoding modified insect protoxins provide for efficient processing into active toxins within the gut of the insect pest that feeds on plant host expressing modified insect protoxin; nucleotide sequences that encode modified insect protoxins that have proteolytic activation site engineered with cleavage site sensitive to insect gut protease; cleavage of modified insect protoxin by an insect gut protease produces an active insect toxin in the insect gut; [0015] express the gene from an inducible promotor, particularly from a pathogen-inducible promoter; promoters include those from pathogenesis-related proteins which are induced following infection; e.g. beta-1, 2-gluvanase, chitinase [0089].

U.S. Patent Publication 2006/0272049 to Waterhouse; Peter Michael, et al., shows genes expressed in cells of plant sap-sucking insect gut tissue/midgut are targeted; genes involved in gut cell metabolism/growth/differentiation [0067].

U.S. Patent Publication 2004/0133943 to Plaetinck; Geert, et al., shows alleviating pest infestation of plants, when the pest feeds on plants it will digest expressed dsRNA in plant inhibiting expression of DNA within pest which is critical for its growth, survival, proliferation or reproduction [016]; root will produce RNA/dsRNA from introduced piece of DNA when root specific promoter is utilized; nematode feeds on plant, RNA and/or dsRNA will be consumed or ingested by the nematode; RNA and/or dsRNA can enter the cells of the nematode and perform its inhibitory action on the target DNA1 nature of cloned DNA piece of worm, nematode and perform its inhibitory action on the target DNA; nature of cloned DNA piece of worm, nematode will not be able to survive, to eat, proliferate, preventing the animal of feeding longer on the plant, and thus protecting the plant [0124]; T7 polymerase encoding with PCR, [0127], RNAi phenotype lines [0138].

U.S. Patent Publication 2004/0098761 to Trick; Harold N., et al., shows transgenic plant expressing a heterologous double stranded nematode RNA sequence at level such that nematodes ingesting said heterologous double stranded nematode RNA sequences exhibit decreased proliferation as compared to nematodes feeding on non-transgenic plants [0012]; includes woody plants [0034]; uses RNAi [01116]; use of RNA interference (RNAi) down regulate expression of genes needed for nematode.

U.S. Patent Publication 2004/0018999 to Beach; David, et al., shows inhibition of cellulase by dsRNA [0129].

U.S. Patent Publication 2003/0154508 to Stevens; Bruce Russell, et al., shows control of termites [0044]; using double-stranded interfering RNA (RNAi), RNA-mediated interference (RNAa), [0051] to silence ligand-gated ion channels in the insect gut.

U.S. Patent Publication 2003/0150017 to Mesa; Jose Ramon Botella, et al., shows genetic agents are RNAi [0048]; Down-regulation of expression of target gene prevents/retards pathogen growth, development and/or reproduction [0047]; "pathogen" insect, arachnid or other creature capable of infecting or infesting plant [0122]; uses per [0041].

U.S. Patent Publication 2003/0135888 to Zhu; Tong, et al., shows confer insecticidal activity on plant by altering its sterol composition; sterols are obtained by insects from their diet and are used for hormone synthesis and membrane stability; alteration by expression of novel genes; a negative effect on insect growth and/or development; endow the plant with insecticidal activity; lipoxygenase [0350].

U.S. Patent Publication 2003/0106092 to Davis, Eric L., et al., shows nucleic acid construct; cyst and root knot nematode responsive promoter, Nicotiana Ntcel7 (endoglucanase) promoter associated with heterologous nucleic acid segment that encodes a product disruptive of nematode attack.

U.S. Pat. No. 6,506,559 to Fire, Andrew, et al. describes gene-specific inhibition of gene expression by double-stranded ribonucleic acid dsRNA; target gene may be endoglucanase.

Thus, there are several inventions that relate to transgenic plants that express double strand RNA for insect or pathogen control. Only one of the applications (Stevens et al.) relates to using RNA interference (RNAi) for termite control, but at a different target site than the current invention. Andrew Fire et al. discusses RNAi-based pest control, but does not mention invertebrate control by feeding, nor does it teach invertebrate pest control by RNAi interference or double strand RNA (dsRNA) feeding.

The present invention provides a unique approach to controlling termite populations by using RNAi to increase termite mortality by inhibiting endoglucanases, hexamerins, "broad" BTB/POZ transcription factors, farnesoic acid methyl transferases, cytochrome P450s, and vitellogenins.

SUMMARY OF THE INVENTION

A first objective of the invention relates to a method of increasing termite mortality by administering dsRNA corresponding to endogenous lignocellulose enzyme-encoding genes or endosymbiotic lignocellulase enzyme-coding genes to the termites, including silencing the Cell-1 gene.

A second objective of the invention relates to a method of increasing termite mortality in vivo by inhibiting endoglucanases utilizing RNA interference technology (RNAi).

A third objective of the invention relates to a method of inhibiting cellulase activity in vivo utilizing RNAi technology.

A fourth objective of the invention relates to a method of inhibiting cellulase activity utilizing chemical inhibitors.

A fifth objective of the invention relates to inhibiting termite colony fitness by utilizing RNA interference techniques to silence broad BTB/POZ transcription factor, farnesoic acid methyl transferase, cytochrome P450, and vitellogenin genes.

A sixth objective of the invention relates to a kit containing dsRNA corresponding to Cell-1 genes for use in increasing termite mortality.

A seventh objective of the invention relates to a kit containing dsRNA corresponding to broad BTB/POZ transcription factor, farnesoic acid methyl transferase, cytochrome P450, and vitellogenin genes for use in decreasing termite colony fitness.

An eighth objective of the invention relates to providing bait matrices that comprise ds RNA to one or more of Hex-1 and Hex-2, broad, farnesoic acid methyl transferase, cytochrome P450 and vitellogenin genes and natural juvenile hormones (JH), synthetic juvenile hormones and terpenes.

A ninth objective of the invention relates to inhibiting termite colony fitness by utilizing RNA interference techniques to silence broad BTB/POZ transcription factor, farnesoic acid methyl transferase, cytochrome P450, and vitellogenin genes.

A tenth objective of the invention relates to inhibiting termite colony fitness by utilizing RNA interference techniques to silence the Hex-1 and Hex-2 genes.

An eleventh objective of the invention provides bait matrix compositions comprising dsRNA corresponding to an endogenous lignocellulose enzyme-encoding gene or endosymbiotic lignocellulase enzyme-coding gene, and one or more of natural juvenile (JH) hormone, synthetic juvenile hormone, or terpenes.

Further objects and advantages of this invention will be apparent from the following detailed descriptions of presently preferred embodiments which are illustrated schematically in the accompanying drawings.

BRIEF DESCRIPTION OF THE FIGURES

FIGS. 7A and 7B shows genes not impacted in R. flavipes workers after feeding on Cell-1 endoglucanase-homologous dsRNA.

FIGS. 8A and 8B shows the impacts of Cell-1 endoglucanase gene silencing on downstream cellulase enzyme activities.

FIG. 15B discloses SEQ ID NOS 2-5, respectively, in order of appearance. FIG. 15D discloses SEQ ID NOS 6-9, respectively, in order of appearance.

FIG. 16 shows statistical comparisons of CT values between reference and targeted genes from Cell-1 dsRNA feeding bioassay.

FIG. 17 shows statistical comparisons of CT values between reference and targeted genes from Hex-1 and Hex-2 dsRNA feeding bioassay.

FIG. 18 shows termite gene identities. Forward primers disclosed as SEQ ID NOS 10-20, respectively, in order of appearance. Reverse primers disclosed as SEQ ID NOS 21-31, respectively, in order of appearance.

FIG. 19 shows Cell-1 gene sequences (SEQ ID NO: 32).

FIGS. 20A and 20B shows Hex-1 (SEQ ID NO: 33) and Hex-2 (SEQ ID NO: 34) gene sequences.

FIGS. 22A, 22B, 22C, 22D, 22E and 22F shows R. flavipes gene sequences for the JH-linked developmental genes broad (SEQ ID NO: 38), Farnesoic Acid Methyl Transferase-2 (SEQ ID NO: 37), Family 15 Cytochrome P450-1 (SEQ ID NO: 35) and -2 (SEQ ID NO: 36), and Vitellogenin-1 (SEQ ID NO: 39) and -2 (SEQ ID NO: 40).

DESCRIPTION OF THE PREFERRED EMBODIMENT

Before explaining the disclosed embodiment of the present invention in detail, it is to be understood that the invention is not limited in its application to the details of the particular arrangement shown since the invention is capable of other embodiments. Also, the terminology used herein is for the purpose of description and not of limitation.

All percentages, ratios and proportions used herein are by weight unless otherwise specified.

The instant invention exploits the phenomenon known as RNA interference (RNAi) to inhibit the function of the Cell-1 gene, previously identified as an endoglucanase gene in R. flavipes, and the Hex-1, Hex-2, broad, farnesoic acid methyl transferase-2, Cyp15-1 and -2, and vitellogenin-1 and -2 genes in R. flavipes, which participate in caste regulation/differentiation. In this fashion, increased termite mortality is achieved. This approach utilizes the ability of a double-stranded (ds) RNA to block expression of its corresponding single-stranded mRNA but not that of mRNAs with a different sequence. To use RNAi for intentional silencing of a gene of interest, applicants produce dsRNA based on the sequence of the gene to be inactivated. A 500 base pair fragment of the Cell-1 gene was amplified by PCR using primers that were appended on their 5' ends with T7-RNA-polymerase recognition sequences. The PCR product was gel purified using a commercial kit (Promega; Madison, Wis.) and utilized as a template for double stranded RNA synthesis using the Silencer™ kit. (Ambion, Austin, Tex.). Double stranded RNA (dsRNA) was purified using the same kit and then quantified by spectrophotometry and agarose electrophoresis. The resulting dsRNA was diluted to 650 ng/microliter and applied to penny-sized filter paper disks (3.14 cm2) at a concentration of 13 micrograms per disk. The treated paper disks were then placed into 5 cm tissue culture dishes along with 15 worker termites (*R. flavipes*) Every second day through the entire experiment, assay dishes received 20 microliters of water. Every eighth day, dishes received fresh filter papers and any termite mortality was recorded. Experimental treatments included either one dose of dsRNA applied on assay day 1 or three doses of dsRNA applied on days 1,8, and 16. Two types of control treatments were also assayed; one of water alone and one consisting of the RNA storage buffer provided in the Ambion kit.

Figure 1:
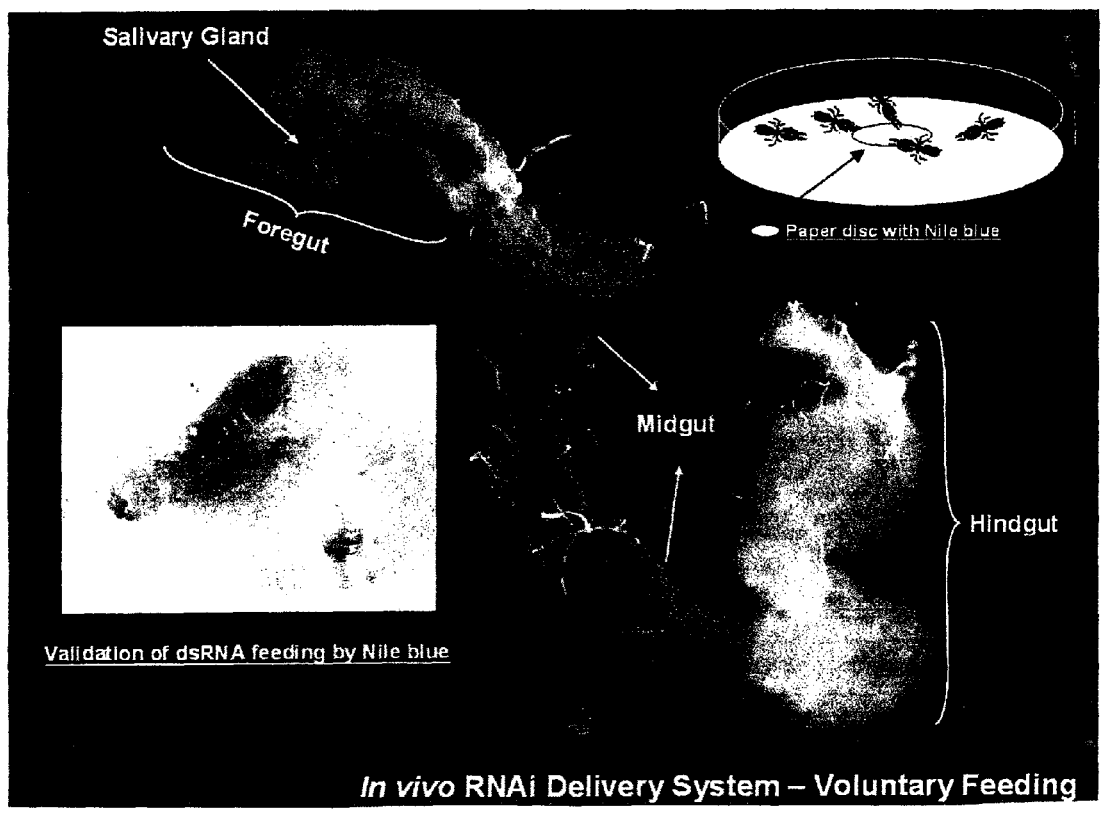
FIG. 1 shows voluntary dsRNA feeding by R. flavipes workers.
Figure 2A:
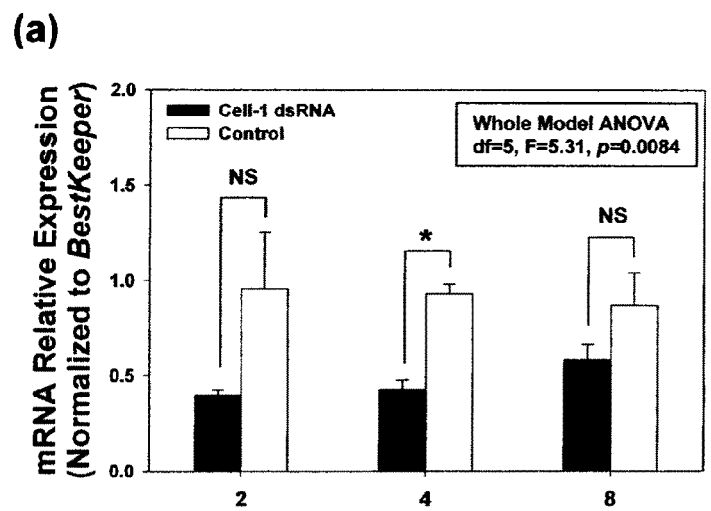
FIGS. 2A, 2B, 2C and 2D show sub-organismal and phenotypic effects displayed by R. flavipes workers after feeding on Cell-1 endoglucanase-homologous dsRNA.
Figure 2B:
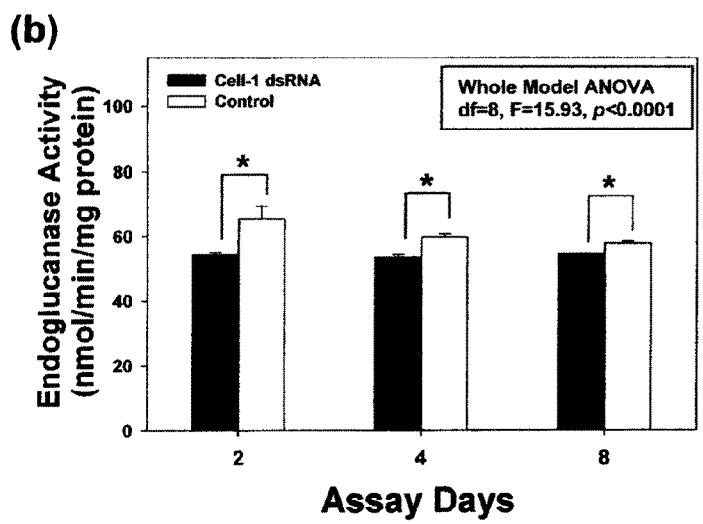
Figure 2C:
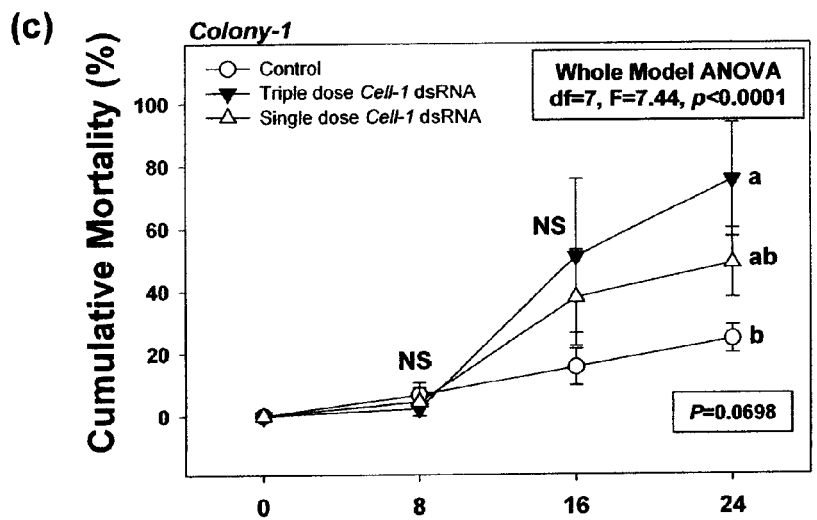
Figure 2D:
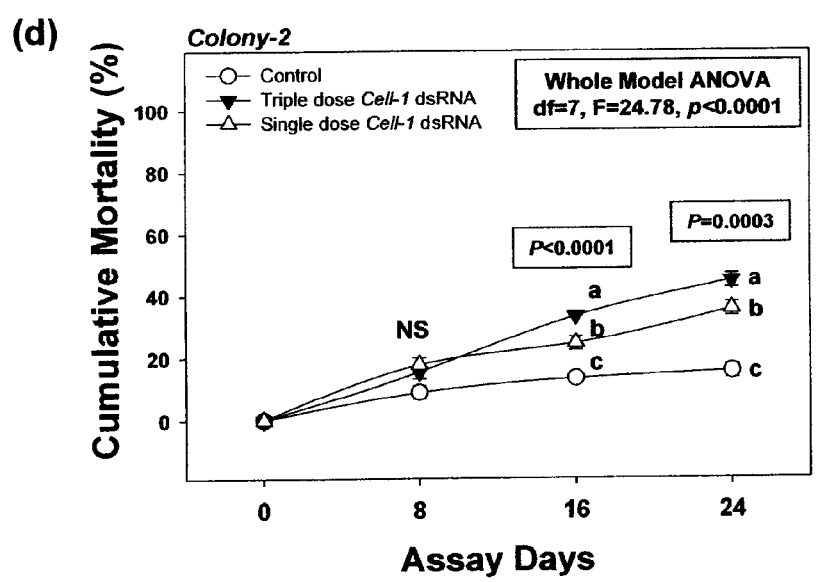

Feeding on dsRNA corresponding to the Cell-1 endoglucanase gene of *R. flavipes* resulted in a significant mortality relative to controls that included both water and ds RNA storage buffer (as shown in FIG. 1) In RNAi treatments, worker mortality increased through the 24 day assays. Additionally, greater mortality was observed in treatments that involved 3 dsRNA doses than in treatment s of a single dose. Because these results show greater mortality after endoglucanase silencing than observed previously with chemical exoglucanase and beta glucosidase inhibitors this suggests greater sensitivity of endoglucanases to novel cellulase inhibitors.

Also demonstrated was the fact that there was reduced mortality in a termite colony with larger body size. This reduced mortality was presumably a result of greater nutritional reserves. This finding suggests that smaller and or nutritionally stressed field colonies would be more susceptible to endoglucanase inhibitors. This same trend was observed for the two chemical inhibitors of exoglucanases and beta glucosidases previously described.

In addition to RNAi interference with endoglucanase activity, chemical inhibitors of endoglucanase may be designed. In particular, inhibitors with longer chains than CBI and FMCB are such inhibitors, as well as biose-DNP.

As regards the Hex-1, Hex-2, broad, farnesoic acid methyl transferase-2, Cyp 15-1 and -2, and vitellogenin-1 and -2 genes, dsRNA corresponding to the genes was obtained and administered to the termites in a similar fashion to the Cell-1 genes. As Hex-1 and Hex-2 are genes which determine the proper morphogenesis of the termites, silencing these genes decreases the fitness of the termite colonies and when applied in combination with developmental hormone treatments, leads to lethal morphological defects. As the broad, farnesoic acid methyl transferase-2, Cyp15-1 and -2, and vitellogenin-1 and -2 genes participate in JH signaling, silencing these genes decreases individual and colony fitness and when applied in combination with developmental hormone treatments, leads to a rapid onset of mortality.

Trophallactic exchange and exchange via external grooming of bait active ingredients from donor to recipient termites is necessary in order for this technology to be applied to termite baits which could be effective at eliminating termite colonies. Trophallaxis is defined as the transfer of food or other fluids among members of a social insect colony through mouth-to-mouth (stomodeal) or anus-to-mouth (proctodeal) feeding [Wilson, E. O. 1971. The Insect Societies. Belknap Press of Harvard Univ. Press, Cambridge, Mass. 548 pp.]. The invention demonstrates that ds RNA silencing the Cell-1, Hex- and Hex-2 genes can in fact be transferred from donors to naïve recipient termites. Bait matrices can be optimized as indicated in Example 1 below.

Example 1

Materials and Methods used in silencing Cell-1 and Hex-1, Hex-2, broad, farnesoic acid methyl transferase-2, Cyp15-1 and -2, and vitellogenin-1 and -2 genes.

Figures 15A, 15B:
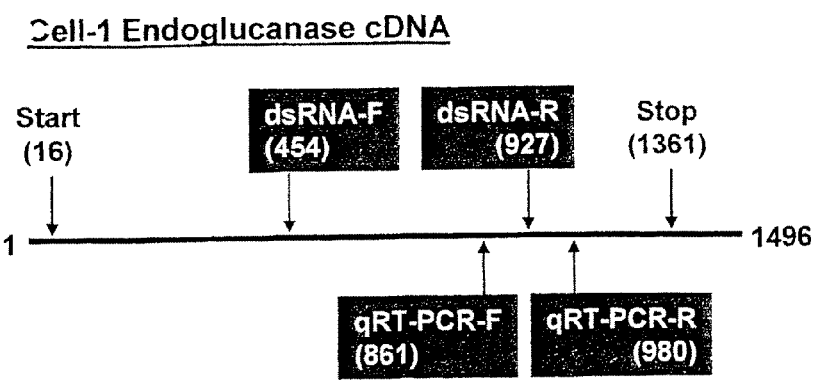
FIGS. 15A, 15B, 15C and 15D shows the positions of PCR primer sets used for amplifying dsRNA templates and quantitative real-time PCR [qRT-PCR], as well as their sequences.
Figures 15C, 15D:
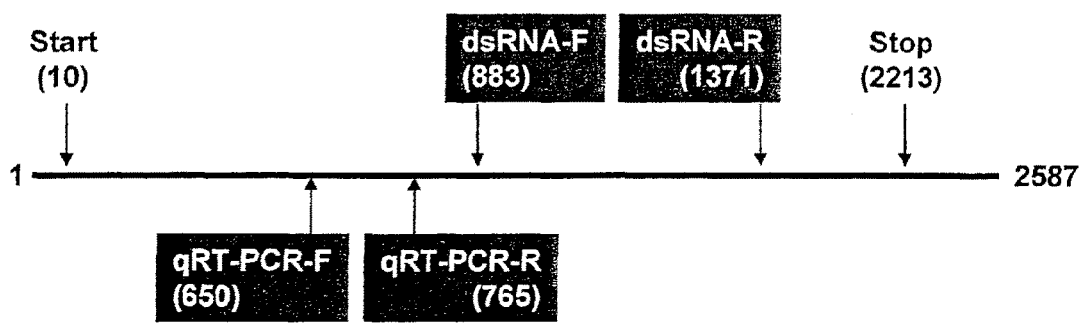

Termites. *R. flavipes* colonies were collected from Gainesville, Fla., during spring and summer 2006. Colonies were maintained in sealed plastic boxes (30×24×10 cm) in complete darkness (L:D=0:24), at 22±1° C. and 69±1% RH. Both colonies were maintained without soil for more than six months and provisioned with moist brown paper towels and pine wood shims. The two colonies were collected several miles apart, and are therefore believed to have a low degree of genetic relatedness. There were significant size differences between the two colonies (DF=60, F=11.0872, p<0.0001), with Coloy-2 showing greater mass and fat body proliferation. The average weight per termite for Colonies-1 and -2, respectively, were 2.66±0.005 mg (n=900) and 3.25±0.004 mg (n=900), respectively. The identity of colonies as *R. flavipes* was verified by a combination of soldier morphology and 16S-mt-rDNA gene sequence. Only worker termites were used in this study because of their totipotent nature (developmental plasticity) and lingo-cellulose digestion capability]. Termites were considered workers if they did not possess any sign of wing buds or distended abdomens, and had pronotal widths wider than mesonotal widths.

dsRNA synthesis and stability. FIG. 15 shows positions of PCR primer sets used for amplifying dsRNA templates from the target genes Cell-1 and Hex-2 and their sequences. FIGS. 22-22F shows the positions of PCR primer sets used for amplifying dsRNA templates from the target genes broad, farnesoic acid methyl transferase-2, Cyp15-1 and -2, and vitellogenin-1 and -2. PCR primers used for dsRNA template amplification had T7 RNA polymerase recognition sequences appended onto their 5' ends (5'-TAATACGACTCACTATAGGG-3') (SEQ ID NO: 1). dsRNA was synthesized using a commercially available kit (Silencer™, Ambion, Austin, Tex.). The possibility of non-target effects was minimized by designing siRNAs with virtually no sequence similarity to ~5,000 known genes/ESTs from *R. flavipes*. dsRNA templates corresponded to non-homologous, ~500 bp portions from the open reading frames of all target genes (see FIGS. 15 and 22). For stability assays, Cell-1 dsRNAs (50 ml) were stored in non-sterile 0.6 ml microcentrifuge tubes at room temperature (~25° C.) for a period of 24 days. At days 0, 0.5, 1, 2, 3, 4, 5, 6, 7, 8, 16, and 24, 1.0 ml of Cell-1 dsRNA was removed and transferred to a microcentrifuge tube containing 9 ml of dsRNA solvent and then stored at −20° C. After 24 days, frozen samples were thawed concurrently, subjected to agarose gel electrophoresis, and compared to a standard curve of 0-128 ng of fresh Cell-1 dsRNA. Three independent replicates were performed with a single gel per replicate.

dsRNA Feeding bioassays. dsRNA-mediated gene silencing was accomplished using voluntary feeding bioassays. Termites were pre-starved for 12 h to standardize their hunger status before the assay. The bioassay was run by placing groups of 15 worker termites into 35-mm tissue culture dishes that contained 18 mm diam. treated paper towel disks. Multiple and single dose dsRNA regimes were tested. All assays were carried out for 24-d. Paper disk moisture was monitored every other day. Every 8th day, old paper disks were replaced with new ones. These new paper disks were treated exactly the same as previous ones. Feeding (mg/dish) was determined by comparing weights of paper disks before and after confinement with termites, whereas body weight (mg/termite) was measured by comparing termite weights before and after 8-day paper consumption and then by correcting for the number of live termites at the time of sampling. Paper disks were dried in a drying oven before weighing. Mortality, paper consumption, body weight change, and/or presoldier formation were documented every 8th day. The complete experimental design included two colonies (Colony-1 and -2), with three replicate dishes per treatment per colony.

For Cell-1 dsRNA feeding bioassays, the experimental design included two treatments (triple and single dose Cell-1 dsRNA) and a control (3 doses of dsRNA buffer; Ambion; Austin, Tex.). Paper disks were treated with either 20-ml of dsRNA buffer containing 13 mg of Cell-1 dsRNA, or the same volume of dsRNA buffer (Ambion) alone for untreated controls. Mortality, feeding (mg/dish), and body weight (mg/termite) were documented every 8th day throughout the Cell-1 feeding bioassays. For Hex-2 dsRNA feeding bioassays, the experimental design included five treatments (triple dose JH, triple dose Hex-2, triple dose JH+Hex-2, single dose Hex-2, single dose JH+Hex-2), and a control (triple dose dsRNA buffer; Ambion). Paper disks were treated first with either 20 ml acetone containing 150 mg JH III, or 20 ml acetone for untreated controls. JH III was purchased from Sigma Chemical (93% purity; St. Louis, Mo.) and diluted in analytical grade acetone (>99% purity; Sigma). After acetone treatment, paper disks were allowed to dry for 30 min in a fume hood. After papers dried, the second round of treatments with dsRNA solution were made, which contained either 5.5 mg of Hex-2 dsRNA in 20 ml dsRNA buffer, or 20 ml dsRNA buffer alone for untreated controls. Mortality, feeding (mg/dish), body weight (mg/termite), and presoldier formation were documented every 8th day throughout the Hex-2 feeding bioassays.

Bait matrix. Feeding may be enhanced by utilizing cellulose substrates in bait matrices including paper (eg, paper towel, newspaper, cardboard), wood (eg, pine, poplar, balsam fir), and compressed cellulose composites (eg, saw dust, agricultural wastes, recycled paper, etc.).

Feeding stimulants may also be added to the matrix, including cellulase inhibitors, sugars (mono-, di-, and polysaccharides), hydroquinone, lignin polymers, mono-lignols, and phenolic lignin by-products.

To enhance caste differentiation with hexamerin, farnesoic acid methyl transferase-2, Cyp15-1 and -2, and vitellogenin-1 and -2 silencing, natural juvenile hormone (JH) homologs, synthetic JH analogs and various terpenes can also be included in a bait matrix. Natural JH homologs include JH 0, JH I, JH II, and JH III. Synthetic JH analogs include methoprene, fenoxycarb, hydroprene, kinoprene, pyriproxyfen, juvenogens, and paper factor. Terpenes that could be added include soldier-termite-derived semiochemicals such as cadinene, cadinene-aldehyde, thujopsene, thujone, gurjunene, nerolidol, farnesol, nootkatone, E-beta-farnesene, geranyl geraniol, humulene, limonene, linalool, geranyl linalool, alpha-pinene, and beta-pinene.

Validation of RNAi sub-organismal effects. Based on previous experiments RNAi-mediated gene silencing in termites fully recovers by 8-d after a single injected dose. Therefore, gene silencing validation bioassays were conducted here for one full feeding cycle, which lasted 8 days. Three replicated groups of 15 workers from a single colony were tested per treatment replicate. The bioassay procedures were exactly the same as described above. Destructive samplings started at day 0 (colony workers), and continued at assay days 2, 4 and 8. At the time of sampling, the 15 termite workers from each dish were divided roughly in half and stored at either −80° C. for transcriptional validation by qRT-PCR, or at −20° C. for protein-level validation by enzyme assays or SDS-PAGE.

Quantitative real-time PCR (qRT-PCR). FIG. 15 shows positions of qRT-PCR primers in the target genes Cell-1 and Hex-2, as well as their sequences. FIG. 18 shows all RT-PCR primer sequences for target and control genes, as well as provides accession numbers for all genes. qRT-PCR was performed using an iCycler iQ real-time PCR detection system with iQ™ SYBR® Green Supermix (Bio-Rad, Hercules, Calif.). cDNA, which served as the template for qRT-PCR, was synthesized from the total RNA of five each of individuals at 24-hr after injection. Total RNA and cDNA were obtained using the SV total RNA Isolation System (Promega, Madison, Wis.) and the iScript™ cDNA Synthesis Kit (Bio-Rad), respectively, following manufacturer protocols. The suitability of the three reference/control genes b-actin, HSP-70 and NADH-dh were evaluated using the two software packages Bestkeeper (Pfaffl et al. 2004) and NormFinder (Anderson et al. 2004). Both programs were developed to find the least variable reference genes for the purpose of providing accurate and reliable normalization of qRT-PCR data (Huggett et al. 2005). We used these programs to not only evaluate potential reference genes, but also to assess the effects of RNAi on target genes. Relative expression levels for specific genes, in relation to the most reliable reference gene (b-actin), were calculated by the 2-DDCT method (Livak & Schmittgen 2001).

Cellulase enzyme activity assays. After Cell-1 dsRNA feeding assays, termites stored at −20° C. were homogenized using a motorized Teflon-glass tissue homogenizer in 0.1 M sodium acetate (pH 5.8). This buffer was used in tissue preparations and enzyme assays. Whole-body homogenates were centrifuged at 14,000 rpm at 4° C. for 15 min. In order to remove excess lipids, the clear supernatant from each sample was removed carefully, avoiding the lipid layer and placed into new microcentrifuge tubes. The supernatant was used as an enzyme source in the cellulase assays described below. To estimate the protein concentration for each sample a bicinchoninic acid assay was used with bovine serum albumin as a standard. To measure endoglucanase, exoglucanase, and β-glucosidase activity, the model substrates used included carboxy-methyl cellulose (CMC), p-nitrophenol cellobioside (pNPC), and p-nitrophenol glucopyranoside (pNPG), respectively. All three substrates were diluted in homogenization buffer. The final substrate concentration used for the CMC-based endoglucanase assays was 0.5% (w/v), while a 4 mM substrate concentration was used for the pNPC and pNPG assays. The protocol for endoglucanase, exoglucanase, and β-glucosidase assays was modified from Han et al. J. Biol Chem 270:26012 (1995) and optimized for a COStar® 96-well microtiter plate (Corning Inc.; Corning, N.Y.) and a microplate spectrophotometer. Other conditions such as protein and substrate concentration, assay time, and buffer pH were optimized according to Zhou et al. (2008).

All three assays were carried out by placing 10 µl of enzyme extract and 90 µl of buffer+substrate in each sample well. CMC-endoglucanase assays are endpoint assays in which the microtiter plate was placed in an incubator at 32° C. for a total assay time of 30 minutes. The reaction was stopped by adding 100 µl of 1% 3, 5-dinitrosalicylic acid (DNSA), 30% sodium potassium tartrate, and 0.4 M sodium hydroxide to each sample well. To stop any remaining enzymatic activity, the microtiter plate was placed in a 95° C. water bath for 10 minutes and then cooled on ice for 15 minutes to allow color formation. The plate was read at 520 nm using the endpoint setting.

The absorbance readings, relative to a glucose standard curve, were used to calculate the specific activity. pNPC (exoglucanase) and pNPG β-glucosidase) assays are kinetic assays which measure the release of p-nitrophenol. These assays were carried out by allowing the enzyme and buffer+substrate mixtures to react for 20 minutes at 32° C. before being read at 420 nm, at room temperature. pNPC assays were read every 2 min for a total of 1.5 h, while pNPG assays were read every 2 min for 1 h. The mean velocity results from pNPC and pNPG assays were used to estimate specific activity. For each cellulase assay, activity was estimated from three reactions per treatment per experimental replicate.

Protein electrophoresis and densitometry. SDS-polyacrylamide gel electrophoresis (PAGE) was conducted as described in Scharf et al Insect Mol. Biol 14:31-44 (2005). PAGE resolving gels contained 8% acrylamide and 10% SDS. Stacking gels contained a lesser quantity of acrylamide (4%) and the same amount of SDS. A discontinuous Tris-Glycine buffering system was used, and protein sample buffer contained β-mercapto-ethanol as a sulfhydryl reducing agent. 15 mg of protein was loaded per lane. Each gel was run with in-gel BSA protein standards at concentrations ranging from 0.3125 to 10.0 mg per lane.

The BSA standards were used for densitometric quantification of hexamerin proteins directly on each gel. Molecular weight markers were Kaleidoscope™ broad-range markers (Bio-Rad; Hercules, Calif., USA). After running, gels were stained 1.0 hr in GelCode® Blue stain reagent (Pierce; Rockford, Ill.), then destained ~0.5-hr in several rinses of nanopure water. Gels were photographed using a Chemi-Doc imaging system (Bio-Rad). Gel images were densitometrically analyzed using Quantity-One™ software (Bio-Rad). Three independent Hex-2 dsRNA feeding assay replicates were performed with a single gel per replicate.

Photography. Termites were preserved in 95% ethanol before photographing using a JVC KY-F70B digital camera, Leica MZ12.5 stereomicroscope, and Auto-Montage Pro version 5.02 imaging software (Syncroscopy Inc.; Frederick, Md.).

Statistical analyses. Statistical analyses were carried out using JMP 7 software (SAS Institute; Cary, N.C.). Homogeneity of variances and normality of data distributions were examined by the Leven Test ($P<0.05$) and Shapiro-Wilk W Test ($P<0.05$), respectively. If data met the assumptions for analysis of variance (ANOVA), then means were separated by the Student's t-test (unless stated otherwise, two-tailed paired t-test were used at $P<0.05$). If data did not meet ANOVA assumptions, a nonparametric procedure was used to compare the means (Wilcoxon Rank Sums/Kruskal-Wallis Test; $P<0.05$).

Example 2

Transfer of RNAi Effects from Donor to Recipient Termites dsRNA corresponding to an internal 500 base pair fragment of the Hex-2 gene was prepared as described under "description of the preferred embodiment". Approximately 15 μg of Hex-2 dsRNA was applied in 50 μL nanopure water to a penny-sized (14 cm²) paper disk, followed by 20 μL of deionized water containing 0.05% Nile Blue dye. The disk was placed in a 5 cm tissue culture dish and 25 worker termites were added. The dish was placed in a growth chamber at 60% relative humidity and 27 deg. C. for 48 hr. to allow the termites to acquire dsRNA. These termites are referred as "donor" termites.

After 48 hr. the donor termites were placed in identical assay dishes with moist paper and variable numbers of naive "recipient" termite workers. 15 total termites were added per dish. Three donor-recipient ratios were tested (1:14, 2:13, and 5:10). Controls contained 15 naive workers only. Assays ran for a total of 28 days with mortality and any caste differentiation effects being scored every $4^{th}$ day.

Figure 21:
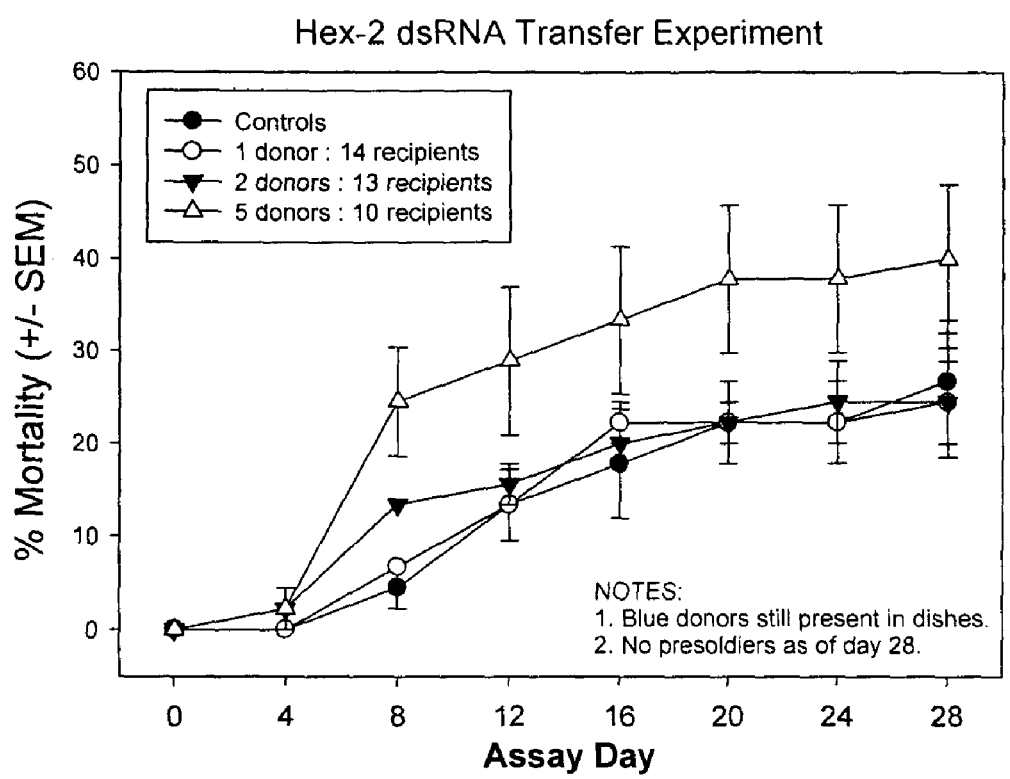
FIG. 21 provides a Hex-2 dsRNA transfer experiment demonstrating the transfer of RNAi effects from donor to recipient termites.

Within 3 hours, the guts of all donor termites showed evidence of blue dye, indicating acquisition of dsRNA. After 48 hr, all donors showed prominent whole-body blue coloration; a standard effect of Nile Blue dye. Through the 28 day donor-recipient assays, no caste differentiation effects were observed. The only distinguishable effect was significantly increased mortality in the 5:10 donor-recipient treatments (FIG. 21). Also interestingly, blue donors were still alive in all assay replicates, indicating that the majority of mortality was in recipient termites.

Unlike previous assays where termites were held on dsRNA treated paper for entire assays (FIGS. 4A-4D and 5A-5C), donor-recipient assays did not result in morphological deformities or presoldier differentiation. The reasons for this are not known at the present time. The fact that only mortality was observed in the 5:10 (donor: recipient) assays suggests that developing presoldiers may have been selectively killed, as described previously for developing supplementary reproductive termites [Miyata H, Furuichi H, Kitade O, 2004, Entomological Science 7: 309-314]. This is an unanticipated, but nonetheless, a desirable effect. These results provide evidence that (1) dsRNA and/or RNAi impacts can be transferred from donor to recipient termites, and (2) significant colony mortality may result if ⅓ of the colony acquires dsRNA via feeding.

Example 3

Lethal Impacts of Combining dsRNAs for Hormone Signaling Genes with Juvenile Hormone Treatments Six additional developmental genes were targeted by combined dsRNA+JH III treatments: broad, farnesoic acid methyl transferase (FAMET-2), two family 15 cytochrome P450s (Cyp15-1, Cyp15-2), and two vitellogenin genes (Vit-1, Vit-2). dsRNAs corresponding to internal 500 base pair fragments of all six genes (see FIG. 22) were prepared as described under "description of the preferred embodiment". Twenty μg of dsRNA was applied in 50 μL nanopure water to a penny-sized (14 cm²) paper disk. The disk was placed in a 5 cm tissue culture dish and 15 worker termites were added. Assays ran for 25 days at 60% relative humidity and 27 degrees C., with water being replenished and mortality/presoldier formation scored every $5^{th}$ day.

LT50 and LT90 were determined from time-mortality data using probit analysis (SAS software; Cary, N.C.). In this context, the terms LT50 and LT90 refer to the estimated times at which 50% and 90% mortality occurs in response to the various RNAi treatments relative to JH III treatments alone (FIG. 23). Applying the six dsRNAs alone had no significant effects on survivorship. The LT50 and LT90 values for JH III alone were 34.5 and 65.7 days, respectively (as a result of fitness costs from elevated presoldier levels). Silencing of all genes in combination with JH III led to 1.5-2.1× significantly faster LT50s; whereas, silencing of four of the genes in combination with JH III led to 2.1-2.4× significantly faster LT90s [broad, FAMET-2, Cyp15-2 and Vit-1] as a result of lethal molting impacts. These results (FIG. 23) show significant lethal impacts when silencing the four developmental genes broad, FAMET-2, Cyp15-2 and Vit-1 in combination with JH III treatments. Additionally, these results (FIG. 23) further imply significant fitness impacts when silencing all six developmental genes in combination with JH III (because of significantly reduced LT50 is all treatments).

FIG. 1 shows voluntary dsRNA feeding by R. flavipes workers. Top right: a drawing depicting the feeding bioassay configuration. Assays took place in 3.5-cm tissue culture dishes with 15 worker termites per dish and a ~1.7 cm diam. paper disk as the dsRNA delivery mechanism. Paper disks were also treated with deionized water (~50 ml). In the case of feeding validation assays, disks were also treated with 50 ml of a solution of 0.5% w/v Nile blue dye in water. Bottom left: examples of worker termites after 2-3-hr of isolation with treated paper disks in bioassay dishes. Note the prominent gut staining that is visible through the cuticle. Center: a dissected worker termite gut after dsRNA+Nile feeding. The three gut regions are highlighted: foregut and salivary gland (top); midgut (middle); and hindgut (right). Note the intense staining of the midgut, which is the presumed site of dsRNA uptake.

FIGS. 2A-2D shows sub-organismal and phenotypic effects displayed by *R. flavipes* workers after feeding on Cell-1 endoglucanase-homologous dsRNA. (a) Cell-1 gene expression differences between dsRNA treatments and controls at assay days 2, 4 and 8. Results are normalized to the three reference genes (β-actin, NADH-dh and HSP-70 based on Bestkeeper analysis (see FIG. 16). Asterisks denote significant differences between treatments and controls within days, as determined using pairwise t-tests ($p<0.05$). Prior to t-tests, an ANOVA were performed on the whole data set to verify significance of the model statement (results shown in box). (b) Endoglucanase enzyme activity differences between dsRNA treatments and controls for whole-body protein preparations at assay days 2, 4 and 8. Asterisks denote significant differences between treatments and controls within days at $p<0.05$. Statistical analyses were performed as in (a) above. (c,d) Mortality in *R. flavipes* workers from two colonies through 24-d of Cell-1 dsRNA feeding. Assay treatments included untreated controls (o), single dose dsRNA treatments provided at day 0 (D), and triple dose dsRNA treatments provided at days 0, 8 and 16 (▼). Means within days with the same letter are not significantly different by Fisher LSD t-tests at p-values shown. Prior to conducting any t-tests, significant variation in the whole data set was first verified by ANOVA (results shown in boxes at top right of each graph). All error bars represent standard error of the mean, as determined from three independent replicates.

Figure 3A:
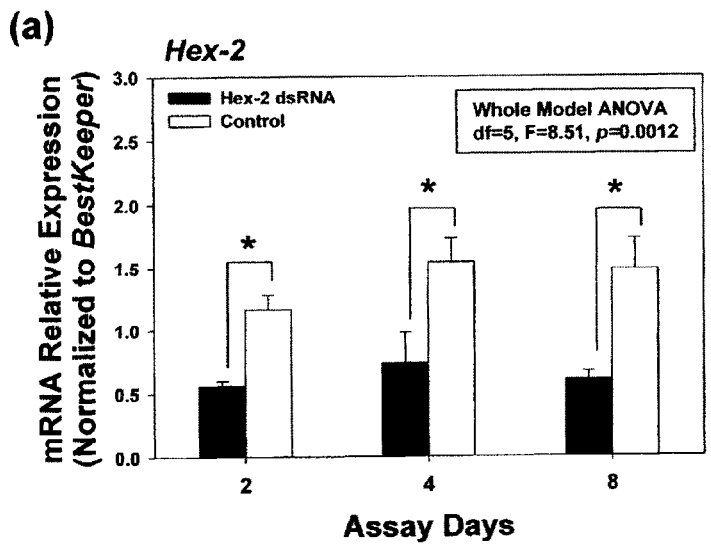
FIGS. 3A, 3B, 3C and 3D show sub-organismal effects in R. flavipes workers after feeding on Hex-2-homologous dsRNA.
Figure 3B:
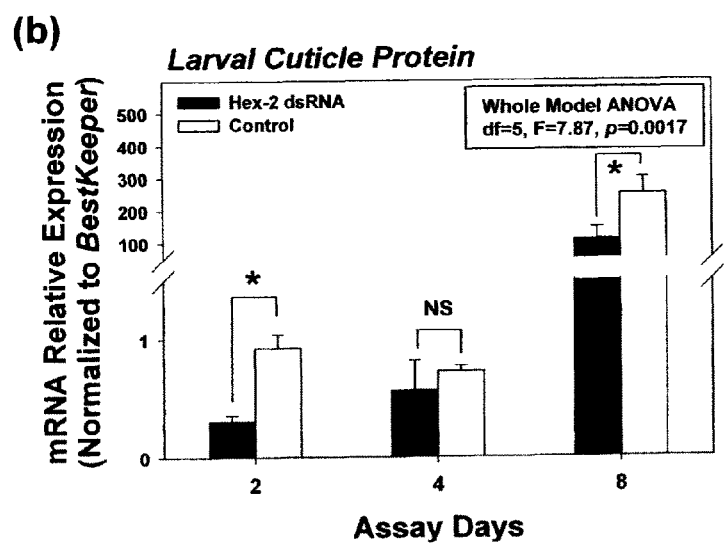
Figure 3C:
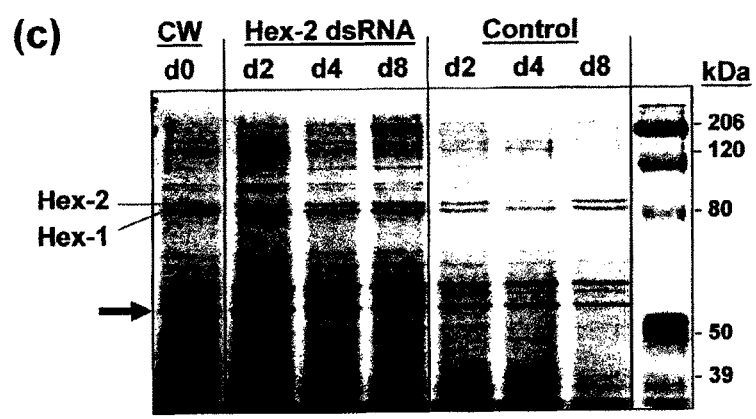
Figure 3D:
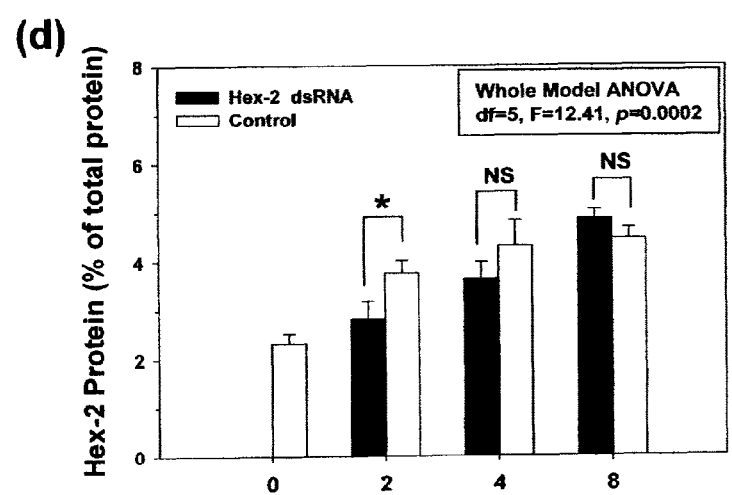

FIGS. 3A-3D shows sub-organismal effects in *R. flavipes* workers after feeding on Hex-2-homologous dsRNA. FIG. 3A Hex-2 gene expression differences between dsRNA treatments and controls at assay days 2, 4 and 8. Results are normalized to the three reference genes β-actin, NADH-dh and HSP-70 based on Bestkeeper analysis. Asterisks denote significant differences between treatments and controls within days, as determined using pairwise t-tests ($p<0.05$). Prior to t-tests, an ANOVA was performed on the whole data set to verify significance of the model statement (results shown in box). FIG. 3B shows downstream effects of Hex-2 silencing on the gene Larval Cuticle Protein, which encodes a factor critical to insect cuticle formation during the molting process. Asterisks denote significant differences between treatments and controls within days at $p<0.05$. Statistical analyses were performed as in FIG. 3A above. FIG. 3A shows a representative SDS polyacrylamide gel showing changes in hexamerin protein accumulation with and without 8-d of Hex-2 dsRNA feeding. Protein loadings were 15 mg per lane. The Hex-1 and -2 proteins occur as a doublet at around 80 kDa, with Hex-2 being the top band in the doublet. The arrow (") indicates a reference protein band used for normalization of densitometry results. Abbreviations: CW, colony workers; d, assay days (0, 2, 4 or 8); kDa, size of molecular mass markers in kilodaltons. FIG. 3D shows a densitometric analysis summary from three replicated SDS gels as shown in FIG. 3C above. Hex-2 quantities in mg were determined from in-gel standard curves of bovine serum albumin (not shown; see text for details). Asterisks denote significant differences between treatments and controls within days at $p<0.05$. Statistical analyses were performed as in FIG. 3A above. All error bars represent standard error of the mean, as determined from three independent replicates.

Figure 4A:
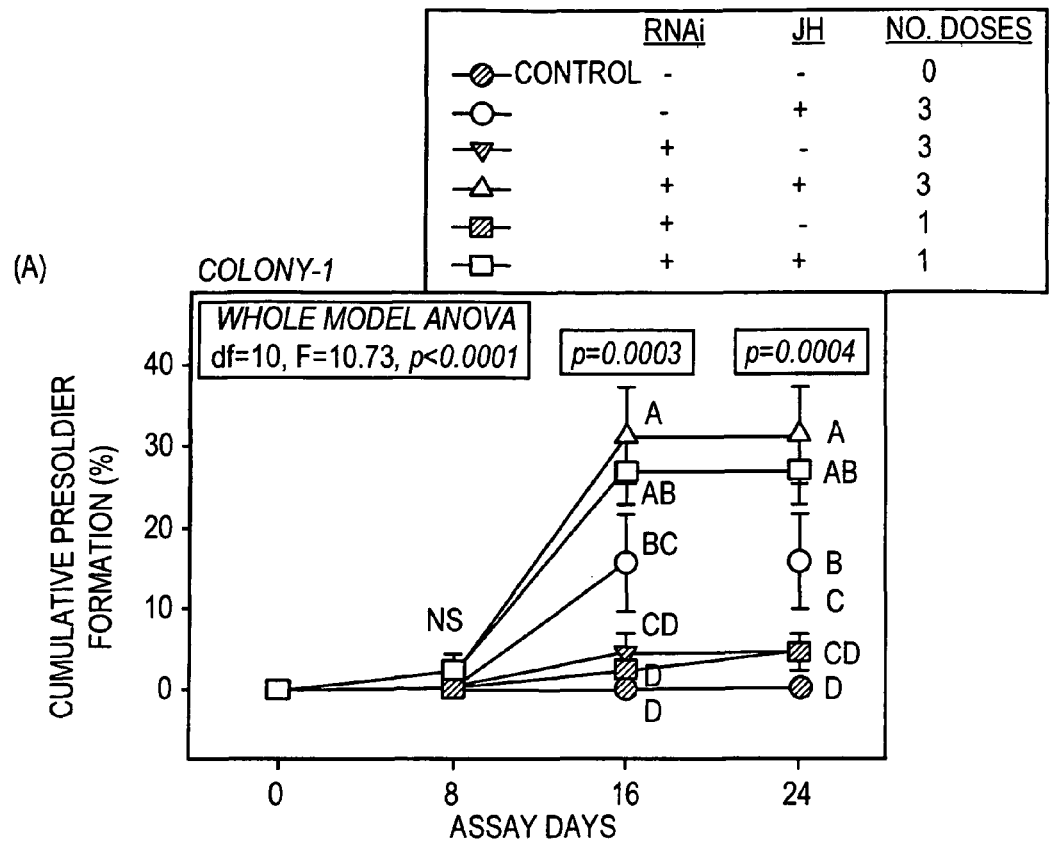
FIGS. 4A, 4B, 4C and 4D show phenotypic impacts displayed by R. flavipes workers after feeding on Hex-2-homologous dsRNA.
Figure 4B:
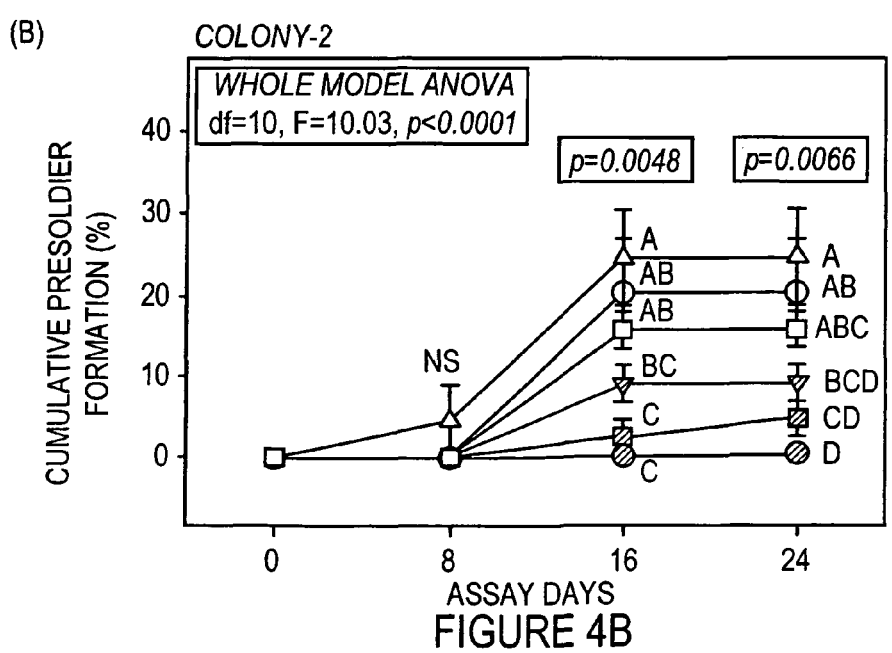
Figure 4C:
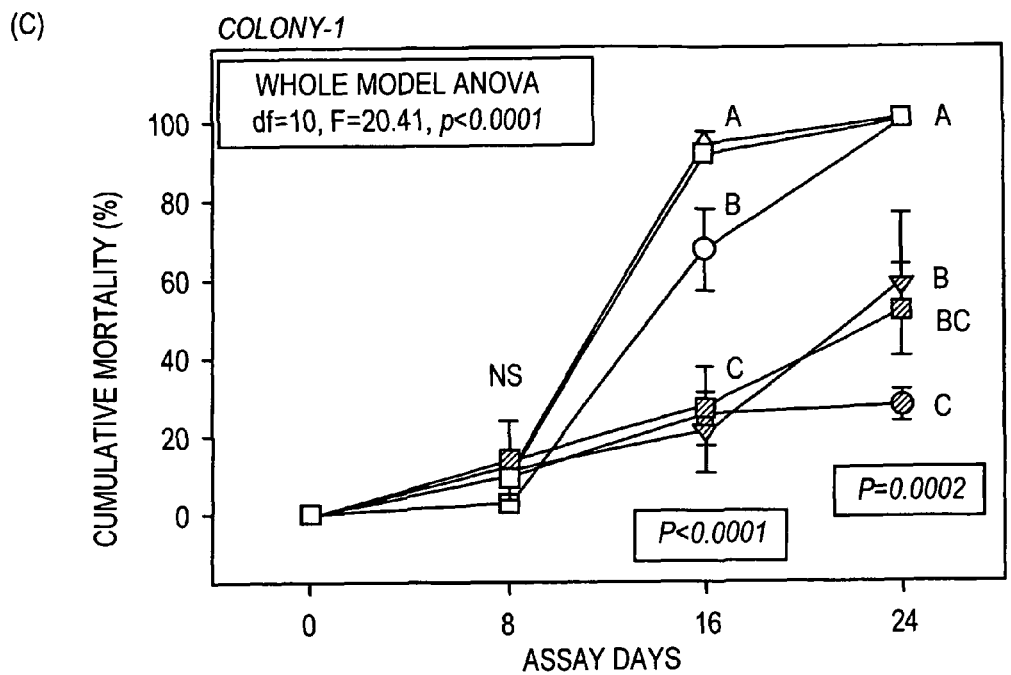
Figure 4D:
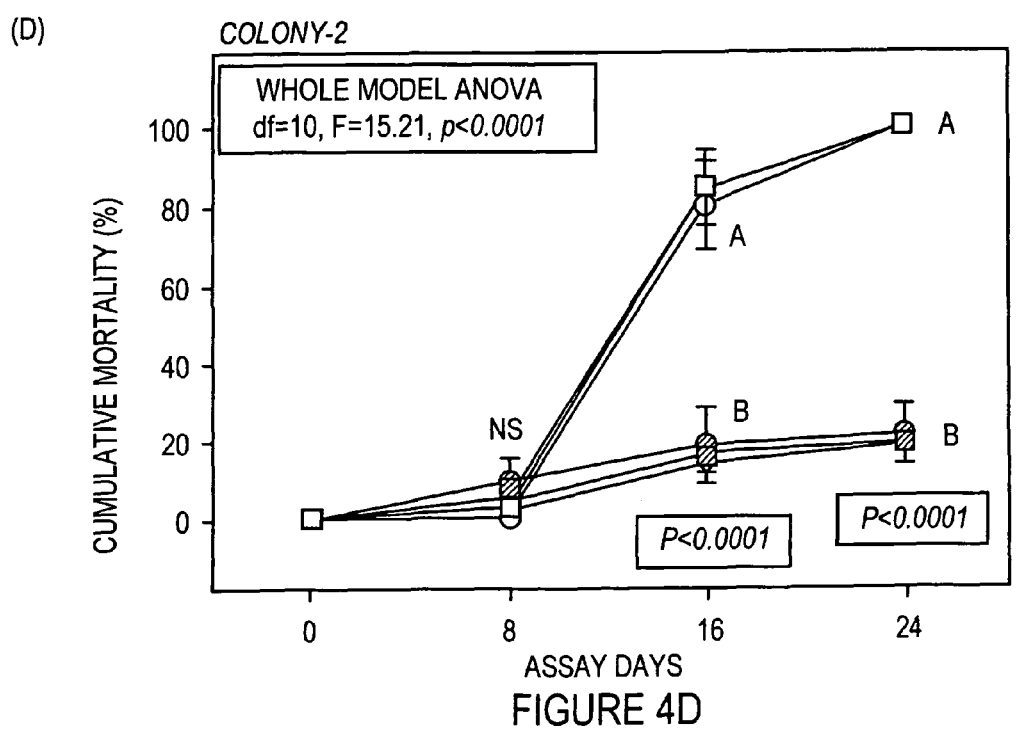

FIGS. 4A-4D shows phenotypic impacts displayed by *R. flavipes* workers after feeding on Hex-2-homologous dsRNA. Results for two colonies are shown: Colony-1 (FIGS. 4A, 4C), and Colony-2 (FIGS. 4B, 4D). The legend at the top of the figures summarizes the experimental treatments, which consisted of combinations of single and triple dsRNA and juvenile hormone (JH) deployments. "No. doses" refers to the number of dsRNA doses that were provided in assays (0, 1, or 3). (FIGS. 4A, 4B). Cumulative presoldier formation by *R. flavipes* workers through 24-d as induced by the various Hex-2 dsRNA and JH experimental treatments. Means within days with the same letter are not significantly different by Fisher LSD t-tests at p-values shown. Prior to conducting any t-tests, significant variation in the whole data set was first verified by ANOVA (results shown in boxes at top left of each graph). FIGS. 4C, 4D). Mortality in *R. flavipes* workers from two colonies through 24-d as induced by the various Hex-2 dsRNA and JH experimental treatments. Means within days for each colony with the same letter are not significantly different by Fisher LSD t-tests at p-values shown. Statistical analyses were performed as in FIGS. 4A, 4B above. All error bars represent standard error of the mean, as determined from three independent replicates.

Figures 5A, 5B, 5C:
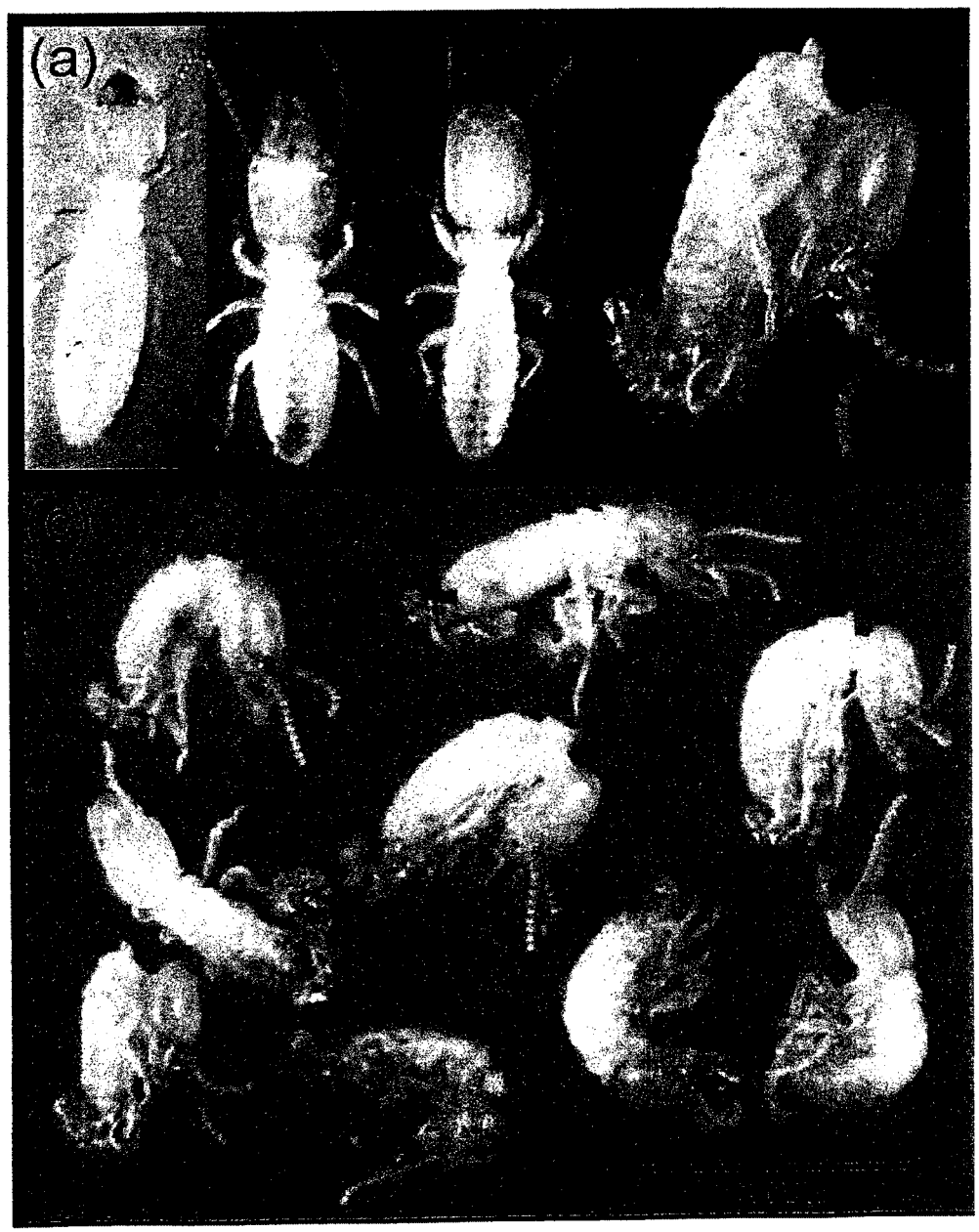
FIGS. 5A, 5B and 5C show morphological impacts in R. flavipes termites after Hex-2 dsRNA feeding, both with and without co-application of ectopic juvenile hormone (JH).

FIGS. 5A-5C shows morphological impacts in *R. flavipes* termites after Hex-2 dsRNA feeding, both with and without co-application of ectopic juvenile hormone (JH). Photographs were taken of alcohol-preserved individuals using a digital synchroscopy system. FIG. 5A shows "Normal" or wildtype caste phenotypes as would naturally appear in termite colonies, or as induced by feeding on Hex-2 dsRNA alone or JH alone: worker (left), presoldier (middle), and soldier (right).

FIG. 5B shows an extreme example of a worker that underwent a lethal status-quo molt immediately after ingesting a second dose of Hex-2 dsRNA+JH. Note the hunchback posture, yellow coloration, and attachment of cast skin. All effects are analogous to symptoms of poisoning by chitin synthesis inhibitor insecticides (ref. Su & Scheffrahn 1993, Dhadialla et al. 2005).

FIG. 5C shows workers and presoldiers after lethal molts as induced by two doses of Hex-2 dsRNA+JH. Despite the range of malformations, all individuals were lethally affected.

Figures 6A, 6B:
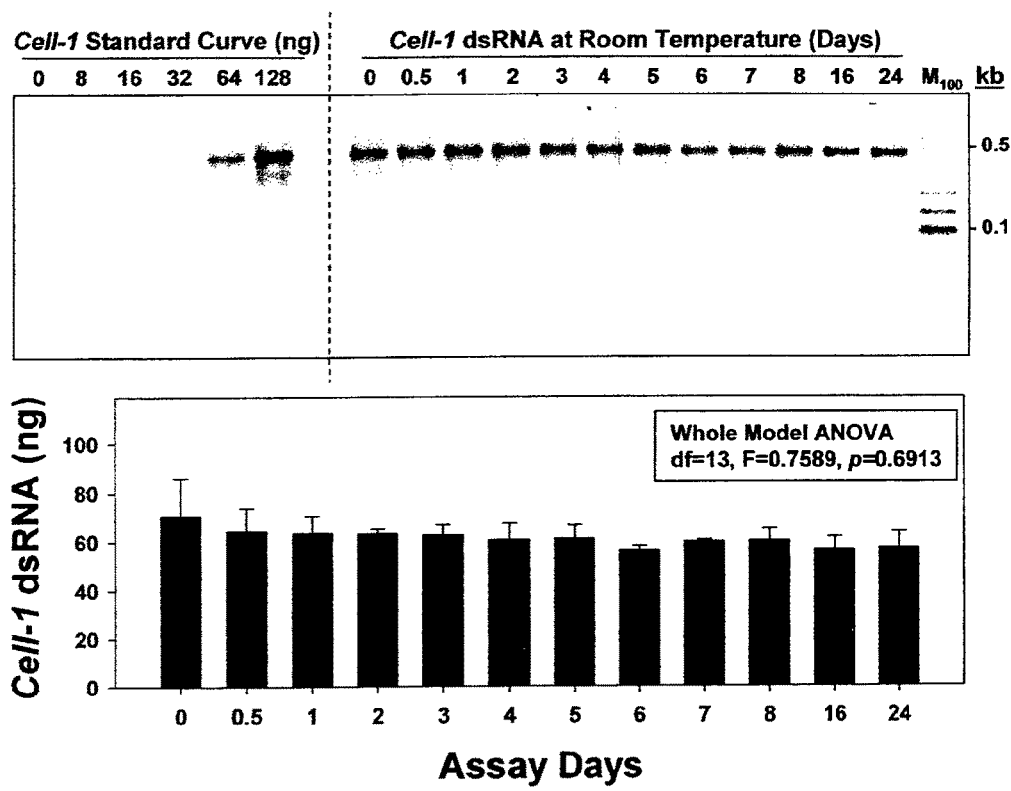
FIGS. 6A and 6B shows Cell-1 dsRNA stability.

FIGS. 6A-6B shows Cell-1 dsRNA stability. Synthesized Cell-1 dsRNAs (50 ml) from *R. flavipes* were stored in a 0.6 ml micro-centrifuge tube at room temperature (±25° C.) for a period of 24 days. One micro-liter of Cell-1 dsRNA was removed and transferred into a micro-centrifuge tube containing 9 ml of dsRNA solvent at day 0, 0.5, 1, 2, 3, 4, 5, 6, 7, 8, 16, and 24, respectively. After 24 days, samples from each day were subjected to agarose gel electrophoresis (a representative gel from three replications is shown in FIG. 6A with a 100 bp size ladder from Bio-Rad (M100) and an in-gel mass standard of Cell-1 dsRNA (a, left). Based on the in gel standard curve, the amount of remaining Cell-1 dsRNAs (ng) at each sample day was calculated. Densitometric analyses of all three replications are summarized in FIG. 6B. Error bars represent standard errors of the mean (n=3 replicates).

Figure 7B:
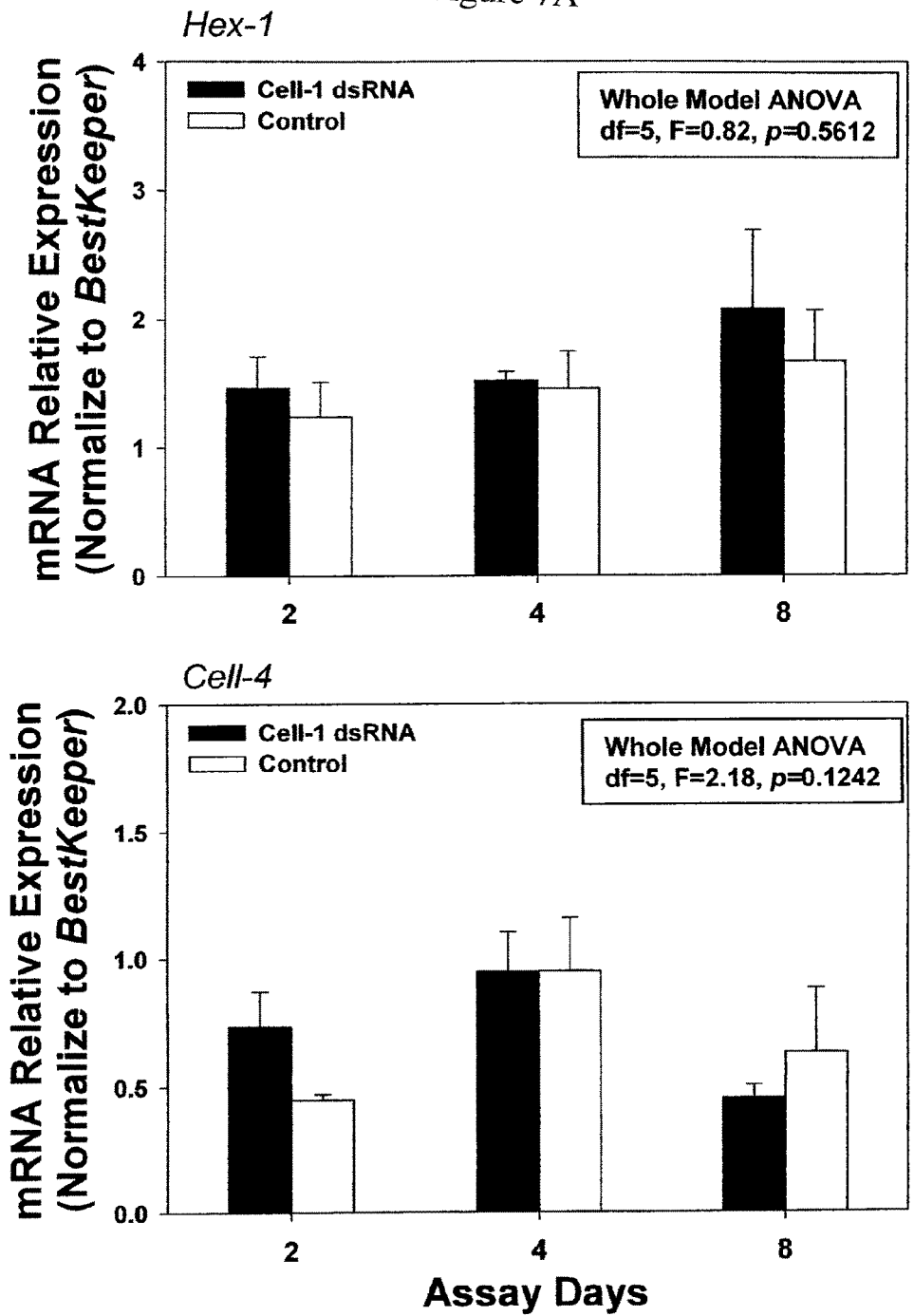

FIGS. 7A-7B shows genes not impacted in *R. flavipes* workers after feeding on Cell-1 endoglucanase-homologous dsRNA. FIG. 7A shows lack of Hex-1 gene expression differences between Cell-1 dsRNA treatments and controls at assay days 2, 4 and 8. FIG. 7B shows lack of Cell-4 gene expression differences between Cell-1 dsRNA treatments and controls at assay days 2, 4 and 8. Results are normalized to the three reference genes β-actin, NADH-dh and HSP-70 based on Bestkeeper analysis.

FIGS. 8A-8B shows the impacts of Cell-1 endoglucanase gene silencing on downstream cellulase enzyme activities. FIG. 8A shows Cell-1 silencing impacts endoglucanase activity on days 2 and 8. Asterisks denote significant differences between treatments and controls within days at p<0.05. Prior to t-tests, an ANOVA was performed on the whole data set to verify significance of the model statement (results shown in box). FIG. 8B shows lack of β-glucosidase activity differences between Cell-1 dsRNA treatments and controls for whole-body protein preparations at assay days 2, 4 and 8. All error bars represent standard error of the mean, as determined from three independent replicates.

Figures 9A, 9B:
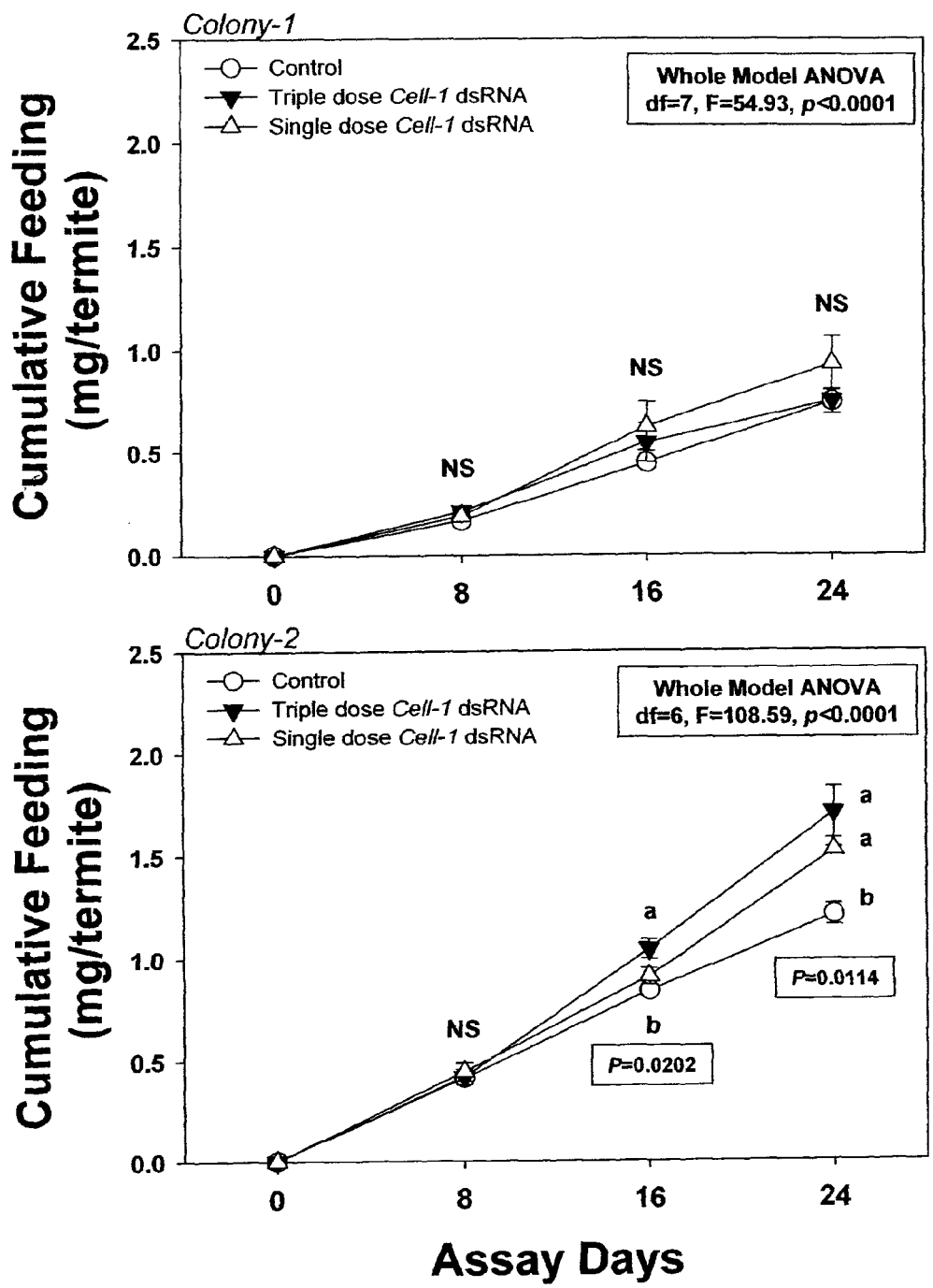
FIGS. 9A and 9B shows the effects of Cell-1 endoglucanase gene silencing on feeding by two termite colonies through 24-d assays.

FIGS. 9A-9B shows the effects of Cell-1 endoglucanase gene silencing on feeding by two termite colonies through 24-d assays. Colony-1 (FIG. 9A) showed no effects; while Colony-2 (FIG. 9B) showed significantly greater feeding in Cell-1 dsRNA treatments, suggesting compensatory feeding. Assay treatments included untreated controls (o), single dose dsRNA treatments provided at day 0 (D), and triple dose dsRNA treatments provided at days 0, 8 and 16 (▼). Means within days with the same letter are not significantly different by Fisher LSD t-tests at p-values shown. Prior to conducting any t-tests, significant variation in the whole data set was first verified by ANOVA (results shown in boxes at top right of each graph). All error bars represent standard error of the mean, as determined from three independent replicates.

Figures 10A, 10B:
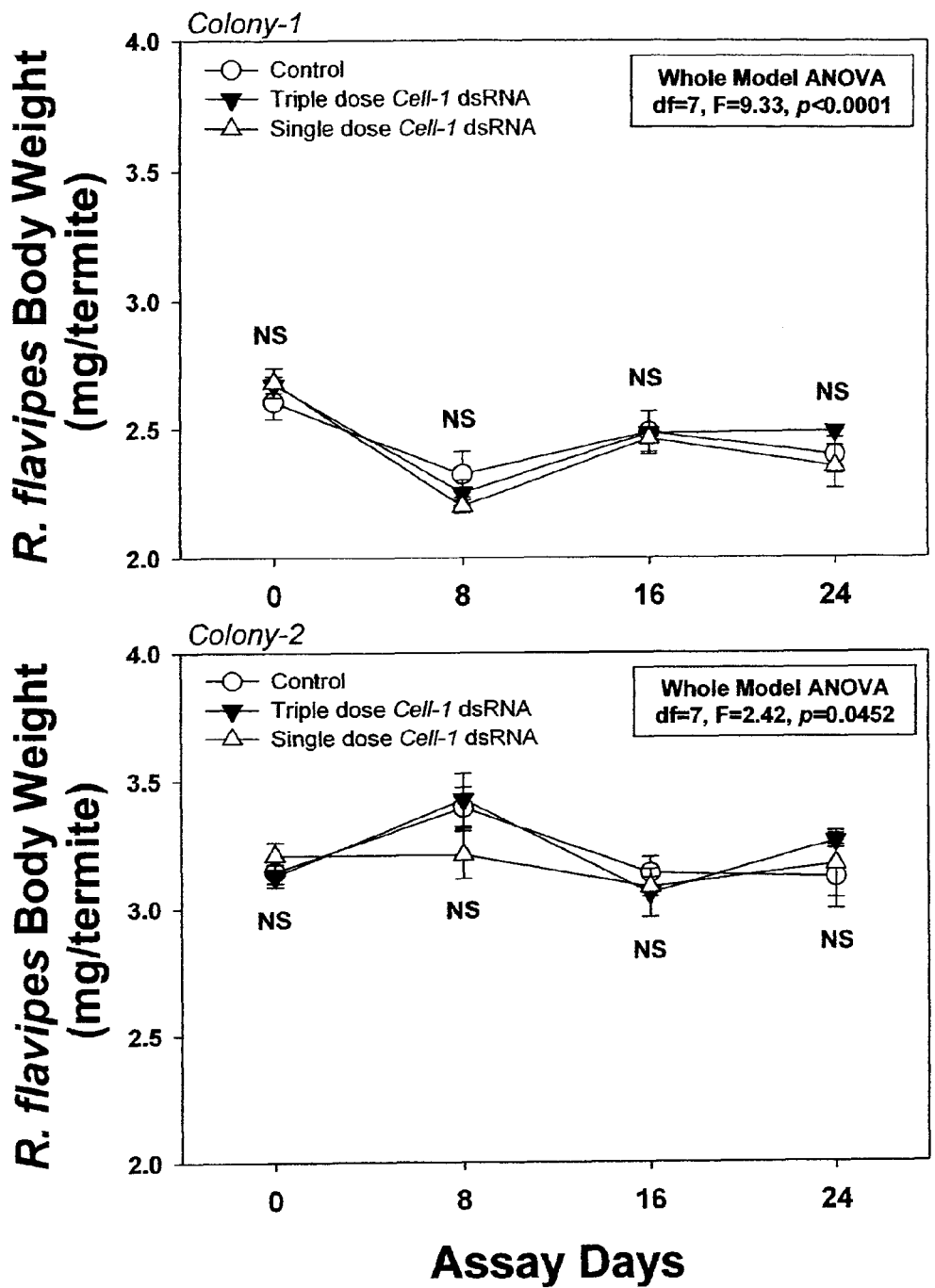
FIGS. 10A and 10B shows the effects of Cell-1 endoglucanase gene silencing on body weight for two termite colonies through 24-d assays.

FIG. 10 shows the effects of Cell-1 endoglucanase gene silencing on body weight for two termite colonies through 24-d assays. Neither Colony-1 (FIG. 10A) nor Colony-2 (FIG. 10B) showed significant changes in body weight in response to Cell-1 dsRNA treatments. Although ANOVA analyses suggested significant variation, none of the within-day Fisher LSD t-tests showed significant differences. Assay treatments included untreated controls (o), single dose dsRNA treatments provided at day 0 (D), and triple dose dsRNA treatments provided at days 0, 8 and 16 (▼). All error bars represent standard error of the mean, as determined from three independent replicates.

Figure 11:
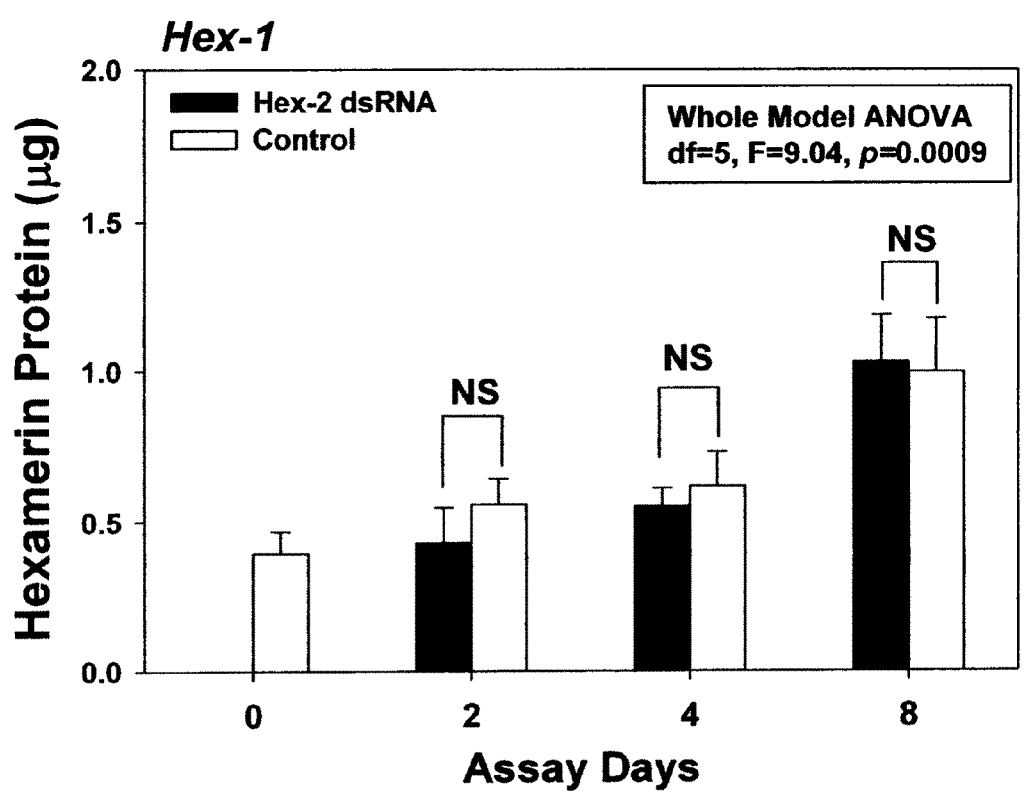
FIG. 11 is a densitometric analysis summary for the Hex-1 hexamerin protein from replicated SDS-PAGE gels as shown in FIG. 3.

FIG. 11 shows the densitometric analysis summary for the Hex-1 hexamerin protein from replicated SDS-PAGE gels as shown in FIG. 3C. Hex-1 quantities in mg were determined from in-gel standard curves of bovine serum albumin (not shown; see text for details). No significant differences in Hex-1 protein expression were observed between Hex-2 dsRNA treatments and controls within days (p>0.05). Statistical analyses were performed as described for FIG. 3. All error bars represent standard error of the mean, as determined from three independent replicates.

Figure 12A:
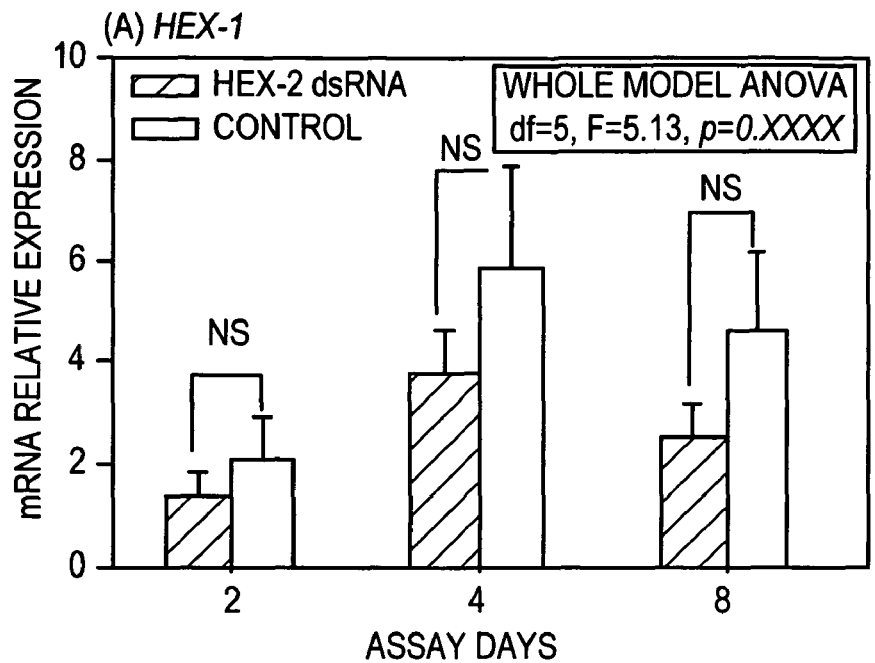
FIGS. 12A, 12B, 12C, 12D, 12E and 12F shows negative results for six non-target genes after Hex-2 gene silencing by Hex-2 dsRNA feeding on assay days 2, 4 and 8.
Figure 12B:
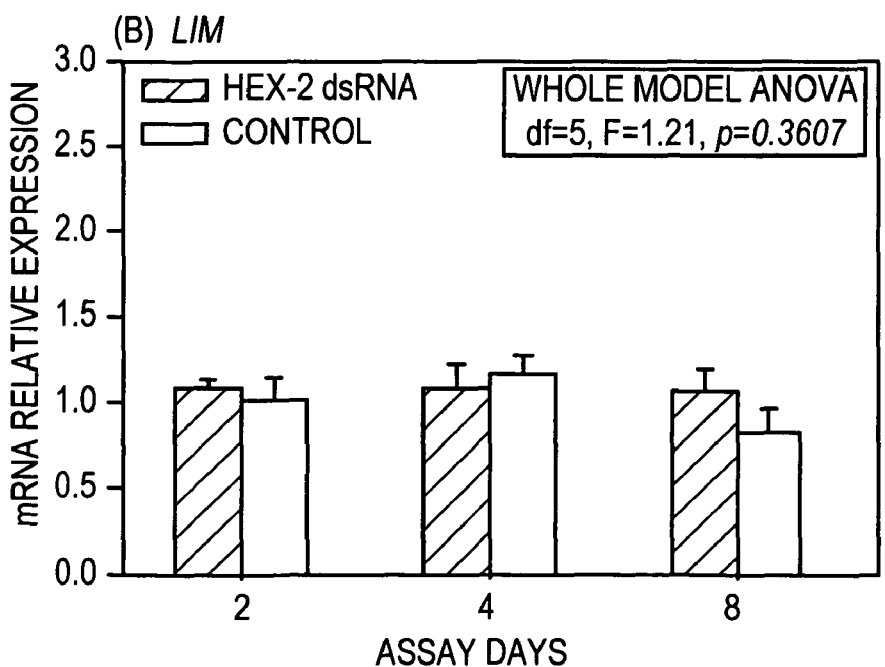
Figure 12C:
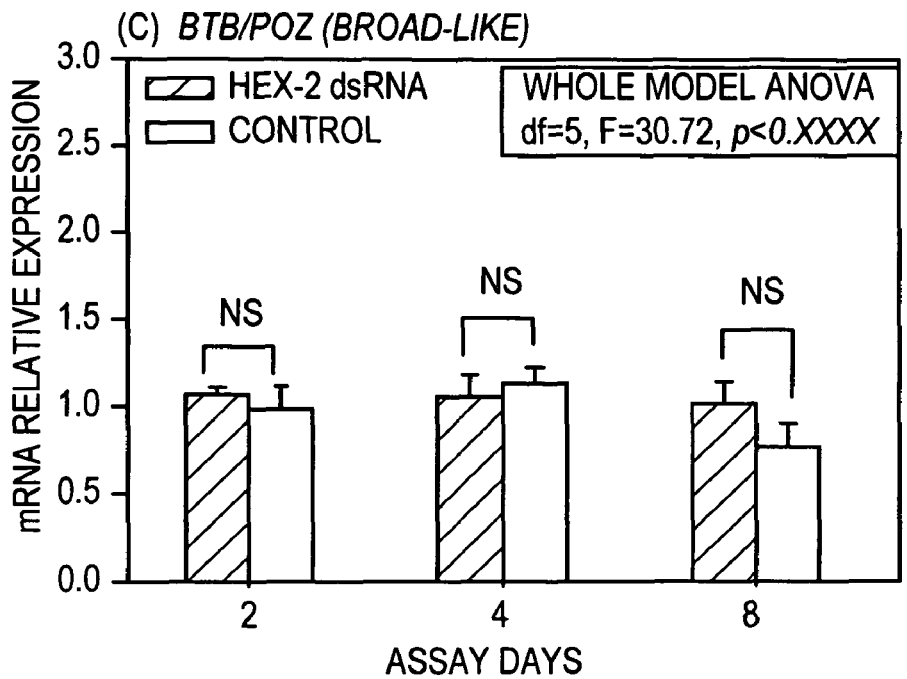
Figure 12D:
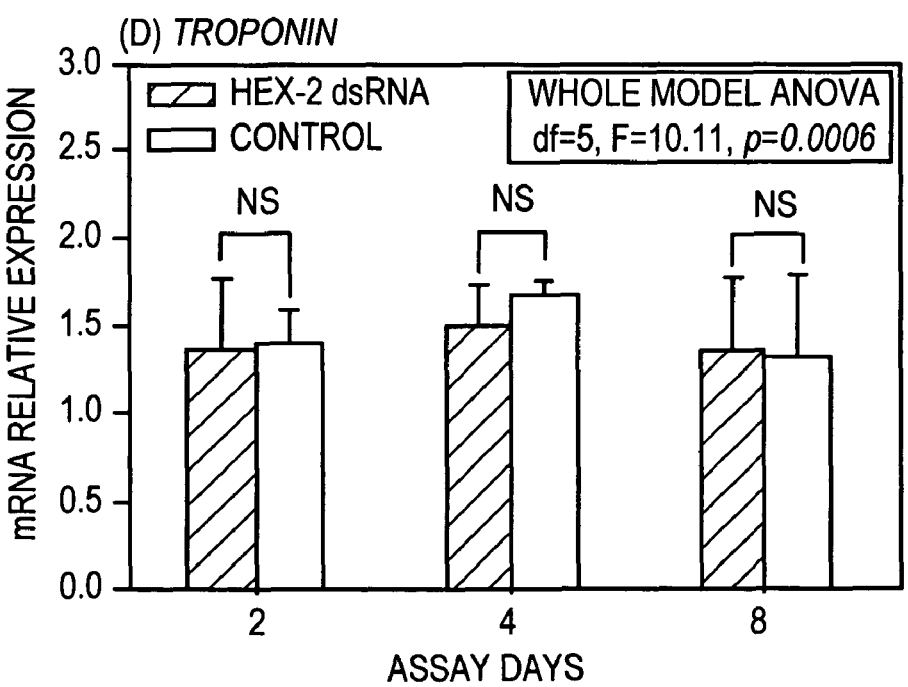
Figure 12E:
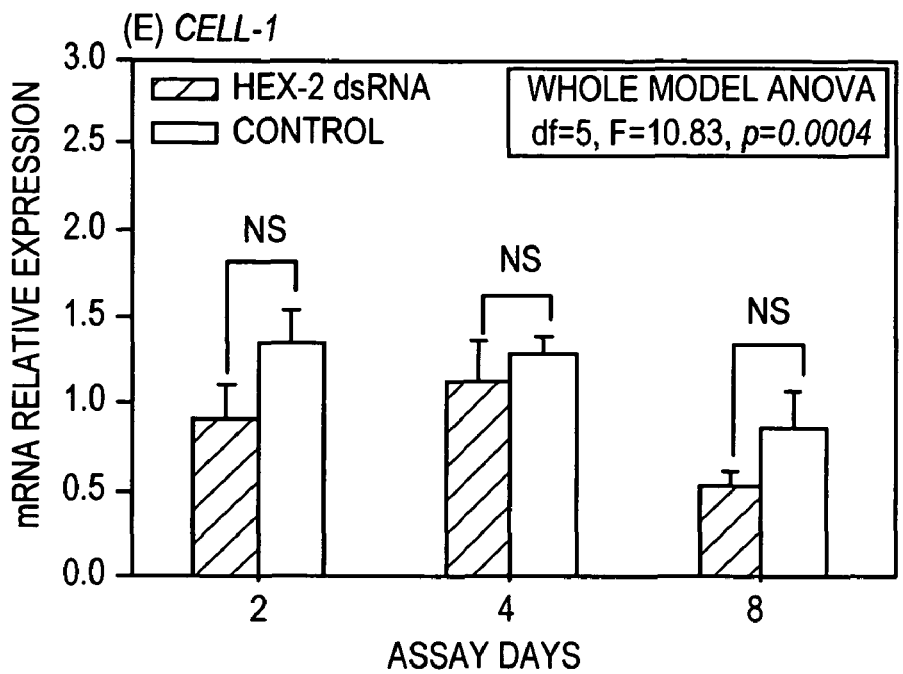
Figure 12F:
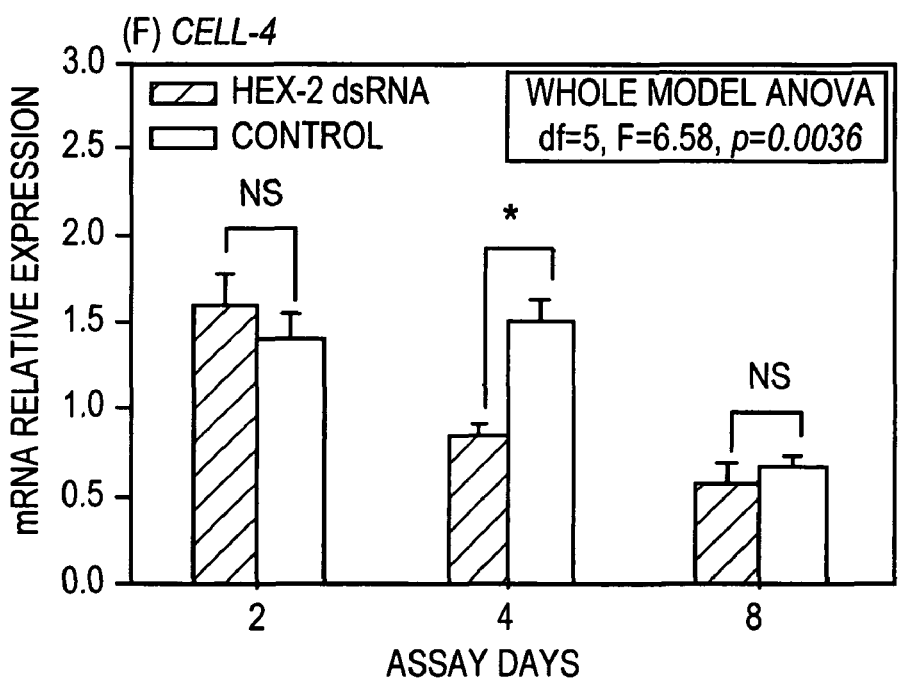

FIGS. 12A-12F shows the negative results for six non-target genes after Hex-2 gene silencing by Hex-2 dsRNA feeding on assay days 2, 4 and 8. The six genes examined were Hex-1 (FIG. 12A), LIM (FIG. 12B), BTB/POZ (FIG. 12C), Troponin (FIG. 12D), Cell-1 (FIG. 12E), and Cell-4 (FIG. 12F). The only gene affected was the symbiotic cellulase Cell-4, which may represent a gut symbiont response to caste differentiation as induced by Hex-2 silencing. mRNA expression levels on y-axes are normalized to the three reference genes β-actin, NADH-dh and HSP-70 based on Bestkeeper analysis (see Supplementary Table 2). Asterisks denote significant differences between treatments and controls within days, as determined using pairwise t-tests (p<0.05). Prior to t-tests, an ANOVA was performed on the whole data set to verify significance of the model statement (results shown in boxes). All error bars represent standard error of the mean, as determined from three independent replicates.

Figure 13A:
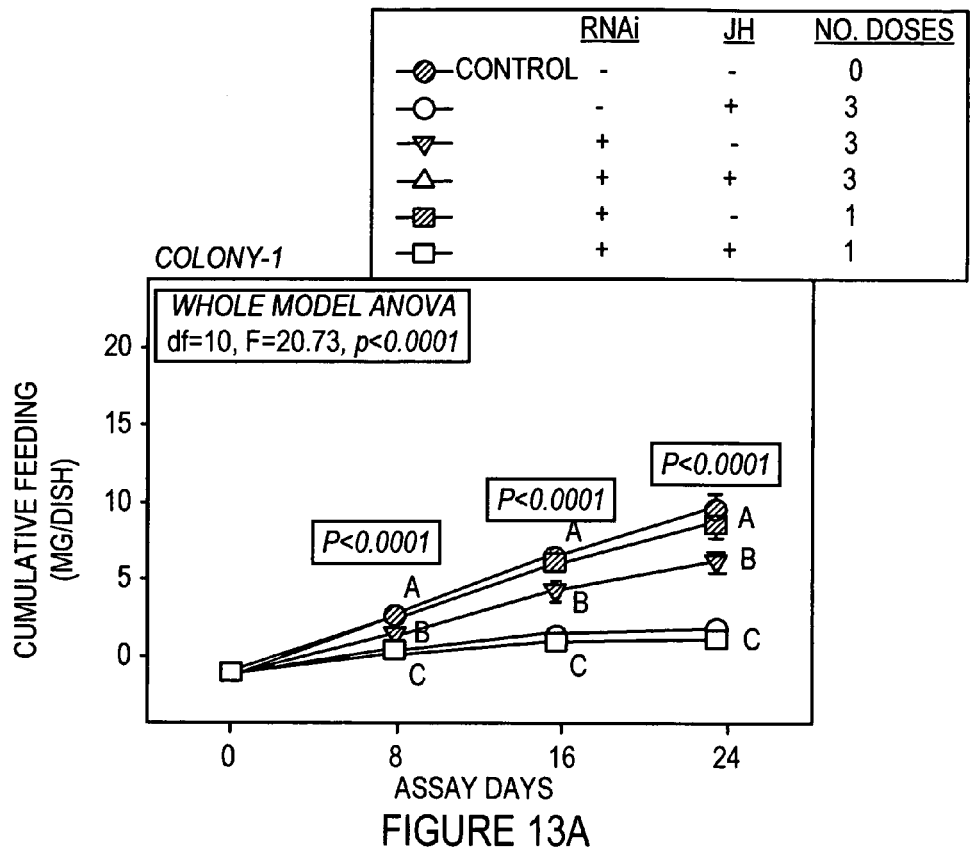
FIGS. 13A and 13B shows feeding impacts displayed by R. flavipes workers after feeding on Hex-2-homologous dsRNA.
Figure 13B:
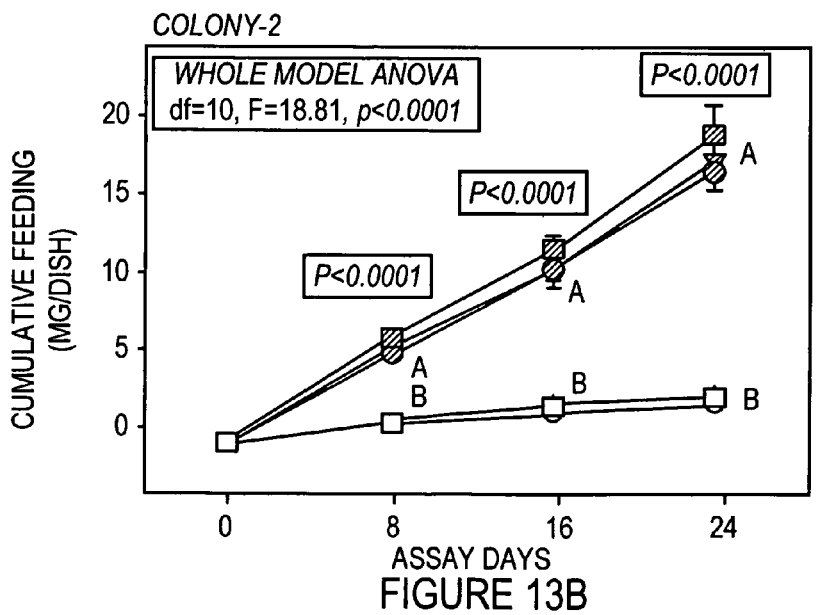

FIGS. 13A-13B shows the feeding impacts displayed by $R.$ $flavipes$ workers after feeding on Hex-2-homologous dsRNA. Results for two colonies are shown: Colony 1 (FIG. 13A); Colony 2 (FIG. 13B). The legend at the top of the figure summarizes the experimental treatments, which consist of combinations of single and triple dsRNA and juvenile hormone (JH) deployments. "No. doses" refers to the number of dsRNA doses that were provided in assays (0, 1, or 3). Means within days for each colony with the same letter are not significantly different by Fisher LSD t-tests at p-values shown. Prior to conducting any t-tests, significant variation in the whole data set was first verified by ANOVA (results shown in boxes at top left of each graph). All error bars represent standard error of the mean, as determined from three independent replicates.

Figures 14A, 14B:
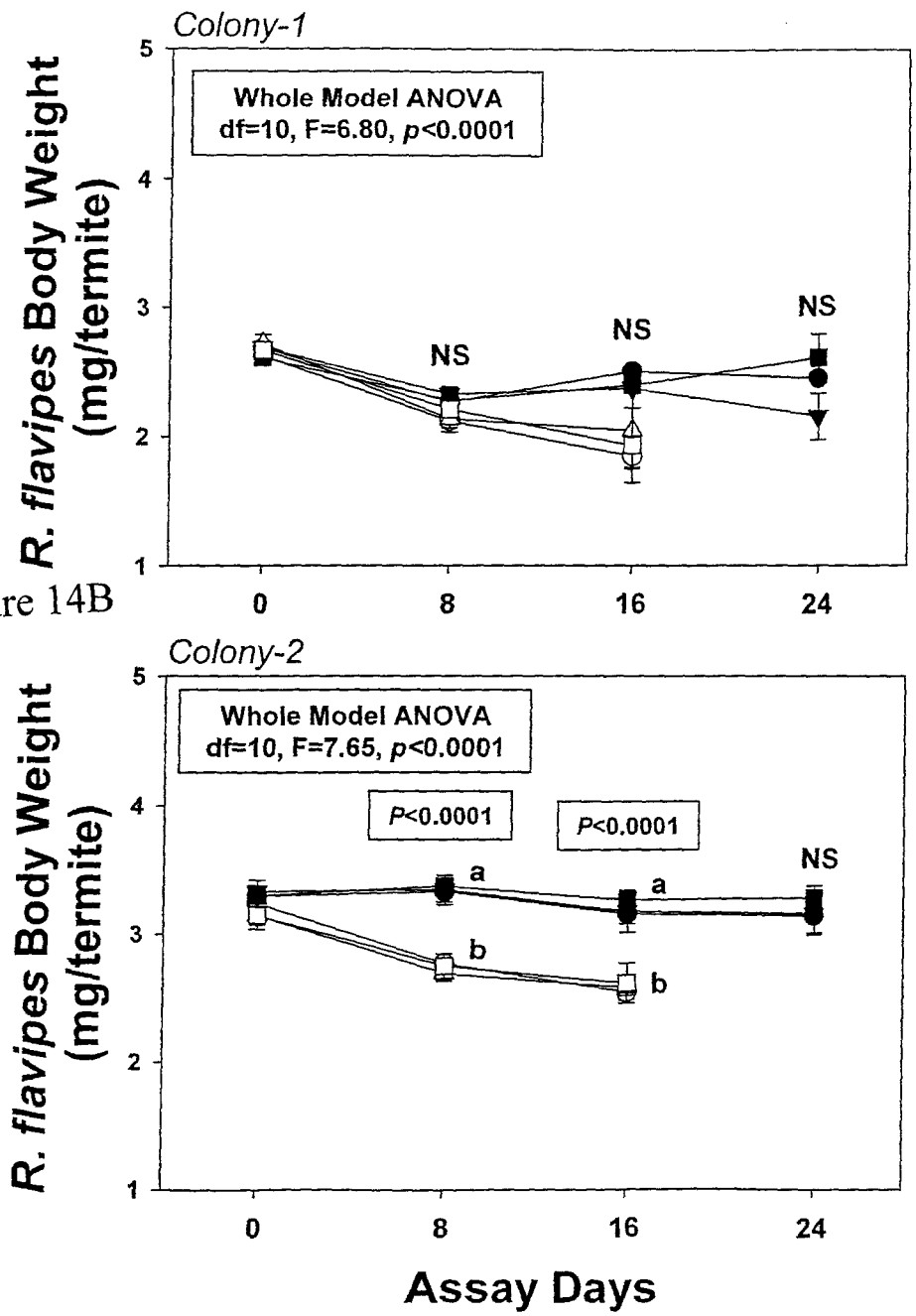
FIGS. 14A and 14B shows body weight impacts displayed by R. flavipes workers after feeding on Hex-2-homologous dsRNA.

FIGS. 14A-14B shows the body weight impacts displayed by $R.$ $flavipes$ workers after feeding on Hex-2-homologous dsRNA. Results for two colonies are shown: Colony 1 (FIG. 14A); Colony 2 (FIG. 14B). The legend at the top of the figures summarizes the experimental treatments, which consist of combinations of single and triple dsRNA and juvenile hormone (JH) deployments. "No. doses" refers to the number of dsRNA doses that were provided in assays (0, 1, or 3). Means within days for each colony with the same letter are not significantly different by Fisher LSD t-tests at p-values shown. Prior to conducting any t-tests, significant variation in the whole data set was first verified by ANOVA (results shown in boxes at top left of each graph). All error bars represent standard error of the mean, as determined from three independent replicates.

FIGS. 15A-15D shows the positions of PCR primer sets used for amplifying dsRNA templates and quantitative real-time PCR [qRT-PCR], as well as their sequences. (FIG. 15A) Gene diagram for Cell-1 gene. (FIG. 15B) PCR primers for Cell-1 dsRNA template amplification and qRT-PCR. (FIG. 15C) Gene diagram for Hex-2 gene. (FIG. 15D) PCR primers for Hex-2 dsRNA template amplification and qRT-PCR. PCR primers used for dsRNA template amplification additionally had T7 RNA polymerase recognition sequences appended onto their 5' ends (5'-TAATACGACTCACTATAGGG-3') (SEQ ID NO: 1).

FIG. 16 shows a supplementary Table 1 of statistical comparisons of CT values between reference and target genes from Cell-1 dsRNA feeding bioassays.

FIG. 17 shows a supplementary Table 2 of Statistical comparisons of CT values between reference and target genes from Hex-2 dsRNA feeding bioassays.

FIG. 18 shows a supplementary Table 3 of termite gene identities, abbreviations, accession numbers and qRT-PCR primer sequences used in Cell-1 and Hexamerin RNAi studies.

FIG. 19 shows complete coding sequences of the $Reticulitermes$ $flavipes$ endogenous Cell-1 cellulase gene, complete coding sequence. Genbank Accession Number AY572862.

FIGS. 20A-20B shows a complete coding sequences of the $Reticulitermes$ $flavipes$ Hexamerin-1 and Hexamerin-2 genes. Genbank Accession Numbers AY572858 (Hex-1) and AY572859 (Hex-2).

FIG. 21 shows mortality increases over time for worker termites in Hex-2 dsRNA donor-recipient experiments. No presoldier differentiation was observed. Significant mortality occurred only in the 5:10 donor: recipient treatments.

FIGS. 22A-22F shows *R. flavipes* gene sequences for the JH-linked developmental genes broad, Farnesoic Acid Methyl Transferase-2, Family 15 Cytochrome P450-1 and -2, and Vitellogenin-1 and -2. Gene regions shaded in gray are dsRNA template regions; underlined regions indicate priming sites for T7 RNA polymerase motif-appended PCR primers (designed as described earlier for Cell-1 and Hex-2).

Figure 23A:
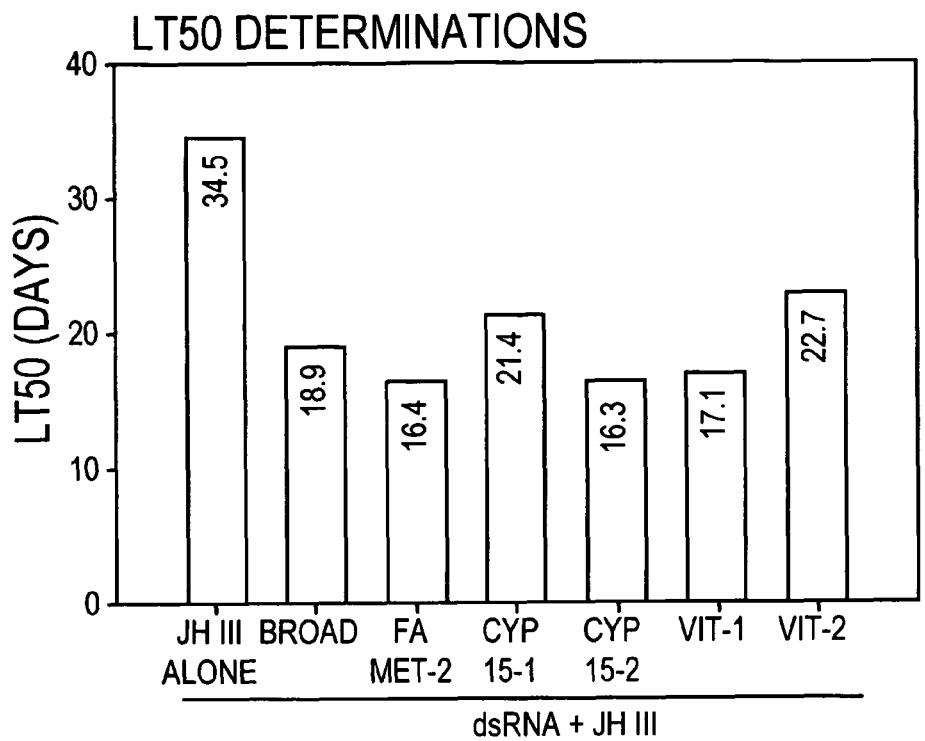
FIGS. 23A and 23B shows lethal times in days to reach 50 and 90% mortality in R. flavipes workers after feeding on papers treated with 20 μg of broad, farnesoic acid methyl transferase, Cyp15 P450, or vitellogenin dsRNA+112 μg juvenile hormone III.
Figure 23B:
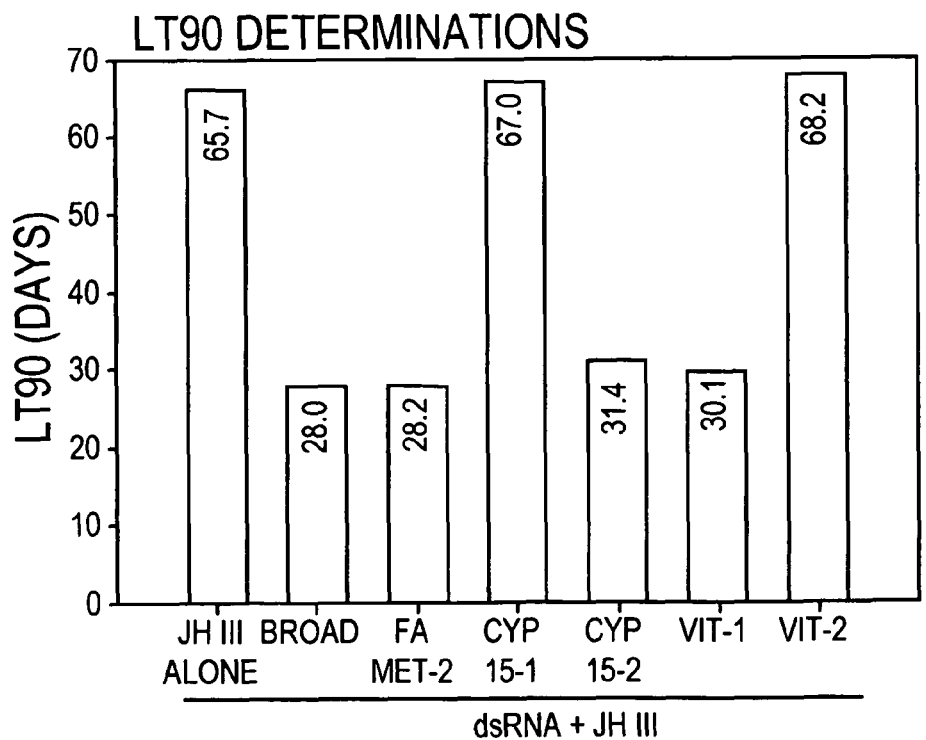

FIGS. 23A-23B shows lethal times in days to reach (A) 50% mortality [LT50] and (B) 90% mortality [LT90] in *R. flavipes* workers after feeding on papers treated with 20 μg dsRNA+112 μg juvenile hormone III (JH III), relative to JH III alone. Six genes were targeted by dsRNA treatments: broad, farnesoic acid methyl transferase (FAMET-2), two family 15 cytochrome P450s (Cyp15-1, Cyp15-2), and two vitellogenin genes (Vit-1, Vit-2). Silencing of all genes in combination with JH led to significantly faster LT50s; whereas, silencing of four genes in combination with JH led to significantly faster LT90s [broad, FAMET-2, Cyp15-2 and Vit-1].

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A method for regulating termite colony development with a food source comprising: feeding dsRNA corresponding to one or more of the group consisting of the Hex-1, Hex 2, genes to the termites in said colony.

2. A method, as in claim 1, wherein said dsRNA is embedded in a bait matrix.

3. A method, as in claim 2 wherein said bait matrix further comprises: one or more of the group consisting of natural juvenile hormone, synthetic juvenile hormone and terpenes.

4. A method, as in claim 3, wherein said natural juvenile hormone includes natural JH homologs selected from the group consisting of one or more of JH 0, JH I, JH II, and JH III, said synthetic juvenile hormone includes synthetic JH analogs are selected from the group consisting of one or more of methoprene, fenoxycarb, hydroprene, kinoprene, pyriproxyfen, juvenogens, and paper factor and said terpenes are selected from the group consisting of one or more of cadinene, cadinene-aldehyde, thujopsene, thujone, gurjunene, nerolidol, farnesol, nootkatone, E-beta-farnesene, geranyl geraniol, humulene, limonene, linalool, geranyl linalool, alpha-pinene, and beta-pinene.

5. A method for decreasing the fitness of a termite colony with a food source comprising feeding one or more of the group of dsRNA corresponding to the Hex-1, Hex-2, genes to the termites in said colony.

6. A method, as in claim 5, wherein said dsRNA is embedded in a bait matrix.

7. A method, as in claim 6, wherein said bait matrix further comprises: one or more of the group consisting of natural juvenile hormone, synthetic juvenile hormone and terpenes.

8. A method, as in claim 7, wherein said natural juvenile hormone includes natural JH homologs are selected from the group consisting of one or more of JH 0, JH I, JH II, and JH III, said synthetic juvenile hormone includes synthetic JH analogs comprise methoprene, fenoxycarb, hydroprene, kinoprene, pyriproxyfen, juvenogens, and paper factor and said terpenes are selected from the group consisting of one or more of cadinene, cadinene-aldehyde, thujopsene, thujone, gurjunene, nerolidol, farnesol, nootkatone, E-beta-farnesene, geranyl geraniol, humulene, limonene, linalool, geranyl linalool, alpha-pinene, and beta-pinene.

9. A method for regulating termite colony development and decreasing the fitness of a termite colony with a food source consisting of the steps of:

embedding dsRNA corresponding to one or more of the group consisting of the Hex-1, Hex-2 genes in a single bait matrix, embedding one or more of the group consisting of natural juvenile hormone, synthetic juvenile hormone and terpenes into the single bait matrix, wherein said natural juvenile hormone includes natural JH homologs selected from the group consisting of one or more of JH 0, JH I, JH II, and JH III, said synthetic juvenile hormone includes synthetic JH analogs are selected from the group consisting of one or more of methoprene, fenoxycarb, hydroprene, kinoprene, pyriproxyfen, juvenogens, and paper factor and said terpenes are selected from the group consisting of one or more of cadinene, cadinene-aldehyde, thujopsene, thujone, gurjunene, nerolidol, farnesol, nootkatone, E-beta-farnesene, geranyl geraniol, humulene, limonene, linalool, geranyl linalool, alpha-pinene, and beta-pinene;

feeding the dsRNA corresponding to one or more of the group consisting of the Hex-1, Hex-2, genes, and the group consisting of the natural juvenile hormone, the synthetic juvenile hormone and the terpenes, in the single bait matrix as a food source to the termites in said colony; and regulating termite colony development and decreasing the fitness of the termite colony with the food source in the single bait matrix.

* * * * *

SEQUENCE LISTING

```
<160> NUMBER OF SEQ ID NOS: 40

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 1
taatacgact cactataggg                                              20

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 2
agacatgacg atgtccagac c                                            21

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 3
gacccttggg tgtcttct                                                18

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 4
tcacaagcaa gcaggcatac                                              20

<210> SEQ ID NO 5
<211> LENGTH: 20
<212> TYPE: DNA
<213> ORGANISM: Artificial Sequence
<220> FEATURE:
```

```
<223> OTHER INFORMATION: Description of Artificial Sequence:
      Synthetic primer

<400> SEQUENCE: 5
atgagagcag aattggcaga                                            20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 6
atacgccaat ggacaggaag                                            20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 7
gcgcttgagg atttggtagt                                            20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 8
acggaagacg ttggagtcag                                            20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 9
gaggacctgc tggatcttgt                                            20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 10
acggaagacg ttggactcag                                            20

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence:
      Synthetic primer
```

```
<400> SEQUENCE: 11
gatccattcc acaagcacg                                                    19

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 12
tcacaagcaa gcaggcatac                                                   20

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 13
gctgggggtg ttattcattc cta                                               23

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 14
cgtcgacacc gactacgac                                                    19

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 15
cgacctagaa tacgaagtgg                                                   20

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 16
ctggaccagc atctacatct tc                                                22

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 17
```
gtgcttcaag tgtggcatgt                                                    20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 18
agagggaaat cgtgcgtgac                                                    20

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 19
gctgggggtg ttattcattc cta                                                23

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 20
agaaccaagt ggccatgaac                                                    20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 21
gaggacctgc tggatcttgt                                                    20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 22
acattctcca ccgtcactcc                                                    20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 23
atgagagcag aattggcagc                                                    20

```
<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 24
cttcgagcaa gcatgaactg                                              20

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 25
ggtcagcggt gtactcgac                                               19

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 26
ttcttctcct tgtcctcctc c                                            21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 27
ggttgaagcc tgattcacaa g                                            21

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 28
gtccatgctg agacaaccag                                              20

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 29
caatagtgat gacctggccg t                                            21
```

```
<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 30
ggcataccac aaagagcaaa a                                            21

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence:
      Synthetic primer

<400> SEQUENCE: 31
ccaatgcttc atgtctgcc                                               19

<210> SEQ ID NO 32
<211> LENGTH: 1489
<212> TYPE: DNA
<213> ORGANISM: Reticulitermes flavipes

<400> SEQUENCE: 32
ccactaccag ccgccatgaa ggtcttcgtt tgtcttctgt ctgcactggc gctttgccaa    60
gctgcttacg actataagac agtactaagc aattcgctac ttttctacga ggctcagcga   120
tcgggaaaat tgccgtctga tcagaaggtc acgtggagga aggattccgc ccttaacgac   180
aagggccaga agggcgagga cctgacagga ggatactatg acgctggtga ttttgtgaag   240
ttcggcttcc ctatggcgta cacagtcacc gtcctcgctt ggggtgttat agactacgaa   300
tcagcgtatt ctgcagcagg agctctggat agtggtcgca aggctcttaa atatggcacg   360
gactacttcc tcaaggcgca cacggccgcg aacgaattct acggacaagt gggccaggga   420
gatgtcgacc acgcctactg gggacgtcca gaagacatga cgatgtccag acctgcctac   480
aagatcgaca cgtcgaaacc agggtctgac ctggcagccg agacagccgc cgccctcgct   540
gcaactgcca tcgcctacaa gagtgctgac gcaacttatt ccaacaactt gatcacccac   600
gccaagcagc ttttcgactt cgccaacaat tatcgcggca atacagtga ttcaatcacc    660 gacgcgaaga atttctacgc gtccggagac tacaaggacg agttagtatg ggcagccgca   720
tggctctaca gggcgaccaa cgacaacacc tatctgacta agctgaatc gctatacaac    780 gaattcggcc tcggaaactg aacggtgcc ttcaactggg ataacaagat ctccggtgta    840
caggttctac tggccaagct cacaagcaag caggcataca aggacaaggt acaaggctac   900
gtcgattact tgatttcgtc tcagaagaag acacccaagg gtctcgtata catcgaccag   960
tggggtaccc tgcgacatgc tgccaattct gctctcattg ctctgcaggc agccgacctg  1020
ggtatcaatg ctgctactta cgcgcgtat gccaagaagc agatcgatta cgcattgggt   1080
gatggaggtc gcagctacgt cgtaggattt ggtactaacc cacccgtacg ccctcaccac  1140
agatccagct cgtgccctga cgcaccagcc gtatgtgact ggaacacgta caacagcgcc  1200
ggccccaatg cccacgtact caccggagcc ttggtgggtg gtccagatag caacgatagc  1260
tacacggacg ctcgcagcga ttacatctcc aacgaagtgg ccacagatta caacgctggc  1320
ttccaatcag ctgtcgctgg tctcctcaag gctggcgtgt aaccgcacac agcactcaat  1380
gtctccctgt ccactggaca tgtgtacaat ttgacaacga aaatgtaata ttcttcagaa  1440
```

```
aagtgcaata aaagttcaca attcaacaca aaaaaaaaaa aaaaaaaa              1489
```

<210> SEQ ID NO 33
<211> LENGTH: 3242
<212> TYPE: DNA
<213> ORGANISM: Reticulitermes flavipes
<220> FEATURE:
<221> NAME/KEY: modified_base
<222> LOCATION: (2547)..(2547)
<223> OTHER INFORMATION: a, c, g, t, unknown or other

<400> SEQUENCE: 33

```
ctagtctgtt tttttttttt tttttcagt tcctcattca ctctttccgc ctccaatttc    60
ctcgcttcca acactttctt tgctgccttg ttagcctctt ccttctcctt cattgcctgt   120
gcaatcccct cttccttttc cttctttgcc tgtgcaatct tctcttcttc ctccttcttt   180
gcctttgcaa tcccttcttt tctttccttc tttgcctgtg caatctgttc ttccattttc   240
ttccttaatt ccacattctc atttccgcc tttaatttcg tcacttccaa cactttcttt   300
gctgccttgt cagcctcttc tttctccttc attacctgtg caatcccttc ttccttttcc   360
ttctttgcct gtgcaatctt ctcttcttcc tccttctttg cctgtgcaat cccttcttct   420
ttttctttct ttgcctgtgc aatctcatct tcttttctt tctttgcctg tgcaatctgt   480
tcttccattt tctttttcag ttcctcattc actctttccg cctccaattt cctcgcttcc   540
aacactttct tgctgccttg tcagcctct tccttctcct tcattgcctg tgcaatccct   600
tcttccttt ccttctttgc ctgtgcaatc ttctcttctt ctatgaacac tgctctcctg   660
ttcgcgacag tcgtggccgt cttggtctgc ggcgccttct ctgaccacca tgtagggaag   720
aaagtagcag acaaaccgtt cctcatgaag cagaaaaaca tcctagggct ggtccacagg   780
attcatcaag ataatctatt caaagagcag gttgatgtgg gtaataccta tgacattgaa   840
gcacatatca gcaactacaa gaatacaaaa gtagtgaaag agtttatatc ctactacaag   900
aagggcatgc tgcaacgctg ggagccgttc tcagtgtatt acaagactca ccttgaacag   960
gctatctcct tgttcgagct cttctatttc gctaacgact tcgatacttt ctacaagacc  1020
gcctgctggg cccgcgaccg tgtgaacccg ctcatgttct ggtattcttt cactgctgcc  1080
gtcctccacc gcgacgacac gacagatgtc atgatgccgc cgccctacga agtgtaccca  1140
tacttcttcg tagacagtga tatcatccaa aaggcctaca agtactggat gatgcacgtt  1200
ggcaccactg aacatcacac ctacatcatc ccaatgaatc acaccatgaa gagcaaggag  1260
aatttgctct actactttac agaagacgtg ggcttgaacg ctttcaacat gtactaccgc  1320
atgtactacc ccagctggtt caacgttacg gagtacggcc acaagttcga ccgtcgcggc  1380
gagatgttcc tctacgtgca gcaccagctg tacgctcgct acagcttgga gagaatgtcc  1440
aacggcatgc ccgaagttga gcccttcgtc tacaacaaac ccctcaagac cgcatacaac  1500
cccaacctga tgtaccacac cggccaagaa atgcctccac gccccagcga catgctcgtg  1560
actaacttcg acacgtacac catcgaagac atcaagaact acgaacggag ggtggcggac  1620
gtaatcgact tcggctactt caaggacgaa caccctcaaag ttcactccat gtacgaggat  1680
aataatggca tcaactacct aggccagatg atagaaggct cctacaactc cccccactac  1740
tattactacg gttccctgtt tcacttctac cgcatgatgt tagggcacat gatggatcca  1800
ttccacaagc acgggctcgc acccagcgcc ctggaacaac cagagacagc cctgagggat  1860
cccgcctact accagctgta caagcgaatg taccacttag tcaataagta caaggacagg  1920
ctgcctcgct acacgcacga acagctttgg ttcgaaggag tgacggtgga gaatgtggat  1980
```

```
gttggtaaga tgtacacgta catggagaac tttgagttta gcctgggcgg caccatatat    2040
gtggccaagg aggaggatat gttaggtgtg aacttgcatg ttcggcagcc acgtctgaat    2100
cacaagccat tcacctataa gatagaggtc agcagcgaaa aggcagtcga tgcatacgtg    2160
cgtgtgttct tgggccccaa gcataattac ctggacgagg aatgggactt gaatgagcgc    2220
aggcacttct tcgtcgagat ggaccgcttc cggcatcatg tcccagctgg caagagtgta    2280
atcgaacgca actcccacga ctcctcaata attgcaccta cacccgacag ctacaggaca    2340
ttcgtcaaga aagtgcagga cgcttatgat ggcaaaaccc aatacttcat cgacaagagc    2400
cacaactact gcggattccc cgagaatctg ctgctgccca agggccagaa gggaggtgag    2460
accttcactt tctacgtcat aatcacgcca tacgtcaaac aggatgagca cgacttcgag    2520
ccttacgact acaaagcctt tagctantgc ggcgtgggac aagaccgcaa gtatcctgac    2580
gacatgccac tgggattccc cttcgaccgc cagatccata gcaaggactt ctacacccac    2640
caacatgtac ttcaaggatg tacaatcttt ccacaagaaa ctcgaagaag tcagtactcc    2700
cacccactag acaacaatg tgagatttca acgtcacatc tgttgagcgg aaatgggttc    2760
agtatttcga aacctaaggc aactgacata ttgcaatctg atgtcctcac attggtgaat    2820
ataatactgc ggttttctgg aatgtgttgt cgtatattat ggtagagtat gtgctaaagt    2880
ttcgggggag aatactacca ccattctacc cagaagaagt aagcaccatg tttctccaag    2940
aagtcggtat ctatctacca aataaagcgg cgccaaatcc cagaaggcag tagtcctaac    3000
ctgaaatact gatgtacagt ttcaaactta acgaccagtt tctgttgcaa tactgaattc    3060
atgatctatg tatcgtattt tttggcttcg accgatctgt aagtcacgat gaatgactac    3120
tcgcttgtac tggagaattt gaactgaatc actttataca ttatctgtga gatgtgtatg    3180
tccaatcttt aatagataaa atagtgcaat aaaaacagaa atataaaaaa aaaaaaaaa    3240 aa                                                                   3242

<210> SEQ ID NO 34
<211> LENGTH: 2587
<212> TYPE: DNA
<213> ORGANISM: Reticulitermes flavipes

<400> SEQUENCE: 34
gcgaccacca tgaggacagc agtgctgctc gtgtttctgg ccacagcggc cctagcagct     60
gcaaacccga gcccaagtca agagtccaga atcatcgctg acaagcagtt cctgcagcgg    120
cagaatgact tcctgcgcct cctggtccgc atcgaacaac caaattacta cgaagaccag    180
gtgacactcg gcaattcata cgacatcgaa gtgaacatca aaaactacaa gcaccctcaa    240
gtggtaaagc agttcttgtc agcctacaag aagggtttcc tgcctcgtgg tgtgccatat    300
tctccctact acaccaccca gagctacgag accaagcttc tgttcgatct gttctactac    360
gccaatgact atgacacttt ctacaagact gcagtctggg ctcgtgacag aatcaacgca    420
ggccagttcc tgtacgcctt cagtgtggcc accttcctac gagaggacct gaacgacatc    480
gtgttgccac cccctacga ggtctacccg tacctctttg tagattctga cgtcattcag    540
aaggcttacg agacaaaaat gtgggatcac agtctgacgt cccctaagac gcacgtgttc    600
ccagctaact acactgtgca caccccggaa caagtcctca gctacttcac ggaagacgtt    660
ggactcagca cgtactacct ctactactac tacaactacc ccacgttctt caacagcacc    720
gagtacggcg ttcatttcga ccgtcgcggt gagcagttct actacaagat ccagcaggtc    780
ctcgcccgtt acatcctcga gaggctgtcc cacgaccttc cagaagtcca gcccttccat    840
```

```
tatgacaagc ccttccagac tgcgtactac cctaagctgc gatacgccaa tggacaggaa      900
gttccgttcc gcccatatga atacagcaaa cgcaacctct acaactataa cggccaaggc      960
caatactacg gcaattacta tggcggtaat aacgaatact acagtggcaa ctacttcacc     1020
ggtaactaca agccaaccta ctactacggc tatgccaata actacgatta ctactatcca     1080
gaggatatca agtcctacga gggtcgcatt agagatggca tcgacttcgg atatttcttc     1140
tctgagggag gacaaccaaa gtatcctctg tatgacgagt actcaaaggg catcaattac     1200
cttggtgaca tcattgaggg caacggcgac acagtcaaca gagggtctca cggagccatc     1260
taccaagcct accgccaact agccggacag agcgccgatc cctacaacaa ctatgggctc     1320
gccccaagcg cacttcagaa catcttcacg gctctgaggg accccgccaa ctaccaaatc     1380
ctcaagcgca tcacttacct gttccagagg tacaagaact atctcccaca gtacacgtac     1440
caagagctcg cttatccagg ggttacaatt gaaaatgtgg aagtaggaaa gctgattact     1500
tacaacgatt actttgacat cgacctcgac aacgtagtga acgtgaaagt gcccgaggac     1560
ggtcagtacg tcgactaccg cgcacgccag acacgtctga accacaagcc cttcacctac     1620
agcatagacg taaccagcga caaggcgacc gaagtgtatg tccgagtctt cctgggcccc     1680
aaatacgact acctgggccg cgagtacaat atcaacgacc gcagacatta cttcgtcgag     1740
atcgaccgct tccacacaa gatacaagag ggcaagacga cgatcaagcg aaactcccgc     1800
gactccagtg ttgtcactcc agactatcca agttacagaa ctctgctccg gaaggtgagc     1860
gatgcgctcg agggcaagga gcagttctac atcgacagga gtgaacgcta ctgtggctac     1920
cccgagcgcc tgctgcttcc tagaggcaag aagggaggcc agtccttcac cttctacgtc     1980
atcctgacac cctacgtcca gcagggcgaa catgaattcg agccctacaa ttacaagtca     2040
ttcagctact gtggagttgg cttcaacaac aagtaccctg actataagcc cctcgggtat     2100
ccattcgacc gccccatcta cggtagcgac ttctacacca ccaactcgta cttcaaggac     2160
gtggtcatct tccacaagaa ggaggaagaa gtgaatacag ccatcacaca gtgacacgcc     2220
atgtaactgg agaaatatag ttacgatagc aatacgaggt ggtccaaaag tctctgtgca     2280
gttgcagaca ttaaattatt aagatgagtg gaagtaatcg ttgctgcggc aacaatttgt     2340
ttcattcata tgaggtccaa gtagctaaac aagtccgatc atgaacgaga cccgtctgca     2400
cagggccttt ctgactatta tgtatgacaa gtccgtcctt cgtatttgtt gacgaatcgc     2460
accgaccagg acattctgtg gaaagctgaa tgtaaatgtg ttaccgttta gagactttcg     2520
tttctgtcct tcagaataaa tacccttttt tactagcctg caataaacaa aaaaaaaaa     2580
aaaaaaa                                                              2587
```

<210> SEQ ID NO 35
<211> LENGTH: 1131
<212> TYPE: DNA
<213> ORGANISM: Reticulitermes flavipes

<400> SEQUENCE: 35

```
tatcattgtg cagagaagaa ggcgaaagtg tttgagcagt gaaatatacg tacttggata       60
cagtggggta ccatgttctt ctcatttgtt ttatggatca tcttcttcta tgtggtatat      120
tactggctaa caatgaagcc gaagaacttt ccgccaggtc caccacatgt tcctgtgttt      180
ggatctacct tttacctgct acggaaacat cttcacattc cgatggcagg ggaatggctt      240
cagaaatacg gtcctgttgt gggatttgtg gcggcctctc ggaagatcat agcgatatgt      300
ggaccccgtg aagtccttga agtgctacac agagatgaat tccaagcaag gcctgtcttt      360
```

```
agttttttc atgataggtc tttcggcaaa aaactcgggg tgttttctc tgatggcccg    420 tactgggtag aacagcccag atttactctc agacatttga gagatttcgg tttcggaaaa    480
cgttcaatgg aggagttcat catggaagaa atagaagaca ctatcaagga aattacaaag    540
acagaaatta tgcaggccac tggattgttc actattgcca cactgaacgt tctatggaga    600
atgattgctg gtgcccgata tgcgcgagac gacgctgaaa tgctgatgct tctagagaaa    660
ctgagacttc tgttccggtc tggaagtgcc ggtggaggta ttggtggtgc attccccatc    720
ttaacgaaaa ttgcacccgt attttctggt tacgccttaa tgatgtccac cacttcagat    780
ttgcaggaat ttttcagaaa atccataagg gaacacgaga aaactatgga tgagaataac    840
gcaagagatt taattgatgt gtacttaagg gaaataaaat tacaaggcaa taatccggcc    900
tcaacattca cagaagaagg gctcataacg atctgcctgg acttgttcac tgccggagga    960
gaaaccatgg ccatgtctct aggcttctcc cttctgtaca tgctggtgca cccgaatgtc   1020
caaaaggcgg tgcagaaaga gttggatgca gttgtgggaa gggacaggag acccactctt   1080
caagacagag caagcttaca ctacacagaa gctgtactgt cagagctgat t           1131
```

<210> SEQ ID NO 36
<211> LENGTH: 1074
<212> TYPE: DNA
<213> ORGANISM: Reticulitermes flavipes
<220> FEATURE:
<221> NAME/KEY: modified_base
<222> LOCATION: (944)..(944)
<223> OTHER INFORMATION: a, c, g, t, unknown or other
<220> FEATURE:
<221> NAME/KEY: modified_base
<222> LOCATION: (962)..(962)
<223> OTHER INFORMATION: a, c, g, t, unknown or other
<220> FEATURE:
<221> NAME/KEY: modified_base
<222> LOCATION: (971)..(971)
<223> OTHER INFORMATION: a, c, g, t, unknown or other
<220> FEATURE:
<221> NAME/KEY: modified_base
<222> LOCATION: (980)..(980)
<223> OTHER INFORMATION: a, c, g, t, unknown or other
<220> FEATURE:
<221> NAME/KEY: modified_base
<222> LOCATION: (990)..(990)
<223> OTHER INFORMATION: a, c, g, t, unknown or other
<220> FEATURE:
<221> NAME/KEY: modified_base
<222> LOCATION: (1002)..(1004)
<223> OTHER INFORMATION: a, c, g, t, unknown or other
<220> FEATURE:
<221> NAME/KEY: modified_base
<222> LOCATION: (1007)..(1009)
<223> OTHER INFORMATION: a, c, g, t, unknown or other
<220> FEATURE:
<221> NAME/KEY: modified_base
<222> LOCATION: (1020)..(1021)
<223> OTHER INFORMATION: a, c, g, t, unknown or other
<220> FEATURE:
<221> NAME/KEY: modified_base
<222> LOCATION: (1025)..(1026)
<223> OTHER INFORMATION: a, c, g, t, unknown or other
<220> FEATURE:
<221> NAME/KEY: modified_base
<222> LOCATION: (1041)..(1045)
<223> OTHER INFORMATION: a, c, g, t, unknown or other
<220> FEATURE:
<221> NAME/KEY: modified_base
<222> LOCATION: (1047)..(1049)
<223> OTHER INFORMATION: a, c, g, t, unknown or other
<220> FEATURE:
<221> NAME/KEY: modified_base
<222> LOCATION: (1054)..(1054)
<223> OTHER INFORMATION: a, c, g, t, unknown or other

```
<220> FEATURE:
<221> NAME/KEY: modified_base
<222> LOCATION: (1056)..(1056)
<223> OTHER INFORMATION: a, c, g, t, unknown or other
<220> FEATURE:
<221> NAME/KEY: modified_base
<222> LOCATION: (1059)..(1061)
<223> OTHER INFORMATION: a, c, g, t, unknown or other
<220> FEATURE:
<221> NAME/KEY: modified_base
<222> LOCATION: (1067)..(1068)
<223> OTHER INFORMATION: a, c, g, t, unknown or other
<220> FEATURE:
<221> NAME/KEY: modified_base
<222> LOCATION: (1072)..(1072)
<223> OTHER INFORMATION: a, c, g, t, unknown or other

<400> SEQUENCE: 36
gcatatcaag aactttattt tcgaaaataa aatgtgctcg cacaaagtta aatcacgtag      60
caattgatgt gcgtgcccat ttgcttaaag actgaataac tgaagcctat ggagcagttc     120
ttgaaaaggc ccaacatgga tgccagtggt aggaaaactac ttctggttcc gacagcagaa    180
gctgagtctc ggttactacc acctcgtatg ggctagcctg tcaacaaaat atgggcctgt     240
ggtcgggctc cgactgggca gggactctgt tgtcacggtg tcgggctatg atgctatcag     300
ggatgttttg ctgcgagatg agtttgatgg cagacctgat ggattcttct tccgtttgcg     360
tacttttggg aagcgacttg gagttgtgtt tactgacggc ccgttgtggc aagagcagcg     420
tcgcttctgc ctccaacatc tgcgcaagct gggacttggg aggcgaagca tggacgaaca     480
gatagaagcg gaggcacaag acctggtggt gacattgcag agcaaatgta atgatggatc     540
aacacctctg ccgttccatg atgcttttaa tgtctgtgtt ctgaacagcc tgtgggccat     600
gctggctgga tatcgttttg cactgaatga caaacgcctg atggagctcc ttgacatagt     660
tcatgccagt ttccgtatga tcgatgcatc tggcggatct ctcaatcaga tgcccttcct     720
acgcttcatt gcaccaaatt tgtctggcta caacgagtta cttgcaatcc ttaatcgaat     780
gtggaacttt ctgagggaaa cgatcagtga acatcgcaaa acattcagcc ctgattgtac     840
cagagacctg attgattcat ttcttgagga aatggaactc agaaagaaag aaacagattc     900
agttttatga ctgcagttgt agcactgtgc ctgactgtca tgcngctcaa gacacagcaa     960
cngctcgttc ncatgctgtn tatgctgctn ccctgatgtc cnnnccnnna caaggatgan    1020
ntggnnattg gggtggccga nnnnncnnnt cgcngnacnn nagtagnnaa gntg            1074

<210> SEQ ID NO 37
<211> LENGTH: 1075
<212> TYPE: DNA
<213> ORGANISM: Reticulitermes flavipes
<220> FEATURE:
<221> NAME/KEY: modified_base
<222> LOCATION: (1003)..(1003)
<223> OTHER INFORMATION: a, c, g, t, unknown or other
<220> FEATURE:
<221> NAME/KEY: modified_base
<222> LOCATION: (1008)..(1008)
<223> OTHER INFORMATION: a, c, g, t, unknown or other
<220> FEATURE:
<221> NAME/KEY: modified_base
<222> LOCATION: (1012)..(1012)
<223> OTHER INFORMATION: a, c, g, t, unknown or other
<220> FEATURE:
<221> NAME/KEY: modified_base
<222> LOCATION: (1022)..(1023)
<223> OTHER INFORMATION: a, c, g, t, unknown or other
<220> FEATURE:
<221> NAME/KEY: modified_base
<222> LOCATION: (1025)..(1025)
<223> OTHER INFORMATION: a, c, g, t, unknown or other
```

```
<220> FEATURE:
<221> NAME/KEY: modified_base
<222> LOCATION: (1030)..(1030)
<223> OTHER INFORMATION: a, c, g, t, unknown or other
<220> FEATURE:
<221> NAME/KEY: modified_base
<222> LOCATION: (1035)..(1035)
<223> OTHER INFORMATION: a, c, g, t, unknown or other
<220> FEATURE:
<221> NAME/KEY: modified_base
<222> LOCATION: (1056)..(1056)
<223> OTHER INFORMATION: a, c, g, t, unknown or other
<220> FEATURE:
<221> NAME/KEY: modified_base
<222> LOCATION: (1060)..(1060)
<223> OTHER INFORMATION: a, c, g, t, unknown or other
<220> FEATURE:
<221> NAME/KEY: modified_base
<222> LOCATION: (1068)..(1069)
<223> OTHER INFORMATION: a, c, g, t, unknown or other
<220> FEATURE:
<221> NAME/KEY: modified_base
<222> LOCATION: (1075)..(1075)
<223> OTHER INFORMATION: a, c, g, t, unknown or other

<400> SEQUENCE: 37
tagtggtgtt ggcagcggaa gggaacggtt tgcagtgaac atggctaaag aatttacgac      60
agaagacaaa cttgaatacc aattccatcc tgtaacatca gggaagctgc attttaaggt     120
gcggcaccca aacgatgcgc atgtggcact gacatctggg cccactgaag gggaccctat     180
gtacgagatt tcattggtg ctggggaaa cgcgaagact gccatcagac gagaccgcgt      240
gaaacctgac aaggctctag tcgacacgcc ggacatcctc agtgatgcag aatatcgtgg     300
cttctggatc cgctgggagg atggtttact ggaagttggc aaggaaggtg aagtgacccc     360
ttttgtaagc tggaaggacc ctgaaccgtt tggtatcggc tattacggta tctgcactgg     420
atggggagca tctggctcat ggattataga tggtgccgac gtcgctacgg cagacagttt     480
gcagtacatt taccgccccg tgccagcggg cgcactgcac attgaggttc gtgcccctc      540 caatgcacac attgctctaa catcagccag taatgagaca gaacctatgt acgagattct     600
gcttggaggc tgggagaaca cagcatctgt cattcgctac aaccgccaga accagacaa      660 ggttcgggca gacacgcctg gactcttgac caacagtgac tacagtcgct tcttgataga     720
gtggcataat ggccatgtca gagtgaagaa gatggttctg tgctgctaga atggcaagat     780
cccagcccac ttggaatttc gcactttggt gtgcggacag cttggggtgc tcaggacact     840
ggagggtcca ccctagtgca tcaccagcac cgccacctga tggaaattgc catctgagag     900
ctgctctggg tgcctgctca agttgagacg tcctcaaatg ctgtgaggtg tcacgatagt     960
gagattctgt acatagacga gcagcatgaa ggcgccctga tcngcagntg tnctccatgg    1020
anngntattn catgngagaa ccttggacaa tggagncacn gaaattgnng aggtn          1075

<210> SEQ ID NO 38
<211> LENGTH: 1949
<212> TYPE: DNA
<213> ORGANISM: Reticulitermes flavipes

<400> SEQUENCE: 38
ggcacgaggt gctgatccgg cgttcatgga cgtctataca cagcgcggcg tcaccaggcc      60
ggcgaactgg gcaggtccac aacaggcccc gcccggaaca aaggcggctg tggcccccatc    120 gccacccgtc aaaaagactc tacctctagt ttcacaggca tctcctaagt cagtcatcgc     180
taagccaggt cctccacgac ctgtgtctcc accacaaccc cctccacctc cacccgaagt     240
ttgtcaccgt tggaacagct accattctaa catgcaagct acattcccaa gtctgctgaa     300
```

-continued

```
caatgaacag tttgtggatg tcacattggc ttgtgagggg cgcagtatta aatgtcgtaa      360
agtaatgcta tcagcatgca gctcatactt tgaggagttg ctaagccaga tccctgcca       420 acatcccata gttctcatga aggacctcaa gttctgggag gtgcaggccc ttgtggactt      480
catgtacagg ggggaagtga atgtgggaca agacaaactt ccctctctgc tagcagcagc      540
tgaggcattg cagattaaag ggttggctgg accagcatct acatcttcat cacatgacga      600
agactctctt cccectactc ttccgctcgc aacggatgac tacatggatg aatccgcttc      660
ctcagcttcc agtgcaagaa gggccagaaa gaggagaact attgcatctc tgccaactcc      720
acgacagaac accatctctc cacaccgcaa cccagtgggc cgaccacgtt tgatcaggcc      780 atccctcaa ccatctacat caacttacca tcatacatca gtggcttctg aacctccact       840
tcggcgagcc aggagatctg agccaactag tcttcctatt ggggagatta agatagagcc      900
agtggatatt gacattagca atgattctat agaccctgtt gatgatggat ttgacctcaa      960
caagacttat gacggcagtg gtggaggacg caatgcaaat gactccagta ggcaagcgga      1020
tgacataggg gtagacactg gaggagggag taagcaagaa ctcactggcg atctctcaga      1080
tgacaacaag gcaattacaa gtggacatga ttcagaccac atggattaca gcagcagcag      1140
tggtaacaat ggtatgaact gtgaaccaag tgtggctgcg gcaggtggcg aagcaaggc      1200 agaaggtcag ggatactcat atgctgaacg aaatactgat gacccaggga tgtcttcttc      1260
agacatgaat ccaacatacc cagaagtggt gctgaaacca gggcctgaca atgcttcgtc      1320
agatagcatt cttggacact tgtgaatcag gcttcaacca ctattatgtt tgactgattt      1380
tttatgtata cattcatcca aatcgaggtt ccccactggt aatgcgatgc ttatctgata      1440
tggagtggaa cgagcacatt gcagttcagt acttcagagc atccaaatga gagtttgccg      1500
gccatagtat tcattaggat gatagagttc ctctttaagt tctacagatt cagtatttct      1560
ttagttagaa gtgacatata attttgtaag ccaaatttat aatatacct ttattgaaaa       1620 cgtgacttct gtggtagctt gggaggcttg acctcagaat ctttaaagtg catggattat      1680
acttactaca ggggcgtaca gaattttata aatgtcttgg aatctgtagc ctgtaactta      1740
aaaggtgtga agctgctgta accataaatg agcagacttt ttggcatgta gggtagttat      1800
taaaaccaaa agtggctaga gtcaacaaaa acctagtgtg tagtattgtg gttacagcat      1860
catagcaaca ttagagtatt gagaaggtgt tctgtattca tattcctgaa gaaataaatg      1920
acactttgtg agttgttaag aaaaaaaaa                                        1949
```

<210> SEQ ID NO 39
<211> LENGTH: 1902
<212> TYPE: DNA
<213> ORGANISM: Reticulitermes flavipes

<400> SEQUENCE: 39

```
cacttctcaa gggtagaatg gaacaatctt ttgctttcaa acagttcgtt gctgaaagcc      60
ctatggccaa gttatgcgag tcgcaaatgc gcgaaaaaca atctccttag tgcttgccgt      120
aatgtcactg agcaagccaa cgtactcgac ctgcacaact tcgcgctgaa gtacaacaat      180
atacccgact catggataaa ttacacatac aaggcataca gcgtacttcg tcacttggct      240
ttcccttatg tcactgagaa tattttccca ccaaatccaa aaccgaacca attgcaagtt      300
aacgtacgcc tgaataacaa cattactgcc gtcaacgtat ccattgaaac gccaattatg      360
aacataaatg tcaccaatat ccgcctgaac ccactggcag cagctttact tcagcacaat      420
gcagaagact ctgctgctga cagaattgga aatgccatgt caccactgta ctaccagcct      480
```

-continued

```
acatgcgttg ttgatggcaa tgctgtcgac acgttcgaca acaatacct a tccaattaaa    540 cttggcagct gctggcatgt catgatgatg aagtaccaa agaaccctgc tggagtgcat     600
agtcgtcatc agtcgcgatc ttccctggcc agcagatacc agactagcaa tgtagcggtg   660
ctcgtacgtg gcagcaactc cggaccacag aaggaagtgc aagtgatcct gggagagaat   720
gtcatcacac tgagtcccga gtcaaccagt tcaaataaat tagtggaggt cgctgtgaat   780
gatcgtcaaa tccgattctc acccaacaaa accacggaat tttattacga aggagtgctg   840
gttgtccaag tgtatgagtt gccaagtgga gctgcaaaac tcaacttccc gaaccacagc   900
ttggcgatcg cctacgatgg agagagaatt atgttggagg ctagtaatga ctatcgcgat    960
gaagtccggg gcttgtgcgg aactttcaat ggagatgctc tctctgactt caaaattcca   1020
aagggctgca ttgttaagaa cccatacatc ttcgctgcca cttatgcaat cattgaagag   1080
tcttgcaatg cacagaccaa gaagctgaag gaacgtgtcc atcaagaacc gtgtgtgtat   1140
gacgaggtag agtacgtcga cgtgatcgca gaaaacaggc caaagaacgc tagtgcaaga   1200
ggattcgaac tgcttagttc tgccagtgat tcatcctcat cttcatcgtc atcctcctcc   1260
tcttcttctt cctcctcttc ttcatcgtca tcatcttcat catcatcatc atcatcatca   1320
tcagaatcca attccagttc tgattctgcc tccaattcga cttcaagctc cagttccagc   1380
tctagttcca gctccagttc tagctcggaa tccgatgaag ttaccaaagt cggaaaacac   1440
cagaaagctg gatcaaaagc taattgcata tcacatcgta ccaaggtggt gattgaagga   1500
aacgagattt gcttcagcat gaaaccccctt cccgaatgct cttcacaatg ccgtcccgca   1560
gaaaaacaga agaaaactat caaattccac tgtcttgtca agggacagac agcccagcat   1620
tggcagaata tggtgaacag aggcgtaaat cctgatttca gcaagaaggc tgcgcacaaa   1680
gaaattagta tcaacattcc aatgaagtgt gccagcccctt gaatgacata atatttcagg   1740
attaatggaa atagattttt acggactttc cttatatgta atatttatc tagaatgtgt     1800 gttgaacgtt ttaatttaca gcaatgagca agaaaaaat acataaaaat atgtgtatta    1860
caacttattt atgaagaata tatcaattgc aaaaaaaaaa aa                       1902
```

```
<210> SEQ ID NO 40
<211> LENGTH: 1880
<212> TYPE: DNA
<213> ORGANISM: Reticulitermes flavipes
<220> FEATURE:
<221> NAME/KEY: modified_base
<222> LOCATION: (504)..(504)
<223> OTHER INFORMATION: a, c, g, t, unknown or other
<220> FEATURE:
<221> NAME/KEY: modified_base
<222> LOCATION: (905)..(905)
<223> OTHER INFORMATION: a, c, g, t, unknown or other
<220> FEATURE:
<221> NAME/KEY: modified_base
<222> LOCATION: (1161)..(1161)
<223> OTHER INFORMATION: a, c, g, t, unknown or other
<220> FEATURE:
<221> NAME/KEY: modified_base
<222> LOCATION: (1288)..(1288)
<223> OTHER INFORMATION: a, c, g, t, unknown or other
<220> FEATURE:
<221> NAME/KEY: modified_base
<222> LOCATION: (1295)..(1295)
<223> OTHER INFORMATION: a, c, g, t, unknown or other
<220> FEATURE:
<221> NAME/KEY: modified_base
<222> LOCATION: (1681)..(1681)
<223> OTHER INFORMATION: a, c, g, t, unknown or other
<220> FEATURE:
<221> NAME/KEY: modified_base
```

```
<222> LOCATION: (1817)..(1817)
<223> OTHER INFORMATION: a, c, g, t, unknown or other
<220> FEATURE:
<221> NAME/KEY: modified_base
<222> LOCATION: (1830)..(1830)
<223> OTHER INFORMATION: a, c, g, t, unknown or other
<220> FEATURE:
<221> NAME/KEY: modified_base
<222> LOCATION: (1842)..(1842)
<223> OTHER INFORMATION: a, c, g, t, unknown or other
<220> FEATURE:
<221> NAME/KEY: modified_base
<222> LOCATION: (1856)..(1856)
<223> OTHER INFORMATION: a, c, g, t, unknown or other
<220> FEATURE:
<221> NAME/KEY: modified_base
<222> LOCATION: (1872)..(1872)
<223> OTHER INFORMATION: a, c, g, t, unknown or other

<400> SEQUENCE: 40
```

| | | | | | |
|---|---|---|---|---|---|
| taggagccgt | aaaccacgag | gtttgcccag | gaagcatggg | catagcagtg | aagaaaatga | 60 |
| tttcaaggct | tcgaacccag | caattccaga | atcaagtaca | tctcctgaca | gtaatgctcg | 120 |
| ccggcaggaa | ttcctctcca | aggctgtttc | aatcatcaaa | aatgcatcag | cagcggttat | 180 |
| cgacctctct | gtgaaattcg | agggacgcac | caaagcagag | tttgtaatga | ctgctgcttg | 240 |
| ggcttcatct | ttggtgaacg | gaagtcaaag | cgttctgctc | ttcctgaaat | caattcccgc | 300 |
| ccagcaccca | ctgctccccc | gacaacaaca | gttgcaggta | tgtctagttg | ggaaggtctc | 360 |
| catgcctcca | gtaccagtca | ccaacttcca | tgaagcactt | aaatacgacc | ccaattcttc | 420 |
| tgtgagggcc | cagctaagtt | tcggcgagac | atgtcaacat | ggcgccaccg | tgtccctgaa | 480 |
| gggtgaaatg | gaacaaagcc | acangagaaa | agaatcaatt | gccaatagcc | caatggctaa | 540 |
| gctgtgcaag | tctcagatga | atatgaagaa | tcaccttctg | ccagcctgtc | gtaacgttac | 600 |
| tcaagcagct | aacaatcttg | accattatca | cttcaagatt | atgtttaaca | acattccgga | 660 |
| tgttctgaag | aacggcacat | acaaggtgta | cagtttggca | cgtcgttggc | tatatcctta | 720 |
| cgtgacggag | aatatctatc | ctcaaaaccc | agtaaaagat | gcagtacata | tcattgtcga | 780 |
| tatcaacgaa | gaaagcactg | ctctcaatgt | gacaatggaa | acaccagcca | tgaacgtgaa | 840 |
| catcaccgac | gttcgcctga | aaccttgtgc | acaggcactt | tttaacatga | acccggccca | 900 |
| cacgnttgta | gagcgcattg | gatgtactat | gtctccactt | taccataacc | ccacttgcgt | 960 |
| cgttgacagt | acaatggcca | atacgtttga | taatataact | tacccctatgg | accttggcaa | 1020 |
| atgctggcac | gttatgatga | tggttgttcc | gaaacgtcca | gcagacctct | ctcagcaaca | 1080 |
| ctcatcgcaa | cgtgcacaag | aaagcctgag | cacacttgaa | gaagtgtctg | ttttggtgaa | 1140 |
| ggaagttggt | aacaacaagg | naagttatgg | tgatgacgaa | ttcagcccac | atccatctga | 1200 |
| agcctgctct | ccattctaac | tctgaccaaa | cggttttggt | ccaccataaa | acgacaagcc | 1260 |
| tgtttccgca | caaattttta | ctgggccnta | ctccnctaca | acacgaaggc | aacctgctgg | 1320 |
| cccaagttca | cgaactgcca | gaaggtgcac | tatacctcac | gtttccaaac | aaaagcttgg | 1380 |
| tgatcatcta | cgacggagtg | agggttatgc | tgcaggctag | caacgaatac | cgccaacaaa | 1440 |
| ttagaggtct | ctgtggaaat | atggatggag | aacccttcaa | tgatttcatg | acgccaagta | 1500 |
| actgcctcat | tagggaacca | tccatttta | ctgccactta | tgcaatcgat | gaagaatcat | 1560 |
| gccaacgacc | agcaaagatt | agggaacaaa | tcaggaaaga | agcatgtgtt | caggaaaaga | 1620 |
| ttagcttcgc | agatgttatt | cctaatgcta | agccaaaaag | tgctcgccta | agaggattcc | 1680 |
| naactcattg | aatccgaaag | taacccagac | atcatcttct | ttcctcctcc | tcctcctcct | 1740 |
| catcctcatc | ctcatcctca | tcatcatcat | catcctcatc | atcatcatca | tcatcggtcc | 1800 |

```
-continued tctttcctct tctgagnccc aacttccaan ttcaagcttc angtttccag tttctngaaa    1860
tcaaatgaaa tnttcggaaa                                                1880
```